US010858693B2

(12) United States Patent
Sardar et al.

(10) Patent No.: US 10,858,693 B2
(45) Date of Patent: Dec. 8, 2020

(54) SYSTEMS AND METHODS FOR LOCALIZED SURFACE PLASMON RESONANCE BIOSENSING

(71) Applicant: INDIANA UNIVERSITY RESEARCH & TECHNOLOGY CORPORATION, Indianapolis, IN (US)

(72) Inventors: Rajesh Sardar, Indianapolis, IN (US); Murray Korc, Indianapolis, IN (US); Gayatri K. Joshi, Carmel, IN (US)

(73) Assignee: INDIANA UNIVERSITY RESEARCH & TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 15/517,383

(22) PCT Filed: Oct. 6, 2015

(86) PCT No.: PCT/US2015/054174
§ 371 (c)(1),
(2) Date: Apr. 6, 2017

(87) PCT Pub. No.: WO2016/057474
PCT Pub. Date: Apr. 14, 2016

(65) Prior Publication Data
US 2017/0298426 A1    Oct. 19, 2017

Related U.S. Application Data

(60) Provisional application No. 62/210,731, filed on Aug. 27, 2015, provisional application No. 62/060,284, filed on Oct. 6, 2014.

(51) Int. Cl.
*C12Q 1/68* (2018.01)
*C12Q 1/6825* (2018.01)

(52) U.S. Cl.
CPC ................. *C12Q 1/6825* (2013.01)

(58) Field of Classification Search
CPC ........ C12Q 2565/632; C12Q 2565/518; C12Q 1/6825; C12Q 2525/207; C12Q 2565/628;
(Continued)

(56) References Cited

U.S. PATENT DOCUMENTS

| | | | | |
|---|---|---|---|---|
| 2003/0049639 | A1* | 3/2003 | Nelson | B82Y 15/00 435/6.13 |
| 2012/0101007 | A1* | 4/2012 | Ahern | B22F 1/0022 506/12 |

(Continued)

FOREIGN PATENT DOCUMENTS

| | | |
|---|---|---|
| EP | 2613149 A1 | 7/2008 |
| WO | 2011/109364 A2 | 9/2011 |

(Continued)

OTHER PUBLICATIONS

Li et al "Plasmonic nanorice antenna on triangel nanoarray for surface-enhanced raman scattering detection of hepatitis B virus DNA", Analytical Chemistry, Jan. 15, 2013, 85: 2072-2078. (Year: 2013).*

(Continued)

*Primary Examiner* — Betty J Forman

(57) ABSTRACT

Biosensors and methods for localized surface plasmon resonance biosensing are disclosed. The biosensor can include a substrate having a substrate surface to which a plurality of localized surface plasmon resonance (LSPR) antennae are affixed. The LSPR antennae can be affixed via an affixation surface of the LSPR antenna. The LSPR antennae can have a functional surface opposite the affixation surface. Each functional surface can be functionalized by a plurality of single-stranded DNA.

19 Claims, 14 Drawing Sheets

Specification includes a Sequence Listing.

(58) Field of Classification Search
CPC .... B82Y 30/00; G01N 21/553; G01N 21/554; B01J 2219/00274; B01J 19/0046
See application file for complete search history.

(56) References Cited

U.S. PATENT DOCUMENTS

| | | | | |
|---|---|---|---|---|
| 2013/0148194 A1* | 6/2013 | Altug | ............... | G01N 21/554 359/350 |
| 2013/0190192 A1* | 7/2013 | Lowe | ............... | G01N 33/582 506/4 |
| 2014/0154668 A1* | 6/2014 | Chou | ............... | B82Y 15/00 435/5 |

FOREIGN PATENT DOCUMENTS

| WO | 2013/121011 A1 | 8/2013 |
|---|---|---|
| WO | 2013/160836 A1 | 10/2013 |

OTHER PUBLICATIONS

Sipova et al "Surface plasmohn resonance biosensor for rapid lable-free detection of microribonucleic acid at subfemtomole level" Analytical Chemistry Dec. 15, 2010, 82: 10110-10115. (Year: 2010).*

Joshi et al "Improved localized surface plasmon resonance biosensing sensitiviy based on chemically-synthesized gold nanoprisms as plasmoinic transducers" Journa of Materials Chemistry, 2012, 22: 923-931 (Year: 2012).*

Filmetrics. Refractive Index of SiO2, Fused Silica, Silica, Silicon Dioxide, Thermal Oxide, ThermalOxide. Jan. 9, 2012. paragraph 2 URL:https://web.archive.Org/web/20120109021016/http://www.filmetrics.com/refractive-index-databas e/Si02/Fused-Silica-Silicon-Dioxide-Thermal-Oxide-ThermalOxide, 2 pages.

Joshi, et al., Designing Efficient Localized Surface Plasmon Resonance-Based Sensing Platforms: Optimization of Sensor Response by Controlling the Edge Length of Gold Nanoprisms, The Journal of Physical Chemistry. Sep. 2012, vol. 116, pp. 20990-21000.

Joshi, et al. Temperature-Controlled Reversible Localized Surface Plasmon Resonance Response of Polymer-Functionalized Gold Nanoprisms in the Solid State, J. Phys. Chem. C 2013, 117, 26228-26237.

Joshi, et al., Ultrasensitive Photorevsersible Molecular Sensors of Azobenzene Functionalized Plasnomic Nanoantennas, Nano Letters 14, 532-540 (2014).

Lawrence, et al., Solvent-like ligand-coated ultrasmall cadmium selenide nanocrystals: strong electronic coupling in a self-organized assembly, Nanoscale 2015, 7, 11667-11677.

Liu, et al., Cdk4/6 Inhibition Induces Epithelial-Mesenchymal Transition and Enhances Invasiveness in Pancreatic Cancer Cells, Mol. Cancer Ther. 2012, 11, 2138-2148.

Livak, et al., Analysis of Relative Gene Expression Data Using Real-Time Quantitative PCT and the 2-$\Delta\Delta$CT, Method. Methods. 25, 402-408 (2001).

Ouyang, et al., microRNA-10b enhances pancreatic cancer cell invasion by suppressing TIP30 expression and promoting EGF and TGF-[beta] actions, Oncogene 2014, 33, 4664-4674.

Qavi, et al., Multiplexed Detection and Label-Free Quantitation of microRNAs using Arrays of Silicon Photonic Microring Resonators, Angew Chem Int Ed Engl. Jun. 2010. vol. 49, pp. 1-9.

Ren, et al., A Highly Sensitive and Selective Electrochemical Biosensor for Direct Detection of MicroRNAs in Serum, Anal. Chem. Apr. 2013. vol. 85, pp. 4784-4789.

Steel, et al., Immobilization of Nucleic Acids at Solid Surfaces: Effect of Oligonucleotide Length on Layer Assembly, Biophysical Journal. Aug. 2000. vol. 79, pp. 975-981.

Yanli, Ternary Sensing Surface with DNA-Based Spacer Group: Characterization, Comparison and Optimization, Nanyang Technological University, School of Materials Science and Engineer, Abstract, 2013, 14 pages.

International Search Report and Written Opinion from PCT/US2015/054174, dated Jan. 12, 2016, 23 pages.

* cited by examiner

SEQUENCE LISTING

<160> NUMBER OF SEQ ID NOS: 9

<210> SEQ ID NO 1
<211> LENGTH: 22
<212> TYPE: DNA
<213> ORGANISM: Homo sapiens

<400> SEQUENCE: 1
tcaacatcag tctgataagc ta                                    22

<210> SEQ ID NO 2
<211> LENGTH: 23
<212> TYPE: DNA

```
<213> ORGANISM: Homo sapiens

<400> SEQUENCE: 2
cacaaattcg gttctacagg gta                                              23

<210> SEQ ID NO 3
<211> LENGTH: 22
<212> TYPE: RNA
<213> ORGANISM: Homo sapiens

<400> SEQUENCE: 3
uagcuuauca gacugauguu ga                                               22

<210> SEQ ID NO 4
<211> LENGTH: 23
<212> TYPE: RNA
<213> ORGANISM: Homo sapiens

<400> SEQUENCE: 4
uacccuguag aaccgaauuu gug                                              23

<210> SEQ ID NO 5
<211> LENGTH: 22
<212> TYPE: RNA
<213> ORGANISM: Homo sapiens

<400> SEQUENCE: 5
uagcagcacg uaaauauugg cg                                               22

<210> SEQ ID NO 6
<211> LENGTH: 21
<212> TYPE: RNA
<213> ORGANISM: Homo sapiens

<400> SEQUENCE: 6
cauuauuacu uuugguacgc g                                                21

<210> SEQ ID NO 7
<211> LENGTH: 22
<212> TYPE: RNA
<213> ORGANISM: Homo sapiens

<400> SEQUENCE: 7
uaacacuguc ugguaaagau gg                                               22

<210> SEQ ID NO 8
<211> LENGTH: 22
<212> TYPE: RNA
<213> ORGANISM: Homo sapiens

<400> SEQUENCE: 8
uggaguguga caaugguguu ug                                               22

<210> SEQ ID NO 9
<211> LENGTH: 23
<212> TYPE: RNA
<213> ORGANISM: Homo sapiens

<400> SEQUENCE: 9
uacccuguag auccgaauuu gug                                              23
```

SYSTEMS AND METHODS FOR LOCALIZED SURFACE PLASMON RESONANCE BIOSENSING

CROSS-REFERENCE TO RELATED APPLICATIONS

This disclosure represents the U.S. National Stage of International Application No. PCT/US2015/054174, filed Oct. 6, 2015, which is incorporated herein by reference in its entirety, and which is related to, claims priority to, and incorporates by reference for all purposes U.S. Provisional Patent Application Nos. 62/060,284, filed Oct. 6, 2014, and 62/210,731, filed on Aug. 27, 2015.

STATEMENT REGARDING FEDERALLY SPONSORED RESEARCH

This invention was made with government support under CA075059 awarded by the National Institutes of Health. The government has certain rights in the invention.

SEQUENCE LISTING

The sequence listing is filed with the application in electronic format only and is incorporated by reference herein. The sequence listing text file "IURTC201504503_ST25.txt" was created on Oct. 5, 2015, and is 1676 bytes in size.

BACKGROUND

The field of the disclosure is biosensing. More particularly, the disclosure relates to localized surface plasmon resonance biosensing.

MicroRNAs (miRs) are small noncoding RNAs that regulate mRNA stability and/or translation. Due to their release into the circulation and their remarkable stability, miR levels in plasma and other biological fluids can serve as diagnostic and prognostic disease biomarkers. However, quantifying miRs in the circulation is challenging due to issues with sensitivity and specificity.

Pancreatic ductal adenocarcinoma (PDAC)-related deaths are a major health concern in the United States since the five-year survival rate is only 6%. A crucial contributor to this dismal statistic is the absence of a biomarker for early PDAC detection. Moreover, most patients with PDAC do not develop specific symptoms until the disease is quite advanced. Therefore, at clinical presentation, PDAC patients often have locally advanced and/or metastatic disease, which precludes effective therapy in the vast majority of patients. In this context microRNAs (miRs), which are small single-stranded, non-coding RNAs often play a major role in cell proliferation, survival, migration, invasion, and metastasis in various cancers, including PDAC. Moreover, miRs are released into the circulation, where they exhibit remarkable stability. Therefore, the development of sensitive and specific detection techniques, which precisely and quantitatively measure the concentration of miRs in their native environments such as blood or plasma, may provide a unique opportunity for developing diagnostic and prognostic markers in PDAC.

Microarrays and quantitative reverse transcription polymerase chain reaction (qRT-PCR) assays and are routinely used to detect miRs. However, these methods are semi-quantitative, require sequence-based amplification and radioactive labeling steps, and suffer from cross-hybridization and invalid internal controls. Other analytical techniques such as electrochemical and fluorescence-based assays are also used to quantify the miRs. However, such techniques require either additional amplification or labeling, or complex electron/energy transfer processes, and cannot be performed in physiological media. A few label-free techniques such as photonic microring resonators, nanopores, and nanoparticle-based bio-barcode gel assay can detect miRs associated with cancer patients. However, microring resonators suffer from low sensitivity and do not work in physiological media. Although nanopore-based sensors have shown the ability to detect miRs in the circulation of lung cancer patients, the technique requires a complicated fabrication procedure, a high probe concentration, and a specific probe signature. The bio-barcode gel technique relies on complex sandwich type capturing methods, uses of the toxic chemical potassium cyanide, and may not be applicable to clinically relevant patient samples.

Plasmonic nanostructures have gained significant attention because of their geometrical feature-dependent localized surface plasmon resonance (LSPR) properties, which can be further controlled by modulating their local dielectric environment. Utilizing these properties, several molecular and biological sensors have been developed where analyte binding to nanostructure surface-bound receptors results in an increase in refractive index and consequently a LSPR peak shift. In this context, it has not been possible to detect and quantify sequence specific miRs by their direct hybridization to nanostructure probes followed by monitoring the LSPR properties of nanostructures without using labeling steps.

Accordingly, it would be beneficial to provide a biosensor that overcomes the aforementioned drawbacks.

SUMMARY

The present disclosure overcomes the aforementioned drawbacks by providing systems and methods for localized surface plasmon resonance biosensing.

In one aspect, this disclosure provides a biosensor. The biosensor can include a substrate having a substrate surface to which a plurality of localized surface plasmon resonance (LSPR) antennae are affixed. The LSPR antennae can be affixed via an affixation surface of the LSPR antenna. The LSPR antennae can have a functional surface opposite the affixation surface. Each functional surface can be functionalized by a plurality of single-stranded DNA.

In another aspect, this disclosure provides a method of detecting the presence of or quantifying the amount of a microRNA of interest in a medium suspected of containing the microRNA of interest. The method can include one or more of the following steps: contacting a biosensor with the medium, the biosensor including a plurality of localized surface plasmon resonance (LSPR) antennae affixed to a substrate surface, each LSPR antenna having a functional surface functionalized by a plurality of single-stranded DNA (ssDNA) that is complementary to at least a portion of the microRNA of interest; measuring an absorption spectrum of the plurality of LSPR antennae, the absorption spectrum having a peak wavelength; and determining the presence of the microRNA of interest in the medium based on the peak wavelength.

In yet another aspect, this disclosure provides a method of diagnosing a disease state in a subject, wherein the disease state is indicated by the presence of a microRNA of interest in a serum sample from the subject. The method can include one or more of the following steps: contacting a biosensor with the serum sample, the biosensor including a plurality of localized surface plasmon resonance (LSPR) antennae affixed to a substrate surface, each LSPR antenna having a functional surface functionalized by a plurality of single-stranded DNA (ssDNA) that is complementary to at least a portion of the microRNA of interest; measuring an absorption spectrum of the plurality of LSPR antennae, the absorption spectrum having a peak wavelength; determining a concentration of the microRNA of interest in the serum sample based on the difference between the peak wavelength and an unbound absorption peak wavelength that is measured in the absence of the microRNA; and diagnosing the disease state or altering a treatment regimen based on the peak wavelength or the difference between the peak wavelength and unbound absorption peak wavelength.

In another aspect, this disclosure provides kits including a biosensor and a plurality of single-stranded DNA (ssDNA). The biosensor can include a substrate having a substrate surface to which a plurality of localized surface plasmon resonance (LSPR) antennae are affixed, the LSPR antennae affixed via an affixation surface of the LSPR antenna, the LSPR antennae including a functional surface opposite the affixation surface. The plurality of ssDNA can be adapted to functionalize the functional surface.

The foregoing and other aspects and advantages of the disclosure will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

DETAILED DESCRIPTION

Figure 1:
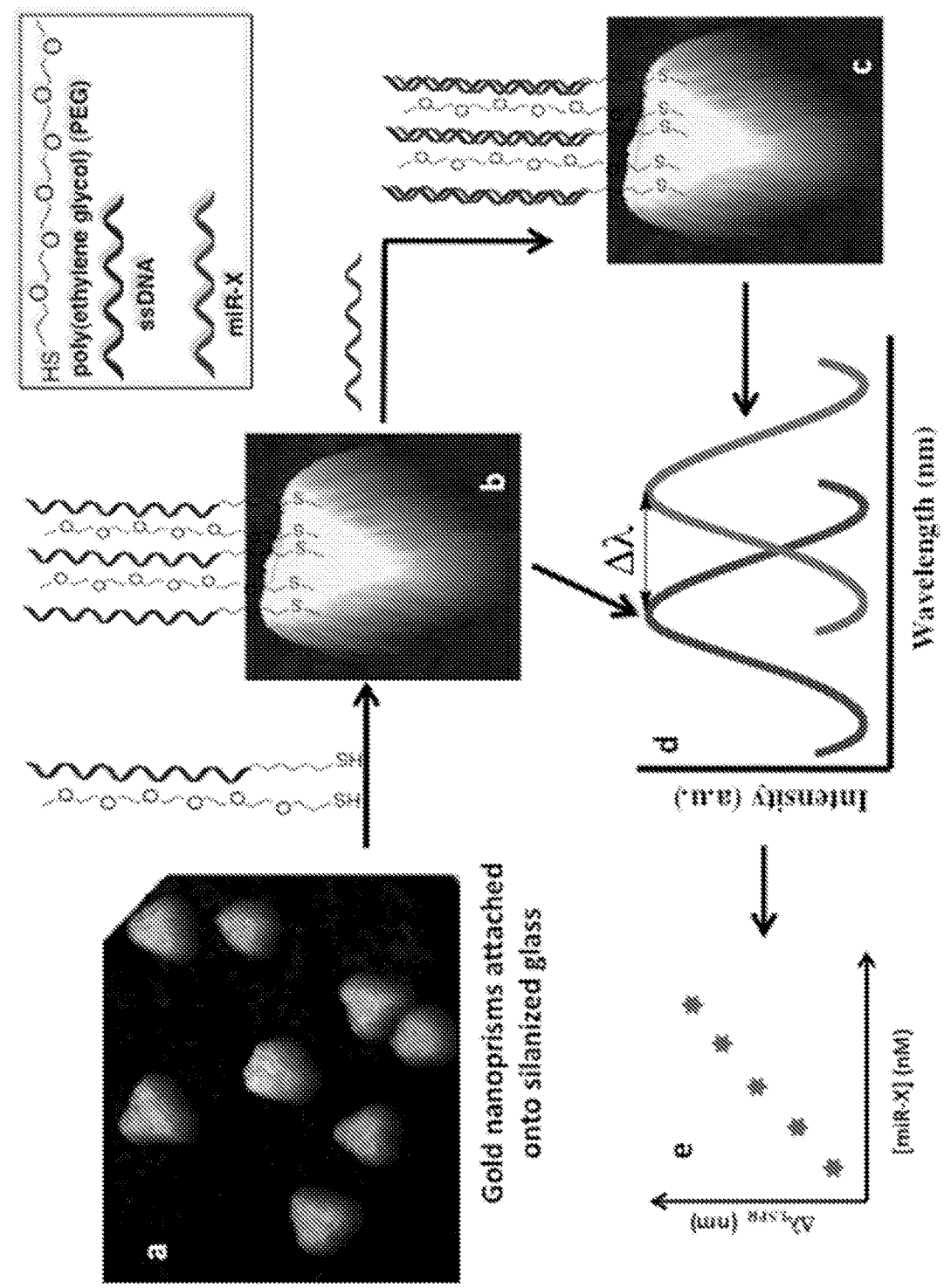
FIG. 1. Design of plasmonic biosensors and detecting miR-X in various physiological media. (a) Chemically-synthesized and freshly prepared gold nanoprisms were covalently attached onto a 3-mercaptopropyltriethoxy silane-functionalized glass coverslip (substrate). (b) Surface of gold nanoprisms was chemically modified with a 1 µM 1:1 mixture of SH-C6-ssDNA-X and PEG6-SH in PBS buffer (pH 7.4) to prepared the plasmonic biosensor. The extinction spectra of the biosensor were collected in PBS buffer to determine the LSPR dipole peak position (blue curve in (d)). (c) Incubation of sensor in miR-X solution and formation of DNA duplex. After carefully rinsing with PBS buffer, extinction spectra were recorded (red curve in (d)) to determine the new LSPR dipole peak position. (d) The extent of dipole peak shift ($\Delta\lambda_{LSPR}$) depends on the concentration of miR-X used during the incubation in c, which ranged from 100 nM to 50 fM e, Plot of $\Delta\lambda_{LSPR}$ vs. log of miR-X concentrations used to determine the limit of detection.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Features of this disclosure described with respect to a particular method, apparatus, composition, or other aspect of the disclosure can be combined with, substituted for, integrated into, or in any other way utilized with other methods, apparatuses, compositions, or other aspects of the disclosure, unless explicitly indicated otherwise or necessitated by the context. For clarity, an aspect of the invention described with respect to one method can be utilized in other methods described herein, or in apparatuses or with compositions described herein, unless context clearly dictates otherwise.

This disclosure is based on the discovery that a plurality of localized surface plasmon resonance antennae having single-stranded DNA (ssDNA) affixed to their surface have an absorption peak wavelength shift or a full width at half maximum (FWHM) shift when the antennae are contacted by a microRNA of interest that is complementary to the ssDNA. This discovery has led to the creation of biosensors, methods, and kits that can provide a low limit of detection for sensing the presence of the microRNA. This disclosure is also based on the discovery that the absorption peak wavelength shift or FWHM shift is proportional to the concentration of microRNA of interest in a sample, thus allowing the concentration to be determined by measuring the absorption peak wavelength shift.

Biosensors

This disclosure provides a biosensor. The biosensor can include one or more of the following: a substrate having a substrate surface; and a localized surface plasmon resonance (LSPR) antenna affixed to a substrate surface. In some aspects, the biosensor can have a plurality of LSPR antennae affixed to the substrate surface.

The LSPR antennae can include an affixation surface and a functional surface. The LSPR antennae can be affixed via the affixation surface of the LSPR antenna. The functional surface can be opposite the affixation surface. Each functional surface can be functionalized by a plurality of single-stranded DNA (ssDNA). In certain aspects, the affixation surface and the functional surface are substantially parallel to one another.

In certain aspects, the ssDNA can be complementary to at least a portion of a microRNA of interest. In certain aspects, the ssDNA can be complementary to the microRNAs of interest disclosed herein. In certain aspects, the ssDNA has a sequence that is the sequence of ssDNA-10b or ssDNA-21.

In certain aspects, the ssDNA can include between 15 and 30 nucleotides or between 20 and 25 nucleotides. In certain aspects, the ssDNA can include 22 or 23 nucleotides.

In certain aspects, the ssDNA can comprise a functional moiety that enables binding to the functional surface. In certain aspects, the functional moiety can be a thiol functional moiety, an amine functional moiety, a carboxylate functional moiety, a phosphonate functional moiety, or a combination thereof. The functional moiety can be located at a terminal end of the ssDNA. In certain aspects, the functional moiety can be located at the 5'-terminal end of the ssDNA.

In certain aspects, the ssDNA can be bound to the functional moiety via a linker moiety. The linker moiety can be selected from the group consisting of an alkyl moiety, an alkenyl moiety, an alkynyl moiety, a saturated and/or unsaturated ring moiety, a short chain alkyl moiety, a polyethylene glycol moiety, and combinations thereof. In certain aspects, the linker moiety can include two or more conjugated double bonds.

In certain aspects, the functional surface can be functionalized by a plurality of spacer molecules. The plurality of spacer molecules can comprise a spacer tail moiety. In certain aspects, the spacer tail moiety can be a poly-ethylene glycol moiety, an alkyl moiety, or a combination thereof. The plurality of spacer molecules can comprise a spacer functional moiety. In certain aspects, the spacer functional moiety can be a thiol functional moiety, an amine functional moiety, a carboxylate functional moiety, a phosphonate functional moiety, or a combination thereof. As with the ssDNA, the functional moiety on the spacer molecule can enable binding to the functional surface.

In certain aspects, the functional surface can have a ratio of number of ssDNA to number of spacer molecules between 1:99 and 99:1, between 1:50 and 50:1, between 1:25 and 25:1, between 1:10 and 10:1, between 1:5 and 5:1, between 1:3 and 3:1, between 1:2 and 2:1, or about 1:1.

In certain aspects, the plurality of LSPR antennae can comprise gold, silver, copper, palladium, aluminum, or a combination thereof. The plurality of LSPR antennae can be a plurality of nanoprisms. As used herein, "nanoprism" refers to a nanostructure having two faces that are substantially parallel to one another. The functional surface can be substantially triangular, substantially circular, substantially ovular, substantially quadrilateral, substantially star-shaped, or a combination thereof. Each of the plurality of LSPR antennae can have an average edge-length of between 10 nm and 150 nm, between 20 nm and 75 nm, between 25 nm and 50 nm, between 30 nm and 45 nm, or between 33 nm and 40 nm. In certain aspects, each of the plurality of LSPR antennae can have an average edge-length of 34 nm, 35 nm, 42 nm, or 47 nm.

In certain aspects, the substrate can be substantially transparent to electromagnetic radiation having a wavelength between 350 nm and 1200 nm or between 700 nm and 900 nm. In certain aspects, the substrate can comprise glass, quartz, indium tin oxide, optical fiber, flexible plastic, gold-coated glass, sapphire, or a combination thereof. In certain aspects, the substrate can be silanized glass.

In certain aspects, the LSPR antenna can have an unbound absorption peak wavelength when contacted by a medium lacking a microRNA of interest that has a sequence that is at least partially complementary to the ssDNA and a bound absorption peak wavelength when contacted by a medium containing microRNA of interest, wherein the bound absorption peak wavelength is shifted relative to the unbound absorption peak wavelength by an amount proportional to the concentration of the microRNA of interest in the medium. In certain aspects, the LSPR antennae can have an unbound full width at half maximum (FWHM) when contacted by a medium lacking a microRNA of interest that has a sequence that is at least partially complementary to the ssDNA and a bound FWHM when contacted by a medium containing microRNA of interest, wherein the bound FWHM is shifted relative to the unbound FWHM by an amount proportional to the concentration of the microRNA of interest in the medium.

It should be appreciated that the medium can be selected from media in which the microRNA of interest is stable, the base-pairing interaction between the microRNA of interest and ssDNA are not interrupted, and which are not corrosive or destructive to the LSPR antennae, the substrate, the ssDNA, or the spacer molecules. In certain aspects, the medium can be selected from the group consisting of human plasma, bovine plasma, phosphate buffered saline, water, serum, whole blood, pancreatic juice, urine, bile juice, saliva, liquid stool, peritoneal fluid, cerebrospinal fluid, and combinations thereof.

In certain aspects, the biosensors described herein function without labeling or amplification of the microRNA of interest.

In certain aspects, the biosensors described herein can have a limit of detection of the microRNA of interest of less than 50 fM, less than 40 fM, less than 30 fM, less than 25 fM, less than 10 fM, less than 1 fM, less than 500 aM, less than 100 aM, less than 50 aM, less than 25 aM, less than 10 aM, less than 1 aM, less than 500 zM, or less than 100 zM.

The biosensors described herein can have selectivity for microRNA of interest having only 1 nucleotide difference from another microRNA. For example, the biosensors described herein can distinguish between miR-10a and miR-10b, as well as other pairs of microRNA that differ by only a single nucleotide.

In certain aspects, the microRNA of interest can be a member of the let 7 miR family, -5p miRs, miR-3p miRs, edited miRs, loop miRs, and the like. In certain aspects, the microRNA of interest can be miR-7, miR-7-2, miR-7-2*, miR-9*, miR-10a, miR-10b, miR-15a, miR-15b, miR-16, miR-16-1, miR-16-2, miR-17, miR-18a, miR-18b, miR-19a, miR-19a*, miR-19b* miR-19b, miR-19b-2, miR-20a, miR-20b, miR-21, miR-21*, miR-22, miR-22-3p, miR-23a, miR-23a*, miR-24, miR-24*, miR-24-2*, miR-25, miR-25*, miR-26a, miR-26b, miR-27a, miR-27a*, miR-27b, miR-27b*, miR-28, miR-28-3p, miR-29a, miR-29a*, miR-29b, miR-29c, miR-29c*, miR-30a*, miR-30a-3p, miR-30a-5p, miR-30b, miR-30c, miR-30c-1, miR-30c-2, miR-30d, miR-30e, miR-30e*, miR-31, miR-31*, miR-32, miR-33a, miR-33a*, miR-33a-loop, miR-34a, miR-34b*, miR-34a-loop, miR-34c-5p, miR-92a, miR-92a*, miR-92b, miR-92b*, miR-93, miR-93* miR-95, miR-96, miR-99a, miR-99b, miR-99b*, miR-100, miR-100*, miR-101, miR-101*, miR-103, miR-103a, miR-106a, miR-106b, miR-106b*, miR-107, miR-122, miR-124, miR-124*, miR-125a, miR-125b, miR-125b-1, miR-125b-2, miR-126, miR-126*, miR-128, miR-129-1, miR-129-2, miR-129-3p, miR-129-5p, miR-130a, miR-130b, miR-130b*, miR-132, miR-133a, miR-133a*, miR-133b, miR-134, miR-135b, miR-135b*, miR-136, miR-136*, miR-139, miR-140, miR-140-3p, miR-141, miR-141*, miR-142, miR-142-3p, miR-143, miR-143*, miR-144*, miR-145, miR-146a, miR-147, miR-147b, miR-148a, miR-148a*, miR-148b, miR-148b*, miR-150, miR-151, miR-153, miR-154, miR-154*, miR-155, miR-181a, miR-181a*, miR-181a-2, miR-181a-2*, miR-181b, miR-181c, miR-182, miR-183, miR-184, miR-185, miR-186, miR-187, miR-190, miR-190a, miR-190b, miR-191, miR-192, miR-192-loop, miR-193b, miR-193b*, miR-193b-3p, miR-194, miR-194* miR-195, miR-196, miR-196a, miR-196b, miR-198, miR-199a-3p, miR-199a-5p, miR-199b-3p, miR-199b-5p, miR-200a, miR-200b, miR-200c, miR-200c*, miR-203, miR-204, miR-205, miR-208, miR-210, miR-212, miR-215, miR-216, miR-216a, miR-216b, miR-217, miR-218-1, miR-218-2, miR-219-1-3p, miR-219-2, miR-219-3p, miR-219-5p, miR-219-loop, miR-219-2-loop, miR-221, miR-222, miR-222*, miR-223, miR-223*, miR-301a, miR-320a, miR-320b, miR-320b*, miR-323-3p, miR-324, miR-324-3p, miR-330-5p, miR-331, miR-331-3p, miR-335, miR-337-3p, miR-338-5p, miR-339, miR-340, miR-342, miR-342-3p, miR-342-5p, miR-345, miR-361, miR-362, miR-362-3p, miR-363, miR-365, miR-369*, miR-370, miR-373, miR-374a, miR-374a*, miR-375, miR-376a, miR-376a-1, miR-376b, miR-376c, miR-377, miR-377*, miR-379, miR-379*, miR-381, miR-381*, miR-382, miR-383, miR-409*, miR-410*, miR-411, miR-411*, miR-421, miR-423-5p, miR-431, miR-432, miR-432*, miR-433, miR-449a, miR-449b, miR-450b-5p, miR-451, miR-451a, miR-452, miR-454, miR-455, miR-455-3p, miR-484, miR-486, miR-486-3p, miR-486-5p, miR-487b, miR-490-3p, miR-492, miR-493*, miR-494, miR-497, miR-497*, miR-499-5p, miR-501*, miR-501-5p, miR-505, miR-508-3p, miR-509-5p, miR-512-3p, miR-513-3p, miR-516a-1, miR-516a-2, miR-516a-3p, miR-516b-1, miR-518d-3p, miR-518e, miR-518f, miR-520c-3p, miR-532, miR-539, miR-542*, miR-542-5p, miR-543, miR-548am, miR-548au, miR-548c, miR-548o, miR-548b-5p, miR-551b, miR-551b*, miR-552, miR-554, miR-566, miR-571, miR-575, miR-582, miR-582-3p, miR-584, miR-589, miR-589*, miR-590-5p, miR-592, miR-598, miR-604, miR-605, miR-614, miR-615, miR-616, miR-616*, miR-622, miR-625, miR-627, miR-628-3p, miR-635, miR-636, miR-639, miR-640, miR-641, miR-642b, miR-642b-3p, miR-643, miR-644, miR-646, miR-648, miR-649, miR-650, miR-652, miR-654*, miR-654-5p, miR-656, miR-672, miR-708, miR-711, miR-744*, miR-762, miR-766, miR-769-5p, miR-801, miR-874, miR-875-5p, miR-877, miR-885-5p, miR-886-5p, miR-888, miR-889, miR-889*, miR-891a, miR-922, miR-923, miR-935, miR-937, miR-939, miR-941, miR-944, miR-1207, miR-1246, miR-1288, miR-1295, miR-1468, miR-1909, miR-2355, miR-2964a, miR-3125, miR-3154, miR-3177, miR-3184, miR-3188, miR-3605, miR-3942, miR-4253, miR-4286, miR-4529, miR-4646, miR-4653, miR-4666, miR-4667, miR-4697, miR-4716, miR-4720, miR-4758, miR-4760, miR-4776-1, miR-4776-2, let-7a-2, let-7a*, let-7b, let-7c, let-7d, let-7e, let-7f, let-7g, let-7i, and the like.

The biosensors can further include any features, structures, chemicals, or reagents described herein.

Methods of Detecting or Quantifying MicroRNAs

This disclosure also provides a method of detecting the presence of or quantifying the amount of a microRNA of interest in a medium suspected of containing the microRNA of interest. The method can include one or more of the following steps: contacting a biosensor having a plurality of antennae as described herein with the medium; measuring an absorption spectrum of the LSPR antenna, the absorption spectrum having a peak wavelength; and determining the presence of the microRNA in the medium based on the peak wavelength. The method can further include determining a concentration of the microRNA of interest in the medium based on the difference between the peak wavelength and an unbound absorption peak wavelength that is measured in the absence of the microRNA of interest.

This disclosure further provides a method of detecting the presence of or quantifying the amount of a microRNA of interest in a cellular compartment suspected of containing the microRNA of interest. The method can include one or more of the following steps: isolating the cellular compartment; extracting RNA from the isolated cellular compartment; suspending the extracted RNA in a medium; contacting a biosensor with the medium containing the extracted RNA, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the microRNA of interest; measuring an absorption spectrum of the LSPR antenna, the absorption spectrum having a peak wavelength; and determining the presence of or quantifying the amount of the microRNA of interest in the cellular compartments based on the peak wavelength. The method can also be applied to a plurality of cellular compartments.

This disclosure also provides a method of detecting the presence of or quantifying the amount of a microRNA of interest in a cellular compartment suspected of containing the microRNA of interest. The method can include one or more of the following steps: isolating the cellular compartment; contacting a biosensor with the cellular compartment, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the microRNA of interest; measuring an absorption spectrum of the LSPR antenna, the absorption spectrum having a peak wavelength; and determining the presence of or quantifying the amount of the microRNA of interest in the cellular compartments based on the peak wavelength. The method can also be applied to a plurality of cellular compartments.

In certain aspects, the methods described above can be adapted to further determine the presence of or quantify the amount of microRNA in a supernatant from one or more centrifugation steps in processing a sample. For example, when isolating the cellular compartment or compartments, a biological sample can be centrifuged. The supernatant can be used to contact the biosensor as described elsewhere herein, and the presence or quantity of microRNA in the supernatant can be determined.

In certain aspects, the contacting step can include an incubation time. In principle the incubation time can be a length of time that is sufficient to allow the complexing between the microRNA of interest and the corresponding ssDNA. Of course, the ideal time is the length of time required to allow the complexing to occur, and not longer than that amount of time. Nonetheless, this disclosure encompasses all functional incubation times, whether shorter or longer than is absolutely ideal. The incubation time can range from 1 minute to 24 hours, from 5 minutes to 12 hours, from 30 minutes to 6 hours, from 1 hour to 5 hours, from 2 hours to 4 hours, from 2.5 hours to 3.5 hours, or from 1 hour to 4 hours.

In certain aspects, the contacting step can include an incubation temperature. In principle, the incubation temperature can be a temperature that is suitable for the complexing between the microRNA of interest and the corresponding ssDNA. Of course, certain temperatures are preferably to others due to the thermodynamics of the complexing process. Nonetheless, this disclosure encompasses all functional incubation temperatures, whether higher or lower than is absolutely ideal. The incubation temperature can range from 0° C. to 50° C., from 5° C. to 40° C., from 10° C. to 30° C., from 20° C. to 25° C. The incubation temperature can be room temperature. The incubation temperature can be 5° C.

In certain aspects, determining the concentration can include using a calibration curve.

In certain aspects, the method further comprises contacting the biosensor with a cleaving enzyme to separate the microRNA of interest from the ssDNA thus regenerating the biosensor.

In certain aspects, the methods do not require labeling or amplification of the microRNA of interest.

In certain aspects, the methods described herein can have a limit of detection of the microRNA of interest of less than 50 fM, less than 40 fM, less than 30 fM, less than 25 fM, less than 10 fM, less than 1 fM, less than 500 aM, less than 100 aM, less than 50 aM, less than 25 aM, less than 10 aM, less than 1 aM, less than 500 zM, or less than 100 zM.

The methods of detecting microRNAs can further include any features, structures, chemicals, or reagents described herein.

Methods of Diagnosing a Disease State in a Subject

This disclosure also provides a method of diagnosing a disease state in a subject, where the disease state is indicated by the presence of a microRNA of interest in a serum sample from the subject. The method can include one or more of the following steps: contacting a biosensor having a localized surface plasmon resonance (LSPR) antenna as described herein with the serum sample; measuring an absorption spectrum of the LSPR antenna, the absorption spectrum having a peak wavelength; determining a concentration of the microRNA of interest in the serum sample based on the difference between the peak wavelength and an unbound absorption peak wavelength that is measured in the absence of the microRNA; diagnosing the disease state or altering a treatment regimen based on the concentration of the microRNA of interest in the serum sample.

This disclosure further provides a method of diagnosing a disease state in a subject, wherein the disease state is indicated by the presence of a microRNA of interest in a cellular compartment from the subject. The method can include one or more of the following steps: isolating the cellular compartment; extracting RNA from the isolated cellular compartment; suspending the extracted RNA in a medium; contacting a biosensor with the medium containing the extracted RNA, the biosensor comprising a localized surface plasmon resonance (LSPR) antenna affixed to a substrate surface, the LSPR antenna having a functional surface functionalized by a plurality of single-stranded DNA (ssDNA) that is complementary to at least a portion of the microRNA of interest; measuring an absorption spectrum of the plurality of LSPR antennae, the absorption spectrum having a peak wavelength; determining a concentration of the microRNA of interest in the cellular compartment based on the difference between the peak wavelength and an unbound absorption peak wavelength that is measured in the absence of the microRNA; and diagnosing the disease state or altering a treatment regimen based on the concentration of the microRNA of interest in the cellular compartment. The cellular compartment can be an exosome. In some aspects, the mention discussed in the paragraph can excludes the extracting and suspending steps, and can involve contacting the biosensor with the cellular compartment rather than with the medium.

In certain aspects, the disease state can be pancreatic ductal adenocarcinoma (PDAC), all other solid cancers and their subtypes, such as breast and ovarian cancer, uterine cancer, colorectal cancer, gastric cancer, cholangiocarcinoma, ampulla of Vater cancer, thyroid cancer, parathyroid cancer, head and neck cancer, esophageal cancer, liver cancer, kidney cancer, genito-urinary cancers, bladder and prostate cancer, mesothelioma, lung cancers, skin cancers such as basal cell carcinoma and squamous cell carcinoma and melanoma, other skin conditions such as skin rashes and psoriasis, glioblastomas and other central nervous system tumors, sarcomas, preneoplastic lesions and cystic lesions that may precede solid cancers, lympho-proliferative disorders such as leukemias, lymphomas, multiple myeloma, inherited cancers, and diseases other than cancer. Such diseases include, but are not limited to, diabetes mellitus, type I, type II, and pancreatogenic diabetes mellitus and the complications associated with these diabetes disorders, other endocrine and metabolic disorders, cardiovascular diseases include myocardial infarction, atherosclerosis, stroke, hypertension and its complications, vascular aneurysms, lipid disorders, inflammatory disorders of all organ systems including acute pancreatitis, hepatitis, cholangitis, colitis, glomerulonephritis, acute interstitial nephritis, and other acute inflammatory states, pulmonary disorders including chronic obstructive pulmonary diseases and pulmonary emboli, autoimmune disorders, gastrointestinal disorders including chronic pancreatitis, liver diseases including cirrhosis of the liver and steatohepatitis, chronic viral liver infections such as hepatitis B and C viruses, and kidney diseases, muscolo-skeletal disorders including but not limited to cancer-associated cachexia, muscular dystrophies and other degenerative muscle diseases, neuro-muscular disorders, rheumatoid arthritis, psoriatic arthritis, other inflammatory joint disease, crystal disease of the joint such as gout and pseudo-gout, degenerative arthritis, herniated disc disease, osteoporosis, ankylosing spondylitis, osteopetrosis, osteogenesis imperfect, spina bifida, scoliosis, spinal stenosis, traumatic spinal and brain injuries, neurological disorders such as neuro-generative disease and seizure disorders, Alzheimer's disease and other dementias, mental disorders including depression, bipolar disorders, schizophrenia, panic disorders, post-traumatic stress disorder (PTSD), concussion injuries that are either acute or chronic, chronic and acute infections whether bacterial, fungal, parasitic, helminthic, prion, protozoan such as malaria or babesiosis, infections with spirochetes, and generalized sepsis. In addition, our microRNA assays would be useful to assess intra-uterine disorders during pregnancy, and pregnancy associated conditions such as pre-eclampsia and eclampsia. Our measurements can be performed in all biological fluids: serum, plasma, urine, saliva, peritoneal fluid, cerebrospinal fluid, pericardial fluid, amniotic fluid, bile juice, pancreatic juice, tear fluid, maternal milk, galactorrhea fluid, and liquid and solid stool. The methods can further include distinguishing between pancreatic ductal adenocarcinoma and chronic pancreatitis.

In certain aspects, the microRNA of interest can be miR-10b.

In certain aspects, the methods do not require labeling or amplification of the microRNA of interest.

The methods of diagnosing a disease state in a subject can further include any features, structures, chemicals, or reagents described herein.

Biosensor Arrays

This disclosure also provides a biosensor array.

The biosensor arrays can include a plurality of the biosensors as described herein. Two or more of the biosensors can have sensitivity to different microRNAs.

The biosensor assays can further include any features, structures, chemicals, or reagents described herein.

Kits

This disclosure also provides a kit.

The kit can include a biosensor comprising a substrate having a substrate surface to which a plurality of localized surface plasmon resonance (LSPR) antennae are affixed, the LSPR antennae affixed via an affixation surface of the LSPR antenna, the LSPR antennae comprising a functional surface opposite the affixation surface; and a plurality of ssDNA adapted to functionalize the functional surface. In certain aspects, the plurality of ssDNA can have a sequence that is the sequence of ssDNA-10b or ssDNA-21.

In certain aspects, the kit can include a plurality of spacer molecules adapted to functionalize the functional surface.

The kits can further include any features, structures, chemicals, or reagents described herein.

Unless explicitly stated otherwise, all patents, patent applications, and non-patent literature cited herein is hereby incorporated by reference in its entirety. The present disclosure has been described in terms of one or more preferred aspects, and it should be appreciated that many equivalents, alternatives, variations, and modifications, aside from those expressly stated, are possible and within the scope of the disclosure.

EXAMPLES

Example 1

This disclosure describes for the first time the design and characterization of a regenerative, solid-state localized surface plasmon resonance (LSPR) sensor based on highly sensitive nanostructures (gold nanoprisms) that obviates the need for labels or amplification of the miRs. A direct hybridization approach has enabled the detection of sub-femtomolar concentration of miR-X (X=21 and 10b) in human plasma in pancreatic cancer patients. LSPR-based measurements showed that the miR levels measured directly in patient plasma were at least two-fold higher than following RNA extraction and quantification by reverse transcriptase-polymerase chain reaction. Through LSPR-based measurements, nearly four-fold higher concentrations of miR-10b than miR-21 in plasma of pancreatic cancer patients were shown. This disclosure provides that the highly sensitive and selective detection approach for assaying miRs in plasma can be applied to many cancer types and disease states, and should allow a rational approach for testing the utility of miRs as markers for early disease diagnosis and prognosis, which could allow for the design of effective individualized therapeutic approaches.

This disclosure provides for the first time the fabrication of label-free, solid-state plasmonic biosensors for miR detection. The biosensing involves the direct hybridization of PDAC-relevant miRs in plasma to their complementary single-stranded DNAs (HS-C6-ssDNA) that were functionalized on the surface of gold nanoprisms attached onto a glass substrate. This construct serves as a plasmonic biosensor through monitoring the LSPR dipole peak ($\lambda_{LSPR}$). This disclosure also demonstrates that the sensors are extremely specific in miR detection and that addition of DNA-RNA duplex cleaving enzymes regenerates the sensor, allowing for multiple uses without compromising sensing efficiency.

Fabrication of the Plasmonic Biosensor for miRs Detection.

FIG. 1 represents the schematic diagram of a solid-state, label-free plasmonic biosensor fabrication for miR detection. Chemically synthesized gold nanoprisms (FIG. 1a), which displayed their $\lambda_{LSPR}$ at ~797 nm upon attachment to solid substrate immersed in PBS buffer, were selected as nanoantennas for biosensor fabrication because: (1) their $\lambda_{LSPR}$ peak position (in the 700-900 nm wavelength range) is particularly suitable for biomolecule detection because of negligible background scattering and adsorption of endogeneous chromophores from physiological media such as blood and plasma, (2) they have strong electromagnetic (EM) field enhancement at the sharp tips, (3) they exhibits a strong LSPR response to small changes in their surrounding environment, (4) their atomically smooth surface allows formation of a self-assembled monolayer (SAM) of receptors with both a tightly packed lower layer of alkylthiols and a more loosely packed upper layer that provide the required space for duplex formation with complementary miR strands, (5) gold is nontoxic and stable under extreme physiological conditions, and (6) the gold-sulfur bond is very stable with thiol-modified receptors making a strong covalent bond with the gold surface. Above, the inventors have shown that a molecular sensor fabricated using an ~35 nm average edge-length gold nanoprisms displayed an unprecedentedly large 21 nm reversible shift upon a minor 0.6 nm increase in the thickness of the local dielectric environment. Therefore, gold nanoprisms of this size and geometry are unique and should provide extremely high sensitivity if plasmonic biosensors are fabricated using them, which is the scope of this disclosure. This disclosure provides the first example of LSPR-based miRs sensing in physiological media.

For detection and quantification, the selected targets were miR-21 and miR-10b, because it has been shown by locked nuclei acid-based in-situ hybridization that they are overexpressed in pancreatic cells (PCCs) within the tumor mass and that circulating miR-10b may serve as biomarker for diagnosis of PDAC. The sensing strategy was designed based on the hybridization between complementary probes (-C6-ssDNA-X, X=21 and 10b) attached to gold nanoprisms and their target miRs. The introduction of spacers in-between the DNA probes was included to reduce steric hindrance between the probes and the miRs and therefore enhance the hybridization and ultimately the sensitivity. As shown in FIG. 1$b$, poly (ethylene glycol)$_6$-thiols (PEG$_6$-SH) were used as spacers because they avoid non-specific adsorption of extraneous materials onto the nanoprism's surface and are not reactive towards miRs or other biological constituents present in plasma. Previously, the inventors demonstrated that functionalization of a nanoantenna's surface with an equal mole ratio of receptor and spacer provided the best sensitivity and lowest limit of detection (LOD). Therefore, a 1:1 ratio of HS-C6-ssDNA-X:PEG$_6$-SH was used to prepare the plasmonic biosensors (FIG. 1$b$). All the miRs and oligonucleotides sequences used in these studies are provided in Table 1.

UV-vis spectroscopy was used to monitor the changes in $\lambda_{LSPR}$ of the gold nanoprisms at different functionalization steps. The functionalization of substrate-bound nanoprisms with 1:1 ratio of HS-C6-ssDNA-21:PEG$_6$-SH resulted in an ~20.5±3.2 nm red-shift of $\lambda_{LSPR}$ as a result of the increase in local refractive index, which suggested the attachment of both molecular species onto the nanoprism's surface. These plasmonic biosensors were utilized for miR detection by incubating miR-21 (obtained from Sigma-Aldrich, USA) with concentration ranging from 100 nM to 50 fM in PBS buffer, 40% bovine plasma, or 40% human plasma solution. The $\lambda_{LSPR}$ response of gold nanoprisms for each miR-21 concentration was measured where the highest 18.8±1.9 nm $\lambda_{LSPR}$ red shift was observed for 100 nM miR-21 in PBS buffer. It is hypothesized that the $\lambda_{LSPR}$ red-shift is due to hybridization between ssDNA-21 and miR-21. It was found that the magnitude of the $\lambda_{LSPR}$ shift was concentration dependent, where 50 fM miR-21 caused a 3.7±0.3 nm $\lambda_{LSPR}$ red shift in PBS buffer. Table 2-4 summarizes the $\lambda_{LSPR}$ position for each concentration for the three different media. Evidently higher concentrations of miR-21 induced a larger number of ssDNA-21 strands to convert to DNA: RNA duplexes and consequently a larger change in the local refractive index around the nanoprisms, which results in a larger value of $\Delta\lambda_{LSPR}$.

The sensing mechanism is based on the hypothesis that the attachment of complementary target miRs to the plasmonic biosensor will shift the $\lambda_{LSPR}$ to higher wavelength (FIG. 1C). The total shift ($\Delta\lambda_{LSPR}$) depended on the miR concentration (FIG. 1D) and could be used to determine the limit of detection (LOD) (FIG. 1E). The LODs calculated for miR-21 in three different media were found to be in the range of 23-35 fM, which was more than 1000 and 3 fold lower than with the label-free microring resonator (150 fmol) and the nanopore based (100 fM) miR sensors, respectively. Importantly, these techniques detected miRs in PBS buffer whereas this disclosure provides for the first time a sensing approach in physiological media. Utilizing a direct hybridization-based detection approach, plasmonic biosensors were constructed with of -C6-ssDNA-10, while keeping other parameters constant. The LOD for miR-10b in the above media was determined over a concentration range from 100 nM to 50 fM. The average $\Delta\lambda_{LSPR}$ and LODs for miR-10b in three diverse media are shown in Table 5-7, and 9-10.

The principle underlying the actions of plasmonic biosensors is based on the successful hybridization between miRs and ssDNA attached to nanoprisms, where a higher number of duplex formations will result in a larger change in the refractive index surrounding the nanoprisms resulting in larger $\Delta\lambda_{LSPR}$ and higher sensitivity. Therefore, it would be expected that functionalization of gold nanoprisms with 100 percent HS-C6-ssDNA-X (without the PEG$_6$-thiol spacer) should reduce the LOD values because of steric hindrance and low attachment of miRs. To investigate this, gold nanoprisms were functionalized with 100 percent -C6-ssDNA-21 resulting in an ~15.0±1.8 nm $\lambda_{LSPR}$ red shift. The sensor was then incubated in different concentrations of miR-21 prepared in 40% human plasma. A ~9.6±1.1 nm red shift was observed for a 100 nM miR-21 concentrations and the lowest concentration that can be repeatedly detected was 10 pM from a $\Delta\lambda_{LSPR}$ of 3.4±0.5 nm. Table 8 contains the $\Delta\lambda_{LSPR}$ versus concentration data. Evidently, functionalization of the nanoprism's surface with 100 percent -C6-ssDNA-21 resulted in a 200-fold increase in detection limit in comparison to the 1:1 ratio -C6-ssDNA-21:PEG$_6$-SH mixed functionalization (Table 8). These experimental data further highlight the rationale for using spacers that increase the likelihood of hybridization. Fully covered gold nanoprisms were believed to be obtained when 100 percent -C6-ssDNA-21 was used for functionalization, which creates steric hindrance and does not allow the maximum number of miR-21 strands to come into close proximity with -C6-ssDNA-21 for hybridization. Therefore, not all the -C6-ssDNA-21 attached on the gold nanoprisms' surface was hybridized with miR-21 strands resulting in low sensing response. Thus, if a spacer was introduced between the -C6-ssDNA-21, it could allow the maximum -ssDNA-21 strands to be freely available for hybridization without any interference and ultimately enhance the sensitivity of the biosensor. Accordingly, a 1:1 mixed -C6-ssDNA-X:PEG$_6$-SH was used to functionalize the gold nanoprisms for the data collected herein, though it should be appreciated that different ratios can be suitable.

In order to confirm the hybridization of miR-X with -C6-ssDNA-X that resulted in the $\Delta\lambda_{LSPR}$, the enzyme RNase H was used to selectively cleave the DNA: RNA duplex and potentially reverse the $\Delta\lambda_{LSPR}$. Initially, the plasmonic biosensor for miR-21 was incubated in a 100 nM solution of miR-21, which resulted in red-shift of $\lambda_{LSPR}$ potentially reflecting hybridization. The biosensor was then immersed in 15 units of RNase H solution for 2 h. Afterwards the $\lambda_{LSPR}$ showed a blue shift and reverted back to its original position before miR-21 incubation. When the 1:1 ratio -C6-ssDNA-21:PEG$_6$-SH mixed functionalized biosensor was incubated with RNase H solution alone overnight, no noticeable change in $\lambda_{LSPR}$ value was observed. These experimental results validate the previous observation that the $\lambda_{LSPR}$ blue shift was due to the cleavage of heteroduplex done by RNase H. The biosensors were rinsed with RNase free water and again incubated in 100 nM miR-21 solution for rehybridization where an ~14 nm red shift of the $\lambda_{LSPR}$ was observed. These experiments confirm the working hypothesis that hybridization between the nanoprism's surface ligands (-C6-ssDNA-X) and the miR-X resulted in changes in the local dielectric environment around the nanoprisms causing wavelength shift. The $\lambda_{LSPR}$ responses were identical for several cycles due to hybridization and dehybridization of miR-21 over a period of 6 days. The $\lambda_{LSPR}$ peak shifts back and forth upon sensor regeneration with RNase H by cleaving DNA:RNA duplex and rehybridization after incubation into 100 nM miR-21 in 40% human plasma. After each dehybridization steps the plasmonic biosensors were thoroughly rinsed with PBS buffer to completely remove enzyme RNase H. The same experiments were done for the miR-10b biosensor and similar results were observed, underscoring the long-term stability of the sensors and their potential for being developed into cost-effective point of care diagnostic tools.

The hybridization takes place at the 5' end of -C6-ssDNA-21 and the 3' end of miR-21, which evidently increased the refractive index. Additionally such hybridization would also increase the thickness of the local dielectric environment of the nanoprisms. Together, a significantly large $\Delta\lambda_{LSPR}$ was generated for both miR-21 and miR-10b. Atomic force microscopy (AFM) analysis was conducted to characterize the plasmonic biosensors and also to verify the change in surface area caused by miR-21 incubation with mixed -C6-ssDNA-21 and $PEG_6$-SH-functioanlized gold nanoprisms. After analyzing 40 different nanoprisms an average $2.4 \times 10^{-15}$ m$^2$ increase in surface area was observed. Thus, attachment of miRs to plasmonic biosensors has increased the thickness of local dielectric environment around the gold nanoprisms and influenced their LSPR properties. Ultrasensitive refractive index-induced LSPR response of nanoprisms allows us to fabricate label-free plasmonic biosensor.

The successful implementation of plasmonic biosensors with real biological samples mandates documentation of their specificity towards target miRs since patient samples contain multiple miR species. The mixed functionalized (-C6-ssDNA-21 and $PEG_6$-SH) biosensors were incubated overnight in 40% human plasma solution containing 100 nM each miR-16, miR-122, miR-126, and miR-141, because these miRs are commonly present in human plasma. The $\lambda_{LSPR}$ response was measured before and after incubation and resulted in an ~2.5±0.3 nm $\lambda_{LSPR}$ red shift, which is within the instrument noise level and/or minor non-specific adsorption of extraneous materials present in human plasma. In another control experiment, gold nanoprisms attached as before to glass substrate were functionalized with 100% $PEG_6$-SH by incubating in 1 μM aqueous solution of the ligand, and after rinsing with large amounts of water, incubated in a 40% human plasma solution of 100 nM miR-21 for 12 h. This procedure resulted in only an ~0.9±0.7 nm $\lambda_{LSPR}$ red shift, confirming that the plasmonic biosensors disclosed herein are highly specific towards the target miRs.

Detection of miR Levels in Plasma from Pancreatic Cancer Patients.

Pancreatic cancer is the fourth-leading cause of cancer death in the United States with an annual mortality of nearly 40,000 and a dismal five-year survival rate of 6%. PDAC is characterized by chemotherapeutic resistance and by the absence of an effective screening procedure for early disease. It is generally accepted that early diagnosis could reduce mortality rates substantially and thus a non-invasive early PDAC test must be developed. Several miRs (such as miR-21, -10b, -103, -155, -196a, 210, and -221) were found to be overexpressed in PDAC. Given their resistance to degradation, plasma miRs have the potential to serve as biomarkers for the non-invasive diagnosis of PDAC. Previously, nanopore sensors were used to detect miRs in lung cancer patients, but to the best of the inventors' knowledge no sensors have been developed to date to detect PDAC-related miRs in human plasma.

Utilizing the plasmonic biosensors miR-21 and miR-10b were detected in plasma from PDAC patients. Plasma samples were collected from six patients and six normal control subjects. Total plasma RNAs including miRs were extracted from 100 μL of each plasma sample using a TRIZOL® kit (available commercially from Life Technologies, Carlsbad, Calif.), with a final elution volume of 28 μL. Next, 14 μL volumes were used for miR quantification by the plasmonic biosensor and the remaining 14 μL were used in the qRT-PCR assay. The plasmonic biosensors were fabricated as described before for both miR-21 and miR-10b detection. The extracted human miR-21 or miR-10b samples were diluted in PBS buffer and incubated with the biosensors were for 12 h, followed by rinsing with PBS buffer and measurement of the $\lambda_{LSPR}$ response in PBS buffer. The observed $\lambda_{LSPR}$ shift for each miR-21 and miR-10b sample was converted into the corresponding concentration using the calibration curve derived for miR-21 or 10b under optimized conditions and compared with the value from normal human patients (Tables 11-14). The concentrations of miR-21 and miR-10b determined from plasmonic biosensors were also compared with the values obtained from the qRT-PCR assay (Tables 15-18). Importantly, for the first time, through a label-free technique this disclosure has shown that miR-10b concentration is nearly four-fold higher than the miR-21 level in patient samples. Inasmuch as both mirR-21 and miR-10b are overexpressed in PDAC, it is possible that miR-10b is released more efficiently by pancreatic cancer cells than miR-21, allowing it to achieve higher levels in the circulation. It is therefore possible that miR-10b levels are also increased within the pancreatic tumor microenvironment, where it could be acting to enhance PDAC biological aggressiveness.

miR-21 levels were also detected directly in human plasma samples collected from PDAC patients without RNAs extraction. Thus, 50 μL human plasma samples were obtained from the six-pancreatic cancer patients and diluted in PBS buffer followed by incubation with the plasmonic biosensors for 12 h. The $\lambda_{LSPR}$ response of each sample was measured through UV-vis spectroscopy and showed a steady increase in concentration from sample 6 to 1 (Table 19-20). Both plasmonic biosensor and qRT-PCR results indicated that miR-10b levels were higher in PDAC patients compare to normal human and that the levels of miR-21 and miR-10b can be quantified with high accuracy using the gold nanoprisms-based plasmonic biosensor without any modification, amplification, or labeling. Importantly, the miR-21 concentration in extracted samples was at least two-fold lower than in the pure plasma samples. It is believed that this is due to degradation and/or loss of miRs during the RNA extraction processes. Therefore, most widely used qRT-PCR method to determine the concentration of miRs in patients may not accurately represent the actual concentration. This limitation and imprecise quantification can be avoided by using the newly developed plasmonic biosensors, which provide a unique opportunity as potential diagnostic and prognostic markers in PDACs and other cancers.

Conclusion. A plasmonic biosensor that was able to detect PDAC relevant miRs in human plasma without using RNAs extraction was designed, fabricated, and characterized, which opens a new avenue for the direct detection and quantification of miR levels in clinical samples without any form of sample preparation. To the inventors' knowledge, this is the first LSPR-based, label-free, direct hybridization method for miR detection, which eliminates all the current drawbacks such as labeling, tagging, amplification, use of highly toxic chemicals, and further modification of the sensor. Furthermore, it vastly simplifies the detection approach without requiring detailed knowledge of the electron or energy transfer processes involved as in other more complicated techniques. Additionally, this ultrasensitive, plasmonic-based, direct hybridization-controlled detection approach is applicable to any type of miRs that are relevant to various diseases. It was found that the plasmonic biosensor can be regenerated through several cycles and is stable for several days without compromising its sensitivity and selectivity, which should enable the development of simple, cost-effective tools for the early detection of miRs and thus facilitate the early diagnosis of various cancers. Finally, the large EM-field enhancement at the nanoprism's sharp tips may enhance the Raman scattering intensity of the analytes. In theory, therefore, nanoprisms can be developed for use as an effective substrate for surface-enhanced Raman spectroscopy-based detection and quantification of multiple miRs simultaneously through integration of their spectral characteristic with the $\lambda_{LSPR}$ shifts.

Materials and methods. All synthetic DNA probes and microRNAs were purchased from Sigma-Aldrich (USA). PBS buffer prepared with RNase-free water was used to dilute oligonucleotides and miRs solutions. Patient plasma was obtained from the Indiana University Simon Cancer Center Solid Tissue Bank (Indianapolis, Ind.).

Fabrication of LSPR-based miR sensors and detection. The gold nanoprism-based miR sensors were designed using a published procedure (set forth in Joshi, G. K. et al. Ultrasensitive Photorevsersible Molecular Sensors of Azobenzene Functionalized Plasmonic Nanoantennas. *Nano Letters* 14, 532-540 (2014)) with modification. The attachment of gold nanoprisms on silanized glass substrates is described below. The substrate-bound nanoprisms were incubated in PBS buffer solution containing 1 μM each of HS-C6-ssDNA-X and PEG$_6$-SH overnight and rinsed with PBS buffer. The initial LSPR peak position of each sensing platform was determined using UV-visible spectroscopy in PBS buffer and then was incubated in the different concentrations of miR solutions, e.g., either in PBS buffer, 40% bovine plasma, or 40% human plasma for 12 h at room temperature. The plasmonic biosensors were thoroughly washed with PBS buffer to remove any non-specifically adsorbed species. The miR bound biosensor was then placed in PBS buffer for 10 min before the LSPR peak position was determined. For UV-vis extinction spectra measurement, one particular solvent was chosen to avoid the solvent dielectric constant effect, which is known to shift the LSPR peak.

Total RNA extraction and quantification of microRNA by qRT-PCR. Total RNA was isolated from plasma samples that were obtained from the Indiana University Simon Cancer Center Solid Tissue Bank (Indianapolis, Ind., USA) using Trizol® LS reagent (Life Technologies, Carlsbad, Calif., USA). cDNA was generated using 10 ng of RNA and miR-10b, miR-21, or miR-425-5p RT primers and a miR reverse transcription kit (Life Technologies) as per the manufacturer's recommendations. Quantitative PCR (qPCR) was performed using Taqman® miR expression assay reagents. Expression levels as determined by qPCR were normalized to miR-425-5p, since this miR was expressed at similar levels in all samples and exhibited <1 cycle threshold (Ct) difference across all samples. After normalization to miR-425-5p (ΔCt), the ΔCt values for miRs in controls were averaged and subtracted from the ΔCt values of each individual sample (ΔΔCt). miR levels were then calculated using the $2^{-\Delta\Delta Ct}$ method, as described in Livak, K. J. & Schmittgen, T. D. Analysis of Relative Gene Expression Data Using Real-Time Quantitative PCT and the 2-ΔΔCT Method. *Methods*. 25, 402-408 (2001).

Chemicals. Chloro(triethylphosphine) gold (I) (Et$_3$PAuCl, 97%), poly(methylhydrosiloxane) (PMHS, Mn=1700-3300), trioctylamine (TOA, 98%), ACS grade acetonitrile (CH$_3$CN, 99.9%), methanol (99.8%), human plasma (contains 4% trisodium citrate and tested for HIV, hepatitis C and hepatitis B), thiol modified ssDNAs, microRNAs (miRs), Tris-base, magnesium chloride (MgCl$_2$), potassium chloride (KCl), ethylenediaminetetraaceticacid (EDTA), and bovine plasma (contain 3.8% trisodium citrate as an anticoagulant) were purchased from Sigma Aldrich and were used as received. (3-mercaptopropyl)-triethoxysilane (MPTES, 94%) was purchased from Alfa Aesar, and ethanol (alcohol 200 proof) was purchased from Decon labs. RNase H enzyme and RNase H reaction buffer were purchased from New England BioLabs Inc. RNase free sterile water was obtained from Baxter Healthcare Corporation. 1,4-Dithiothreitol (DTT) was purchased from Roche Diagnostics. Hydrochloric acid (HCl), sodium chloride (NaCl, 99.5%), sodium phosphate monobasic monohydrate (NaH$_2$PO$_4$.H$_2$O, >98%), sodium phosphate dibasic anhydrous (Na$_2$HPO$_4$), and the glass coverslips were purchased from Fisher Scientific. RBS 35 Detergent was obtained from Thermo Scientific and used as received. The super Sharpe silicon scanning probes (SSS-NCHR) for atomic force microscopy measurements were purchased from nanosensors. All water was purified using a Thermo Scientific Barnstead™ Nanopure™ system. Thiol modified oligonucleotides and all miRs were stored at −20° C. RNase free sterile water was used to prepare the PBS buffer solution. Polyethylene glycol thiol (PEG$_6$-SH) was synthesized in the laboratory using published procedures (Lawrence, K. N.; Johnson, M. A.; Dolai, S.; Kumbhar, A.; Sardar, R. Solvent-like ligand-coated ultrasmall cadmium selenide nanocrystals: strong electronic coupling in a self-organized assembly. *Nanoscale* 2015, 7, 11667-11677).

Nucleic Acid Sequences

In this example, the following oligonuclotide and miR strands were used: ssDNA-21 (SEQ ID NO: 1); ssDNA-10b (SEQ ID NO: 2); target miR-21 (SEQ ID NO: 3); target miR-10b (SEQ ID NO: 4); miR-16 (SEQ ID NO: 5); miR-126 (SEQ ID NO: 6); miR-141 (SEQ ID NO: 7); and miR-122 (SEQ ID NO: 8).

TABLE 1

Summary of oligonucleotide and miR strands used in this Example.

| | strand name | sequence | MW (kDa) | modification |
|---|---|---|---|---|
| 1 | ssDNA-21 | 5'-TCAACATCAGTCTGATAAGCTA-3' | 6.7 | 5'thiol-$C_6$ |
| 2 | ssDNA-10b | 5'-CACAAATTCGGTTCTACAGGGTA-3' | 7.1 | 5'thiol-$C_6$ |
| 3 | target miR-21 | 5'-UAGCUUAUCAGACUGAUGUUGA-3' | 6.6 | none |
| 4 | target miR-10b | 5'-UACCCUGUAGAACCGAAUUUGUG-3' | 7.0 | none |
| 5 | miR-16 | 5'-UAGCAGCACGUAAAUAUUGGCG-3' | 7.1 | none |
| 6 | miR-126 | 5'-CAUUAUUACUUUUGGUACGCG-3' | 6.3 | none |
| 7 | miR-141 | 5'-UAACACUGUCUGGUAAAGAUGG-3' | 6.7 | none |
| 8 | miR-122 | 5'-UGGAGUGUGACAAUGGUGUUUG-3' | 6.8 | none |

Spectroscopy and Microscopy Characterization. Absorption and extinction spectra in the range of 300-1100 nm were collected with a Varian Cary® 50 Scan UV-visible spectrophotometer using 1 cm quartz cuvette. All the absorbance spectra were collected using 0.3 mL of reaction solution diluted in 2.0 mL of acetonitrile. Acetonitrile was used as a background for these measurements, and the background was run before collecting the absorbance spectra. All extinction spectra were measured in PBS buffer (pH 7.2) at room temperature unless otherwise specified. Here, the blank silanized glass coverslips immersed in PBS buffer were used as a background and the background was run before collecting the extinction spectra. The chemically synthesized gold nanoprisms attached onto the silanized glass coverslips were characterized after each functionalization step through atomic force microscopy (AFM). All AFM measurements were conducted in air utilizing tapping mode on a Bruker BioScope Catalyst with SSS-NCHR probes (Nanosensors) (tip radius ~2 nm). Images were collected using a tip velocity of 1 mM/s over 1-2 uM scan sizes of three to five regions of each samples. All microscopy files were plain fitted and 2D fitted using Gwyddion. Also using the software, the individual nanoprisms were selected and analyzed to determine their surface area and height profiles.

Synthesis of Gold Nanoprisms.

Gold nanoprisms were chemically synthesized according to a previously developed procedure with minor modification. Specifically, $Et_3PAu(I)Cl$ (8 mg, 0.02 mmol) was dissolved in 5 mL of acetonitrile and allowed to stir for 5 min at room temperature. 0.085 mL of TOA and 0.3 mL of PMHS were mixed with 1 mL of acetonitrile in a vial and injected into the above solution. The reaction mixture was then allowed to heat at 40° C. The solution color started to change from colorless to pink, purple, blue and at this point 14 mL acetonitrile was added to the reaction and the reaction was allowed to run for another 130 min, which resulted in a dark blue solution indicating the formation of nanoprisms with a stable absorbance dipole peak at 780 nm in acetonitrile. The solution was then removed from heat, centrifuged at 7000 rpm for 2 minutes, and used for the biosensor fabrication.

Silanization of Glass Coverslips and Attachment of Nanoprisms.

The glass coverslips (supporting substrates) were functionalized according to previously published procedures. Glass coverslips were immersed in a 20% (v/v) aqueous RBS 35 detergent solution at 90° C. for 30 min, followed by 5 min of sonication. After thoroughly rinsing the coverslips with nanopure water, they were placed in a solution of conc. hydrochloric acid and methanol (1:1 v/v) for 30 min. The coverslips were then rinsed several times with nanopure water and dried in a vacuum oven at 60° C. overnight then incubated in a solution of 10% MPTES in ethanol for 30 min, sonicated for 5 min, and rinsed with anhydrous ethanol. The coverslips were rinsed with ethanol by sonicating them in ethanol, which was repeated at least 5 times. After rinsing, the coverslips were baked in a vacuum oven at 120° C. for 3 hours. The MPTES-functionalized coverslips (substrate) were then incubated for 30 min in a freshly prepared gold nanoprisms reaction solution. After incubation, the substrate-bound gold nanoprisms were rinsed with ethanol, dried under nitrogen flow, and stored under nitrogen at 4° C.

Preparation of microRNA Sensors.

As the reaction solution contains other non-prismatic nanostructures, a tape-cleaning procedure was performed on the substrate bound gold nanoprisms platform to remove non-prismatic nanostructures. Tape cleaning was done by placing the adhesive (scotch) tape onto the gold nanoprisms attached supporting substrate, gently pressed down with a finger, and slowly removed at a 90° angle. The nanoprisms containing supporting substrates were then incubated into PBS buffer solution containing HS-C6-ssDNA-X: $PEG_6$-SH (1 µM each) for overnight. Next, the HS-C6-ssDNA-X: $PEG_6$-SH functionalized gold nanoprisms (plasmonic biosensor for miR-X) were rinsed with copious amount of PBS buffer to remove loosely bound reactants and biosensors then further utilized for miR-X sensing.

Detection of Synthetic microRNAs in Either PBS (pH=7.4) buffer, 40% Bovine Plasma, and 40% Human Plasma.

Different concentrations of synthetic miR-X solutions were prepared either in PBS buffer, or 40% bovine plasma, or 40% human plasma. The plasmonic biosensors prepared in above were then incubated in the different concentrations of miR-X solutions in above-mentioned physiological media overnight. The miR-X bound biosensors were then rinsed with PBS buffer to remove any non-specifically adsorbed species and placed in PBS buffer for 10 min to equilibrate. Extinction spectra were collected in PBS buffer.

Confirming DNA-RNA Duplex and Regeneration of the Sensors.

In order to confirm the miR-X hybridization with the plasmonic biosensor, hybridized, dehybridized, and rehybridized with target miR-X were investigated. RNase H enzyme that selectively cleaves the DNA: RNA duplex was used for dehybridization studies. The plasmonic biosensor for miR-21 was allowed to hybridize in 100 nM of miR-21 in 40% human plasma overnight. The plasmonic biosensor's response ($\lambda_{LSPR}$) was measured before and after the incubation in miR-21. To confirm that the $\lambda_{LSPR}$ shift observed after miR-21 incubation was indeed due to its hybridization with the gold nanoprisms' surface bound HS-C$_6$-ssDNA-21 probe, the miR-21 bound plasmonic biosensor was immersed in 15 units of RNase H suspended 20 mM of Tris-HCl (pH 7.4), 20 mM KCl, 10 mM MgCl$_2$, 0.1 mM EDTA, and 0.1 mM DTT solution for 2 h, then rinsed with PBS buffer and the $\lambda_{LSPR}$ shift was measured. The plasmonic biosensor was further incubated in 100 nM miR-21 solutions of 40% human plasma overnight. The same process was repeated for several cycles to confirm the stability and the regeneration of the plasmonic biosensor. Control experiments without hybridized miR-21 were also performed, where the plasmonic biosensor for miR-21 was immersed in RNase H containing reaction solution for overnight followed by rinsing with PBS buffer. The biosensor was further immersed in 100 nM miR-21 solutions in 40% human plasma overnight, rinsed with PBS buffer and the $\Delta\lambda_{LSPR}$ shift was measured.

microRNA Detection of Total RNAs Extracted and Purified Pancreatic Cancer Patients plasma in PBS Buffer.

The plasma samples were collected from six PDAC patients and six normal human samples. Total plasma RNAs including miRs were extracted from 100 μL of each plasma sample using TRIZOL® kit, with a final elution volume of 28 μL. 14 μL volumes were used for the miR quantification using the plasmonic biosensor and the remaining 14 μL were used for qRT-PCR assay to confirms the miR levels in each sample. 14 μL volumes were diluted in 786 μL of PBS buffer and the prepared plasmonic biosensor for miR-X was incubated in that solution overnight, followed by rinsing with PBS buffer and $\lambda_{LSPR}$ measurements in PBS buffer.

microRNA Detection in Human Plasma Collected from Pancreatic Cancer Patients without RNAs Extraction.

50 μL of human plasma samples were obtained from the six PDAC patients. 50 μL of aliquot was diluted with 750 μL of PBS buffer and the plasmonic biosensor prepared for miR-21 was immobilized in these solutions overnight and then rinsed with PBS buffer. $\lambda_{LSPR}$ responses of the biosensor for each plasma sample were measured in PBS buffer. The experiment was repeated at least four times and the obtained $\lambda_{LSPR}$ responses were further correlated with the results obtained for same samples through qRT-PCR assay.

Data Processing and Statistical Analysis.

All measurements for synthetic miRs were repeated at least five times, and the PDAC patients' samples were measured at least four times. The obtained responses were reported as mean±S.D. for each step. The $\lambda_{LSPR}$ peak position was determined by taking the maxima of the dipole peak position in the UV-visible spectra. The $\Delta\lambda_{LSPR}$ was derived by taking the difference between the plasmonic biosensors response towards the $\lambda_{LSPR}$ before and after hybridization with the standard target miR-X to the functionalized surface ssDNA-X probe. All UV-visible spectra and the calibration curves were plotted using the MS-Excel. The extinction spectra were adjusted to the highest extinction value to visualize the $\lambda_{LSPR}$ shift. The LOD was calculated by measuring the $\Delta\lambda_{LSPR}$ for the blank and then obtained the Z (mean+3σ) value and convert the Z value into the relative concentration using the calibration curve. Here, the blank measurement was the $\lambda_{LSPR}$ response for HS-C6-ssDNA-X: PEG$_6$-SH functionalized gold nanoprisms before and after overnight incubation in the relative physical media without target miR-X. The relative concentration for miR-X for total RNAs extracted from PDAC patient plasma and normal human plasma samples were derived from the calibration curve obtained for synthetic miR-X in PBS buffer. However, the calibration curve for synthetic miR-21 in 40% human plasma was used to derive the relative concentrations for miR-21 in PDAC patients' plasma without any extraction.

Experimental Data to Develop Calibration Curves

TABLE 2

$\lambda_{LSPR}$ responses from plasmonic biosensor for different concentrations of miR-21 in PBS buffer.

| Sensor # | $\lambda_{LSPR}$ (nm) for HS-C6-ssDNA-21: PEG$_6$SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 818 | 838 | 20.0 | | |
| 2 | 817 | 833 | 16.0 | | |
| 3 | 819 | 838 | 19.0 | 18.8 | 1.9 |
| 4 | 821 | 839 | 18.0 | | |
| 5 | 820 | 841 | 21.0 | | |
| | | 10 nM | | | |
| 1 | 814 | 830 | 16.0 | | |
| 2 | 819 | 832 | 13.0 | | |
| 3 | 818 | 834 | 16.0 | 13.6 | 2.5 |
| 4 | 815 | 828 | 13.0 | | |
| 5 | 817 | 827 | 10.0 | | |
| | | 1 nM | | | |
| 1 | 819 | 831 | 12.0 | | |
| 2 | 816 | 826 | 10.0 | | |
| 3 | 821 | 833 | 12.0 | 11.8 | 1.1 |
| 4 | 816 | 829 | 13.0 | | |
| 5 | 818 | 830 | 12.0 | | |
| | | 0.1 nM | | | |
| 1 | 816 | 825 | 9.0 | | |
| 2 | 820 | 829 | 9.0 | | |
| 3 | 815 | 823 | 8.0 | 8.8 | 0.8 |
| 4 | 818 | 828 | 10.0 | | |
| 5 | 819 | 827 | 8.0 | | |
| | | 0.01 nM | | | |
| 1 | 817 | 827 | 10.0 | | |
| 2 | 818 | 826 | 8.0 | | |
| 3 | 820 | 828 | 8.0 | 8.4 | 1.1 |
| 4 | 819 | 828 | 9.0 | | |
| 5 | 818 | 825 | 7.0 | | |
| | | 0.001 nM | | | |
| 1 | 820 | 826 | 6.0 | | |
| 2 | 819 | 825 | 6.0 | | |
| 3 | 815 | 822 | 7.0 | 6.2 | 0.8 |
| 4 | 815 | 820 | 5.0 | | |
| 5 | 817 | 824 | 7.0 | | |
| | | 0.0001 nM | | | |
| 1 | 818 | 823 | 5.0 | | |
| 2 | 817 | 822 | 5.0 | | |
| 3 | 820 | 824 | 4.0 | 4.8 | 0.4 |
| 4 | 819 | 824 | 5.0 | | |
| 5 | 818 | 823 | 5.0 | | |

TABLE 2-continued $\lambda_{LSPR}$ responses from plasmonic biosensor for different concentrations of miR-21 in PBS buffer.

| Sensor # | $\lambda_{LSPR}$ (nm) for HS-C6-ssDNA-21: PEG6SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 0.00005 nM | | | |
| 1 | 816 | 819.7 | 3.7 | | |
| 2 | 820 | 824 | 4.0 | | |
| 3 | 821 | 824.5 | 3.5 | 3.7 | 0.3 |
| 4 | 815 | 819 | 4.0 | | |
| 5 | 817 | 820.4 | 3.4 | | |

TABLE 3

$\lambda_{LSPR}$ responses from plasmonic biosensor for different concentrations of miR-21 in 40% human plasma.

| Sensor # | $\lambda_{LSPR}$ (nm) for HS-C6-ssDNA-21: PEG6SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 823 | 836 | 13.0 | | |
| 2 | 816 | 828 | 12.0 | | |
| 3 | 820 | 832 | 12.0 | 12.6 | 0.9 |
| 4 | 815 | 829 | 14.0 | | |
| 5 | 822 | 834 | 12.0 | | |
| | | 10 nM | | | |
| 1 | 817 | 828 | 11.0 | | |
| 2 | 815 | 825 | 10.0 | | |
| 3 | 814 | 824 | 10.0 | 10.0 | 0.7 |
| 4 | 818 | 827 | 9.0 | | |
| 5 | 815 | 825 | 10.0 | | |
| | | 1 nM | | | |
| 1 | 815 | 824 | 9.0 | | |
| 2 | 816 | 824 | 8.0 | | |
| 3 | 815 | 823 | 8.0 | 8.4 | 0.5 |
| 4 | 814 | 823 | 9.0 | | |
| 5 | 813 | 821 | 8.0 | | |
| | | 0.1 nM | | | |
| 1 | 815 | 822 | 7.0 | | |
| 2 | 817 | 825 | 8.0 | | |
| 3 | 814 | 821 | 7.0 | 7.6 | 0.5 |
| 4 | 813 | 821 | 8.0 | | |
| 5 | 815 | 823 | 8.0 | | |
| | | 0.01 nM | | | |
| 1 | 816 | 822 | 6.0 | | |
| 2 | 814 | 821 | 7.0 | | |
| 3 | 815 | 821 | 6.0 | 6.6 | 0.5 |
| 4 | 814 | 821 | 7.0 | | |
| 5 | 813 | 820 | 7.0 | | |
| | | 0.001 nM | | | |
| 1 | 815 | 821 | 6.0 | | |
| 2 | 816 | 822 | 6.0 | | |
| 3 | 815 | 820 | 5.0 | 5.2 | 0.8 |
| 4 | 815 | 820 | 5.0 | | |
| 5 | 814 | 818 | 4.0 | | |

TABLE 3-continued $\lambda_{LSPR}$ responses from plasmonic biosensor for different concentrations of miR-21 in 40% human plasma.

| Sensor # | $\lambda_{LSPR}$ (nm) for HS-C6-ssDNA-21: PEG6SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 0.0001 nM | | | |
| 1 | 816 | 821 | 5.0 | | |
| 2 | 814 | 818 | 4.0 | | |
| 3 | 815 | 819 | 4.0 | 4.1 | 0.6 |
| 4 | 817 | 820.5 | 3.5 | | |
| 5 | 814 | 818 | 4.0 | | |
| | | 0.00005 nM | | | |
| 1 | 816 | 819 | 3.0 | | |
| 2 | 815 | 819 | 4.0 | | |
| 3 | 814 | 817 | 3.0 | 3.4 | 0.5 |
| 4 | 813 | 817 | 4.0 | | |
| 5 | 815 | 818 | 3.0 | | |

TABLE 4

$\lambda_{LSPR}$ responses from plasmonic biosensor for different concentrations of miR-21 in 40% bovine plasma.

| Sensor # | $\lambda_{LSPR}$ (nm) for HS-C6-ssDNA-21: PEG6SH functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 818 | 832 | 14.0 | | |
| 2 | 819 | 835 | 16.0 | | |
| 3 | 815 | 827 | 12.0 | 14.0 | 2.0 |
| 4 | 818 | 834 | 16.0 | | |
| 5 | 815 | 827 | 12.0 | | |
| | | 10 nM | | | |
| 1 | 819 | 830 | 11.0 | | |
| 2 | 818 | 827 | 9.0 | | |
| 3 | 818 | 828 | 10.0 | 10.2 | 0.8 |
| 4 | 815 | 826 | 11.0 | | |
| 5 | 820 | 830 | 10.0 | | |
| | | 1 nM | | | |
| 1 | 819 | 829 | 10.0 | | |
| 2 | 818 | 826 | 8.0 | | |
| 3 | 821 | 827 | 6.0 | 8.0 | 1.4 |
| 4 | 816 | 824 | 8.0 | | |
| 5 | 815 | 823 | 8.0 | | |
| | | 0.1 nM | | | |
| 1 | 816 | 824 | 8.0 | | |
| 2 | 818 | 827 | 9.0 | | |
| 3 | 815 | 821 | 6.0 | 7.6 | 1.1 |
| 4 | 819 | 826 | 7.0 | | |
| 5 | 819 | 827 | 8.0 | | |
| | | 0.01 nM | | | |
| 1 | 820 | 827 | 7.0 | | |
| 2 | 816 | 821 | 5.0 | | |
| 3 | 820 | 826 | 6.0 | 6.2 | 0.8 |
| 4 | 821 | 827 | 6.0 | | |
| 5 | 818 | 825 | 7.0 | | |

TABLE 4-continued

λ$_{LSPR}$ responses from plasmonic biosensor for different concentrations of miR-21 in 40% bovine plasma.

| Sensor # | λ$_{LSPR}$ (nm) for HS-C6-ssDNA-21: PEG$_6$SH functionalized gold nanoprisms | λ$_{LSPR}$ (nm) after incubation in different concentrations of miR-21 | Δλ$_{LSPR}$ (nm) | Average Δλ$_{LSPR}$ (nm) | S.D. |
|---|---|---|---|---|---|
| \multicolumn{6}{c}{0.001 nM} | | | | | |
| 1 | 820 | 825 | 5.0 | | |
| 2 | 818 | 824 | 6.0 | | |
| 3 | 817 | 821 | 4.0 | 4.6 | 0.9 |
| 4 | 816 | 820 | 4.0 | | |
| 5 | 817 | 821 | 4.0 | | |
| \multicolumn{6}{c}{0.0001 nM} | | | | | |
| 1 | 816 | 819 | 3.0 | | |
| 2 | 817 | 820.6 | 3.6 | | |
| 3 | 815 | 818.4 | 3.4 | 3.4 | 0.3 |
| 4 | 816 | 819.7 | 3.7 | | |
| 5 | 818 | 821.4 | 3.4 | | |

TABLE 5

λ$_{LSPR}$ responses from plasmonic biosensor for different concentrations of miR-10b in PBS buffer.

| Sensor # | λ$_{LSPR}$ (nm) for HS-C6-ssDNA-10b: PEG$_6$SH functionalized gold nanoprisms | λ$_{LSPR}$ (nm) after incubation in different concentrations of miR-10b | Δλ$_{LSPR}$ (nm) | Average Δλ$_{LSPR}$ (nm) | S.D. |
|---|---|---|---|---|---|
| \multicolumn{6}{c}{100 nM} | | | | | |
| 1 | 820 | 835 | 15.0 | | |
| 2 | 823 | 837 | 14.0 | | |
| 3 | 821 | 836 | 15.0 | 15.2 | 0.8 |
| 4 | 824 | 840 | 16.0 | | |
| 5 | 818 | 834 | 16.0 | | |
| \multicolumn{6}{c}{10 nM} | | | | | |
| 1 | 822 | 833 | 11.0 | | |
| 2 | 820 | 832 | 12.0 | | |
| 3 | 821 | 832 | 11.0 | 11.4 | 1.1 |
| 4 | 820 | 830 | 10.0 | | |
| 5 | 823 | 836 | 13.0 | | |
| \multicolumn{6}{c}{1 nM} | | | | | |
| 1 | 818 | 828 | 10.0 | | |
| 2 | 820 | 831 | 11.0 | | |
| 3 | 824 | 834 | 10.0 | 10.4 | 0.5 |
| 4 | 818 | 828 | 10.0 | | |
| 5 | 819 | 830 | 11.0 | | |
| \multicolumn{6}{c}{0.1 nM} | | | | | |
| 1 | 820 | 829 | 9.0 | | |
| 2 | 818 | 827 | 9.0 | | |
| 3 | 822 | 830 | 8.0 | 8.6 | 0.5 |
| 4 | 821 | 829 | 8.0 | | |
| 5 | 819 | 828 | 9.0 | | |
| \multicolumn{6}{c}{0.01 nM} | | | | | |
| 1 | 820 | 828 | 8.0 | | |
| 2 | 819 | 825 | 6.0 | | |
| 3 | 824 | 831 | 7.0 | 7.2 | 1.3 |
| 4 | 821 | 830 | 9.0 | | |
| 5 | 820 | 826 | 6.0 | | |

TABLE 5-continued

λ$_{LSPR}$ responses from plasmonic biosensor for different concentrations of miR-10b in PBS buffer.

| Sensor # | λ$_{LSPR}$ (nm) for HS-C6-ssDNA-10b: PEG$_6$SH functionalized gold nanoprisms | λ$_{LSPR}$ (nm) after incubation in different concentrations of miR-10b | Δλ$_{LSPR}$ (nm) | Average Δλ$_{LSPR}$ (nm) | S.D. |
|---|---|---|---|---|---|
| \multicolumn{6}{c}{0.001 nM} | | | | | |
| 1 | 821 | 828 | 7.0 | | |
| 2 | 820 | 826 | 6.0 | | |
| 3 | 819 | 827 | 8.0 | 6.2 | 1.3 |
| 4 | 820 | 825 | 5.0 | | |
| 5 | 819 | 824 | 5.0 | | |
| \multicolumn{6}{c}{0.0001 nM} | | | | | |
| 1 | 819 | 824 | 5.0 | | |
| 2 | 820 | 824 | 4.0 | | |
| 3 | 822 | 827 | 5.0 | 4.0 | 1.0 |
| 4 | 819 | 822 | 3.0 | | |
| 5 | 818 | 821 | 3.0 | | |
| \multicolumn{6}{c}{0.00005 nM} | | | | | |
| 1 | 815 | 818 | 3 | | |
| 2 | 820 | 823.3 | 3.3 | | |
| 3 | 819 | 821.6 | 2.6 | 3.0 | 0.3 |
| 4 | 817 | 820 | 3 | | |
| 5 | 821 | 824 | 3 | | |

TABLE 6

λ$_{LSPR}$ responses from plasmonic biosensor for different concentrations of miR-10b in 40% human plasma.

| Sensor # | λ$_{LSPR}$ (nm) for HS-C6-ssDNA-10b: PEG$_6$SH functionalized gold nanoprisms | λ$_{LSPR}$ (nm) after incubation in different concentrations of miR-10b | Δλ$_{LSPR}$ (nm) | Average Δλ$_{LSPR}$ (nm) | S.D. |
|---|---|---|---|---|---|
| \multicolumn{6}{c}{100 nM} | | | | | |
| 1 | 822 | 835 | 13.0 | | |
| 2 | 820 | 831 | 11.0 | | |
| 3 | 817 | 829 | 12.0 | 12.2 | 0.8 |
| 4 | 821 | 833 | 12.0 | | |
| 5 | 819 | 832 | 13.0 | | |
| \multicolumn{6}{c}{10 nM} | | | | | |
| 1 | 820 | 830 | 10.0 | | |
| 2 | 818 | 830 | 12.0 | | |
| 3 | 816 | 827 | 11.0 | 10.4 | 1.1 |
| 4 | 820 | 830 | 10.0 | | |
| 5 | 815 | 824 | 9.0 | | |
| \multicolumn{6}{c}{1 nM} | | | | | |
| 1 | 821 | 830 | 9.0 | | |
| 2 | 816 | 824 | 8.0 | | |
| 3 | 820 | 828 | 8.0 | 8.2 | 0.4 |
| 4 | 815 | 823 | 8.0 | | |
| 5 | 817 | 825 | 8.0 | | |
| \multicolumn{6}{c}{0.1 nM} | | | | | |
| 1 | 820 | 828 | 8.0 | | |
| 2 | 820 | 827 | 7.0 | | |
| 3 | 816 | 824 | 8.0 | 7.2 | 0.8 |
| 4 | 818 | 825 | 7.0 | | |
| 5 | 817 | 823 | 6.0 | | |

TABLE 6-continued $\lambda_{LSPR}$ responses from plasmonic biosensor for different concentrations of miR-10b in 40% human plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 0.01 nM | | | |
| 1 | 820 | 827 | 7.0 | | |
| 2 | 817 | 823 | 6.0 | | |
| 3 | 823 | 830 | 7.0 | 6.4 | 0.5 |
| 4 | 815 | 821 | 6.0 | | |
| 5 | 822 | 828 | 6.0 | | |
| | | 0.001 nM | | | |
| 1 | 820 | 826 | 6.0 | | |
| 2 | 818 | 824 | 6.0 | | |
| 3 | 815 | 820 | 5.0 | 5.4 | 0.5 |
| 4 | 823 | 828 | 5.0 | | |
| 5 | 820 | 825 | 5.0 | | |
| | | 0.0001 nM | | | |
| 1 | 820 | 824 | 4.0 | | |
| 2 | 817 | 821 | 4.0 | | |
| 3 | 822 | 825.5 | 3.5 | 4.1 | 0.4 |
| 4 | 817 | 821.5 | 4.5 | | |
| 5 | 818 | 822.5 | 4.5 | | |
| | | 0.00005 nM | | | |
| 1 | 817 | 820.5 | 3.5 | | |
| 2 | 820 | 823 | 3.0 | | |
| 3 | 816 | 818.5 | 2.5 | 3.0 | 0.4 |
| 4 | 820 | 823 | 3.0 | | |
| 5 | 823 | 826 | 3.0 | | |

TABLE 7

$\lambda_{LSPR}$ responses from plasmonic biosensor for different concentrations of miR-10b in 40% bovine plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 100 nM | | | |
| 1 | 818 | 830 | 12.0 | | |
| 2 | 821 | 831 | 10.0 | | |
| 3 | 819 | 834 | 15.0 | 12.0 | 1.9 |
| 4 | 820 | 832 | 12.0 | | |
| 5 | 816 | 827 | 11.0 | | |
| | | 10 nM | | | |
| 1 | 820 | 835 | 15.0 | | |
| 2 | 819 | 828 | 9.0 | | |
| 3 | 822 | 830 | 8.0 | 9.2 | 3.3 |
| 4 | 819 | 826 | 7.0 | | |
| 5 | 821 | 828 | 7.0 | | |
| | | 1 nM | | | |
| 1 | 821 | 828 | 7.0 | | |
| 2 | 819 | 828 | 9.0 | | |
| 3 | 821 | 830 | 9.0 | 8.8 | 1.1 |
| 4 | 818 | 828 | 10.0 | | |
| 5 | 819 | 828 | 9.0 | | |

TABLE 7-continued $\lambda_{LSPR}$ responses from plasmonic biosensor for different concentrations of miR-10b in 40% bovine plasma.

| Sensor # | $\lambda_{LSPR}$ (nm) for HS-C6-ssDNA-10b: PEG$_6$SH functionalized gold nanoprisms | $\lambda_{LSPR}$ (nm) after incubation in different concentrations of miR-10b | $\Delta\lambda_{LSPR}$ (nm) | Average $\Delta\lambda_{LSPR}$ (nm) | S.D. |
|---|---|---|---|---|---|
| | | 0.1 nM | | | |
| 1 | 819 | 824 | 5.0 | | |
| 2 | 821 | 828 | 7.0 | | |
| 3 | 819 | 825 | 6.0 | 6.2 | 0.8 |
| 4 | 818 | 825 | 7.0 | | |
| 5 | 820 | 826 | 6.0 | | |
| | | 0.01 nM | | | |
| 1 | 821 | 825 | 4.0 | | |
| 2 | 818 | 824 | 6.0 | | |
| 3 | 822 | 826 | 4.0 | 4.2 | 1.1 |
| 4 | 820 | 823 | 3.0 | | |
| 5 | 820 | 824 | 4.0 | | |
| | | 0.001 nM | | | |
| 1 | 821 | 825 | 4.0 | | |
| 2 | 819 | 822 | 3.0 | | |
| 3 | 818 | 821 | 3.0 | 3.4 | 0.5 |
| 4 | 820 | 824 | 4.0 | | |
| 5 | 818 | 821 | 3.0 | | |
| | | 0.0001 nM | | | |
| 1 | 819 | 822 | 3.0 | | |
| 2 | 818 | 820 | 2.0 | | |
| 3 | 820 | 822.5 | 2.5 | 2.5 | 0.5 |
| 4 | 817 | 820 | 3.0 | | |
| 5 | 819 | 821 | 2.0 | | |

TABLE 8

$\lambda_{LSPR}$ responses from plasmonic biosensor prepared with 100% ssDNA-21 without spacer for different concentrations of miR-21 in 40% human plasma.

| Sensor # | $\lambda_{LSPR}$ (nm) for HS-C6-ssDNA-21 functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 100 nM | | | |
| 1 | 810 | 820 | 10.0 | | |
| 2 | 811 | 822 | 11.0 | | |
| 3 | 809 | 818 | 9.0 | 9.6 | 1.1 |
| 4 | 810 | 820 | 10.0 | | |
| 5 | 809 | 817 | 8.0 | | |
| | | 10 nM | | | |
| 1 | 808 | 817 | 9.0 | | |
| 2 | 810 | 820 | 10.0 | | |
| 3 | 808 | 816 | 8.0 | 7.8 | 1.8 |
| 4 | 811 | 817 | 6.0 | | |
| 5 | 809 | 815 | 6.0 | | |
| | | 1 nM | | | |
| 1 | 809 | 814 | 5.0 | | |
| 2 | 810 | 814 | 4.0 | | |
| 3 | 811 | 817 | 6.0 | 5.2 | 1.3 |
| 4 | 810 | 815 | 5.0 | | |
| 5 | 808 | 814 | 6.0 | | |

TABLE 8-continued $\lambda_{LSPR}$ responses from plasmonic biosensor prepared with 100% ssDNA-21 without spacer for different concentrations of miR-21 in 40% human plasma.

| Sensor # | $\lambda_{LSPR}$ (nm) for HS-C6-ssDNA-21 functionalized gold nanoprisms | $\lambda_{LSPR}$ (nm) after incubation in different concentrations of miR-21 | $\Delta\lambda_{LSPR}$ (nm) | Average $\Delta\lambda_{LSPR}$ (nm) | S.D. |
|---|---|---|---|---|---|
| | | 0.1 nM | | | |
| 1 | 811 | 816 | 5.0 | | |
| 2 | 810 | 814 | 4.0 | | |
| 3 | 810 | 815 | 5.0 | 4.6 | 0.6 |
| 4 | 808 | 812 | 4.0 | | |
| 5 | 809 | 814 | 5.0 | | |
| | | 0.01 nM | | | |
| 1 | 807 | 810 | 3.0 | | |
| 2 | 808 | 812 | 4.0 | | |
| 3 | 810 | 813 | 3.0 | 3.4 | 0.5 |
| 4 | 809 | 812 | 3.0 | | |
| 5 | 808 | 812 | 4.0 | | |

TABLE 9

Calibration curve and the LODs derived for synthetic miR-X (X = 21, 10b) in different physiological medias.

| Type of miR-X | Physical media | Equation from calibration curve | $R^2$ value | Z value (nm) | LOD (fM) |
|---|---|---|---|---|---|
| X = 21 | PBS buffer | Y = 0.9185ln(X) + 12.5 | 0.95 | 2.7 | 23.2 |
| | 40% human plasma | Y = 0.5735ln(X) + 9.103 | 0.98 | 3.1 | 28.4 |
| | 40% bovine plasma | Y = 0.6887ln(X) + 9.2714 | 0.93 | 2.2 | 34.6 |
| X = 10b | PBS buffer | Y = 0.7466ln(X) + 10.679 | 0.97 | 2.8 | 26.1 |
| | 40% human plasma | Y = 0.5748ln(X) + 8.9821 | 0.98 | 3.1 | 35.9 |
| | 40% bovine plasma | Y = 0.6887ln(X) + 8.1571 | 0.97 | 1.3 | 47.4 |

TABLE 10

The limit of detection (LOD) calculated for the plasmonic biosensors in different physical media for miR-21 and miR-10b.

| Type of miR-X | Physical media | LOD (fM) | LOD (fg/µL) |
|---|---|---|---|
| X = 21 | PBS buffer | 23.2 | 0.154 |
| | 40% human plasma | 28.4 | 0.189 |
| | 40% bovine plasma | 34.7 | 0.231 |
| X = 10b | PBS buffer | 26.1 | 0.181 |
| | 40% human plasma | 35.9 | 0.249 |
| | 40% bovine plasma | 47.4 | 0.329 |

TABLE 11

$\lambda_{LSPR}$ responses from plasmonic biosensor for miR-21 in extracted total RNAs from plasma samples collected from PDAC patients.

| Sensor # | $\lambda_{LSPR}$ (nm) for HS-C6-ssDNA-21: PEG$_6$SH functionalized gold nanoprisms | $\lambda_{LSPR}$ (nm) after incubation in extracted RNAs samples from PDAC patients | $\Delta\lambda_{LSPR}$ (nm) | Average $\Delta\lambda_{LSPR}$ (nm) | S.D. |
|---|---|---|---|---|---|
| | | Sample-1 | | | |
| 1 | 820 | 825.5 | 5.5 | | |
| 2 | 818 | 824 | 6.0 | | |
| 3 | 820 | 826 | 6.0 | 6.0 | 0.4 |
| 4 | 819 | 825.5 | 6.5 | | |
| | | Sample-2 | | | |
| 1 | 818 | 823 | 5.0 | | |
| 2 | 819 | 824.5 | 5.5 | | |
| 3 | 818 | 824 | 6.0 | 5.4 | 0.4 |
| 4 | 816 | 821.2 | 5.2 | | |
| | | Sample-3 | | | |
| 1 | 819 | 823 | 4.0 | | |
| 2 | 818 | 823 | 5.0 | | |
| 3 | 821 | 824.8 | 3.8 | 4.4 | 0.6 |
| 4 | 817 | 821.8 | 4.8 | | |
| | | Sample-4 | | | |
| 1 | 817 | 820.8 | 3.8 | | |
| 2 | 819 | 822.5 | 3.5 | | |
| 3 | 818 | 822 | 4.0 | 3.8 | 0.2 |
| 4 | 820 | 824 | 4.0 | | |
| | | Sample-5 | | | |
| 1 | 819 | 822 | 3.0 | | |
| 2 | 818 | 821.8 | 3.8 | | |
| 3 | 820 | 823 | 3.0 | 3.5 | 0.5 |
| 4 | 818 | 822 | 4.0 | | |
| | | Sample-6 | | | |
| 1 | 818 | 821 | 3.0 | | |
| 2 | 817 | 819 | 2.0 | | |
| 3 | 819 | 822 | 3.0 | 2.5 | 0.5 |
| 4 | 818 | 820.2 | 2.2 | | |

TABLE 12

$\lambda_{LSPR}$ responses from plasmonic biosensor for miR-21 in extracted total RNAs from plasma samples collected from normal humans.

| Sensor # | $\lambda_{LSPR}$ (nm) for HS-C6-ssDNA-21:PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| Sample-1 | | | | | |
| 1 | 821 | 823 | 2.0 | | |
| 2 | 819 | 821.5 | 2.5 | | |
| 3 | 818 | 820.9 | 2.9 | 2.2 | 0.6 |
| 4 | 819 | 820.4 | 1.4 | | |
| Sample-2 | | | | | |
| 1 | 817 | 819.3 | 2.3 | | |
| 2 | 818 | 820.5 | 2.5 | | |
| 3 | 820 | 822.9 | 2.9 | 2.6 | 0.3 |
| 4 | 818 | 820.5 | 2.5 | | |
| Sample-3 | | | | | |
| 1 | 817 | 819 | 2.0 | | |
| 2 | 818 | 819.8 | 1.8 | | |
| 3 | 820 | 822.2 | 2.2 | 2.2 | 0.5 |
| 4 | 819 | 821.9 | 2.9 | | |
| Sample-4 | | | | | |
| 1 | 818 | 818.5 | 0.5 | | |
| 2 | 818 | 819.1 | 1.1 | | |
| 3 | 819 | 821 | 2.0 | 1.5 | 0.9 |
| 4 | 820 | 822.5 | 2.5 | | |
| Sample-5 | | | | | |
| 1 | 817 | 819 | 2.0 | | |
| 2 | 819 | 820.8 | 1.8 | | |
| 3 | 821 | 823.6 | 2.6 | 1.9 | 0.6 |
| 4 | 820 | 821.2 | 1.2 | | |
| Sample-6 | | | | | |
| 1 | 816 | 817.2 | 1.2 | | |
| 2 | 819 | 821.6 | 2.6 | | |
| 3 | 820 | 820.8 | 0.8 | 1.5 | 0.8 |
| 4 | 818 | 819.2 | 1.2 | | |

TABLE 13

$\lambda_{LSPR}$ responses from plasmonic biosensor for miR-10b in extracted total RNAs from plasma samples collected from PDAC patients.

| Sensor # | $\lambda_{LSPR}$ (nm) for HS-C6-ssDNA-10b:PEG$_6$SH functionalized gold nanoprisms | $\lambda_{LSPR}$ (nm) after incubation in extracted RNAs samples from PDAC patients | $\Delta\lambda_{LSPR}$ (nm) | Average $\Delta\lambda_{LSPR}$ (nm) | S.D. |
|---|---|---|---|---|---|
| Sample-1 | | | | | |
| 1 | 821 | 827 | 6.0 | | |
| 2 | 820 | 827 | 7.0 | | |
| 3 | 822 | 828.3 | 6.3 | 6.2 | 0.8 |
| 4 | 819 | 824.6 | 5.6 | | |
| Sample-2 | | | | | |
| 1 | 819 | 824 | 5.0 | | |
| 2 | 819 | 824.8 | 5.8 | | |
| 3 | 821 | 826 | 5.0 | 5.3 | 0.4 |
| 4 | 817 | 822.5 | 5.5 | | |
| Sample-3 | | | | | |
| 1 | 818 | 823 | 5.0 | | |
| 2 | 821 | 826 | 5.0 | | |
| 3 | 821 | 826 | 5.0 | 4.8 | 0.5 |
| 4 | 817 | 821 | 4.0 | | |
| Sample-4 | | | | | |
| 1 | 822 | 825.5 | 3.5 | | |
| 2 | 821 | 825 | 4.0 | | |
| 3 | 818 | 821.8 | 3.8 | 3.8 | 0.2 |
| 4 | 819 | 823 | 4.0 | | |
| Sample-5 | | | | | |
| 1 | 819 | 822 | 3.0 | | |
| 2 | 820 | 823.5 | 3.5 | | |
| 3 | 821 | 824.7 | 3.7 | 3.3 | 0.4 |
| 4 | 817 | 820 | 3.0 | | |
| Sample-6 | | | | | |
| 1 | 818 | 820 | 2.0 | | |
| 2 | 819 | 821.4 | 2.4 | | |
| 3 | 821 | 823 | 2.0 | 2.1 | 0.2 |
| 4 | 818 | 820 | 2.0 | | |

TABLE 14

$\lambda_{LSPR}$ responses from plasmonic biosensor for miR-10b in extracted total RNAs from plasma samples collected from normal humans.

| Sensor # | $\lambda_{LSPR}$ (nm) for HS-C6-ssDNA-10b:PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| Sample-1 | | | | | |
| 1 | 822 | 824.6 | 2.6 | | |
| 2 | 821 | 824 | 3.0 | | |
| 3 | 820 | 822 | 2.0 | 2.2 | 0.7 |
| 4 | 818 | 819.3 | 1.3 | | |
| Sample-2 | | | | | |
| 1 | 820 | 821.6 | 1.6 | | |
| 2 | 819 | 820 | 1.0 | | |
| 3 | 822 | 823 | 1.0 | 1.3 | 0.4 |
| 4 | 818 | 819.6 | 1.6 | | |
| Sample-3 | | | | | |
| 1 | 819 | 820.8 | 1.8 | | |
| 2 | 822 | 823 | 1.0 | | |
| 3 | 820 | 821 | 1.0 | 1.1 | 0.5 |
| 4 | 819 | 819.5 | 0.5 | | |
| Sample-4 | | | | | |
| 1 | 820 | 821.3 | 1.3 | | |
| 2 | 820 | 821.6 | 1.6 | | |
| 3 | 817 | 819 | 2.0 | 1.6 | 0.3 |
| 4 | 819 | 820.3 | 1.3 | | |
| Sample-5 | | | | | |
| 1 | 818 | 819 | 1.0 | | |
| 2 | 822 | 824 | 2.0 | | |
| 3 | 820 | 821 | 1.0 | 1.2 | 0.5 |
| 4 | 820 | 820.8 | 0.8 | | |

TABLE 14-continued $\lambda_{LSPR}$ responses from plasmonic biosensor for miR-10b in extracted total RNAs from plasma samples collected from normal humans.

| Sensor # | $\lambda_{LSPR}$ (nm) for HS-C6-ssDNA-10b: PEG$_6$SH functionalized gold nanoprisms | $\lambda_{LSPR}$ (nm) after incubation in extracted RNAs samples from normal humans | $\Delta\lambda_{LSPR}$ (nm) | Average $\Delta\lambda_{LSPR}$ (nm) | S.D. |
|---|---|---|---|---|---|
| | | Sample-6 | | | |
| 1 | 819 | 821 | 2.0 | | |
| 2 | 817 | 819 | 2.0 | | |
| 3 | 820 | 821 | 1.0 | 1.5 | 0.6 |
| 4 | 819 | 820 | 1.0 | | |

TABLE 15

Comparison of $\Delta\lambda_{LSPR}$ responses with their concentrations and the qRT-PCR folds for miR-21 in extracted total RNAs from plasma samples collected from PDAC patients.

| Sample | ~$\Delta\lambda_{LSPR}$ (nm) | Concentration (fg/µL) | qRT-PCR folds |
|---|---|---|---|
| 1 | 6.0 | 345.4 | 8.12 |
| 2 | 5.4 | 187.4 | 4.34 |
| 3 | 4.4 | 65.2 | 1.24 |
| 4 | 3.8 | 30.8 | 0.714 |
| 5 | 3.5 | 22.5 | 0.572 |
| 6 | 2.5 | 8.4 | 0.172 |

TABLE 16

Comparison of $\Delta\lambda_{LSPR}$ responses with their concentrations for miR-21 in extracted total RNAs from plasma samples collected from normal humans.

| Sample | ~$\Delta\lambda_{LSPR}$ (nm) | Concentration (fg/µL) |
|---|---|---|
| 1 | 2.2 | 6.1 |
| 2 | 2.6 | 7.7 |
| 3 | 2.2 | 5.9 |
| 4 | 1.5 | 3.4 |
| 5 | 1.9 | 4.3 |
| 6 | 1.5 | 3.1 |

TABLE 17

Comparison of $\Delta\lambda_{LSPR}$ responses with their concentrations and the qRT-PCR folds for miR-10b in extracted total RNAs from plasma samples collected from PDAC patients.

| Sample | ~$\Delta\lambda_{LSPR}$ (nm) | Concentration (fg/µL) | qRT-PCR folds |
|---|---|---|---|
| 1 | 6.2 | 1298 | 30.5 |
| 2 | 5.3 | 340 | 10.7 |
| 3 | 4.8 | 161.3 | 5.0 |
| 4 | 3.8 | 42.5 | 1.23 |
| 5 | 3.3 | 22.1 | 0.711 |
| 6 | 2.1 | 4.2 | 0.115 |

TABLE 18

Comparison of $\Delta\lambda_{LSPR}$ responses with their concentrations for miR-10b in extracted total RNAs from plasma samples collected from normal humans.

| Sample | ~$\Delta\lambda_{LSPR}$ (nm) | Concentration (fg/µL) |
|---|---|---|
| 1 | 2.2 | 6.6 |
| 2 | 1.3 | 1.5 |
| 3 | 1.1 | 1.3 |
| 4 | 1.6 | 2.1 |
| 5 | 1.2 | 1.6 |
| 6 | 1.5 | 1.8 |

TABLE 19

$\lambda_{LSPR}$ responses from plasmonic biosensor for miR-21 in plasma samples without any extraction collected from PDAC patients.

| Sensor # | $\lambda_{LSPR}$ (nm) for HS-C$_6$-ssDNA-21: PEG$_6$SH functionalized gold nanoprisms | $\lambda_{LSPR}$ (nm) after incubation in plasma samples from PDAC patients | $\Delta\lambda_{LSPR}$ (nm) | Average $\Delta\lambda_{LSPR}$ (nm) | S.D. |
|---|---|---|---|---|---|
| | | Sample-1 | | | |
| 1 | 814 | 820.5 | 6.5 | | |
| 2 | 816 | 822 | 6.0 | | |
| 3 | 816 | 823 | 7.0 | 6.4 | 1.0 |
| 4 | 820 | 826 | 6.0 | | |
| | | Sample-2 | | | |
| 1 | 815 | 821 | 6.0 | | |
| 2 | 817 | 823 | 6.0 | | |
| 3 | 814 | 819.6 | 5.6 | 5.8 | 0.3 |
| 4 | 816 | 821.4 | 5.4 | | |
| | | Sample-3 | | | |
| 1 | 814 | 829.5 | 5.5 | | |
| 2 | 816 | 821 | 5.0 | | |
| 3 | 820 | 825 | 5.0 | 5.3 | 0.3 |
| 4 | 818 | 823.6 | 5.6 | | |
| | | Sample-4 | | | |
| 1 | 818 | 823 | 5.0 | | |
| 2 | 816 | 820.5 | 4.5 | | |
| 3 | 814 | 818.7 | 4.7 | 4.7 | 0.2 |
| 4 | 820 | 824.6 | 4.6 | | |
| | | Sample-5 | | | |
| 1 | 819 | 823 | 4.0 | | |
| 2 | 821 | 825.5 | 4.5 | | |
| 3 | 813 | 817 | 4.0 | 4.2 | 0.2 |
| 4 | 817 | 821.2 | 4.2 | | |
| | | Sample-6 | | | |
| 1 | 814 | 817.5 | 3.5 | | |
| 2 | 817 | 820.5 | 3.5 | | |
| 3 | 816 | 820 | 4.0 | 3.5 | 0.4 |
| 4 | 815 | 818 | 3.0 | | |

TABLE 20

Comparison of $\Delta\lambda_{LSPR}$ responses with their concentrations for miR-21 in from plasma samples collected from PDAC patients.

| Sample | ~$\Delta\lambda_{LSPR}$ (nm) | Concentration (fg/µL) |
|---|---|---|
| 1 | 6.4 | 1202.1 |
| 2 | 5.8 | 338.8 |
| 3 | 5.3 | 150.5 |
| 4 | 4.7 | 52.2 |

TABLE 20-continued

Comparison of $\Delta\lambda_{LSPR}$ responses with their concentrations for miR-21 in from plasma samples collected from PDAC patients.

| Sample | ~$\Delta\lambda_{LSPR}$ (nm) | Concentration (fg/μL) |
|---|---|---|
| 5 | 4.2 | 21.1 |
| 6 | 3.5 | 7.6 |

Example 2

Fabrication of miR-10b Sensor, and Characterization of Long-Term Stability and Selectivity.

Chemically synthesized gold nanoprisms, which displayed $\lambda_{LSPR}$ at 750, 800, and 820 nm in acetonitrile with average edge-lengths of 34, 42, and 47 nm, respectively, as determined from scanning electron microscopy images, were used in sensor fabrication. A red-shift change in $\lambda_{LSPR}$ position occurred during the functionalization of gold nanoprisms with 42 nm of average edge-length, which were attached onto silanized glass. The red-shift of the $\lambda_{LSPR}$ position suggested an increase in local refractive index from the attachment of molecular species on the gold nanoprism's surface. The LODs of miR-10b detection for 34, 42, and 47 nm edge-length nanoprisms were calculated in human plasma and were found to be 47.5, 0.091, and 0.083 fM, respectively (see Table 22). The LODs were calculated by measuring the $\Delta\lambda_{LSPR}$ for the blank sample (mixed -S-PEG6:-SC6-ssDNA-10b functionalized gold nanoprisms attached onto silanized glass substrate) and then calculating the Z (mean+3σ) value. The Z value was then converted into the relative concentration using the calibration curve. The data suggest that as the edge-lengths of the nanoprisms increase, their sensing volume also increases, thereby enhancing the LSPR sensitivity of the nanoprisms. This result is also in agreement with the literature where largest gold nanoparticles demonstrated highest LSPR-based sensing ability towards the detection of proteins. Thus, a minute change in a nanoprism's local dielectric environment due to analyte absorption can dramatically influence the LSPR properties and $\lambda_{LSPR}$ position. It is important to mention that the final $\lambda_{LSPR}$ values after -ssDNA-miR-10b and miR-10b hybridization were determined in PBS buffer (wet LSPR-based sensors) instead of air in order to avoid the effects of bulk refractive index caused by the surrounding media (water). Moreover, our lowest LOD of 83 aM was more than $10^6$, $10^4$, and $10^3$ fold lower than the label-free fluorescent-, microring resonator-, and nanopore-based miR sensors, respectively. To the best of our knowledge, this is the lowest LOD reported in the literature for LSPR-based sensors for detecting any-type of biomolecules in complex physiological media such as human plasma. This label-free technique has also proven to be more sensitive than metal nanoparticle-based surface-enhanced Raman scattering sensing (LOD=1.5 fM) of mouse pancreatic tumor.

The best LOD of the LSPR-based sensors described in this example were fabricated with 47 nm edge-length gold nanoprisms and demonstrated an LOD of 83.2 aM. However, functionalization of gold nanoprisms with 1:1 mole ratio of HS-C6-ssDNA-10b and $PEG_6$-SH shifted the $\lambda_{LSPR}$ peak to ~863 nm. Upon further incubation with miR-10b, the $\lambda_{LSPR}$ position shifted even closer to the near-infrared region, where other biological constituents present in the media and a water peak could interfere with reading the $\lambda_{LSPR}$ of nanoprisms and potentially cause misleading LOD values. Therefore, the 42-nm edge length nanoprisms ($\lambda_{LSPR}$=~800 nm) (LOD=91 aM) were used for LSPR-based sensor fabrication for further studies as described below. The LOD was slightly lower (32.6 aM) and exhibited less background signal in the LSPR peak shift ($\Delta\lambda_{LSPR}$) in PBS buffer than in human plasma (91 aM) (Table 23). These data are in agreement with the finding of a higher LSPR-based detection of streptavidin in serum by comparison with PBS buffer. Therefore, it is possible that differences in ionic strength or salt concentrations between PBS buffer and plasma, in conjunction with some nonspecific adsorption of plasma protein could occur on the silanized glass substrate within the sensing volume of gold nanoprisms, which could explain the slight differences in assay sensitivity between PBS buffer and human plasma.

Figure 2:
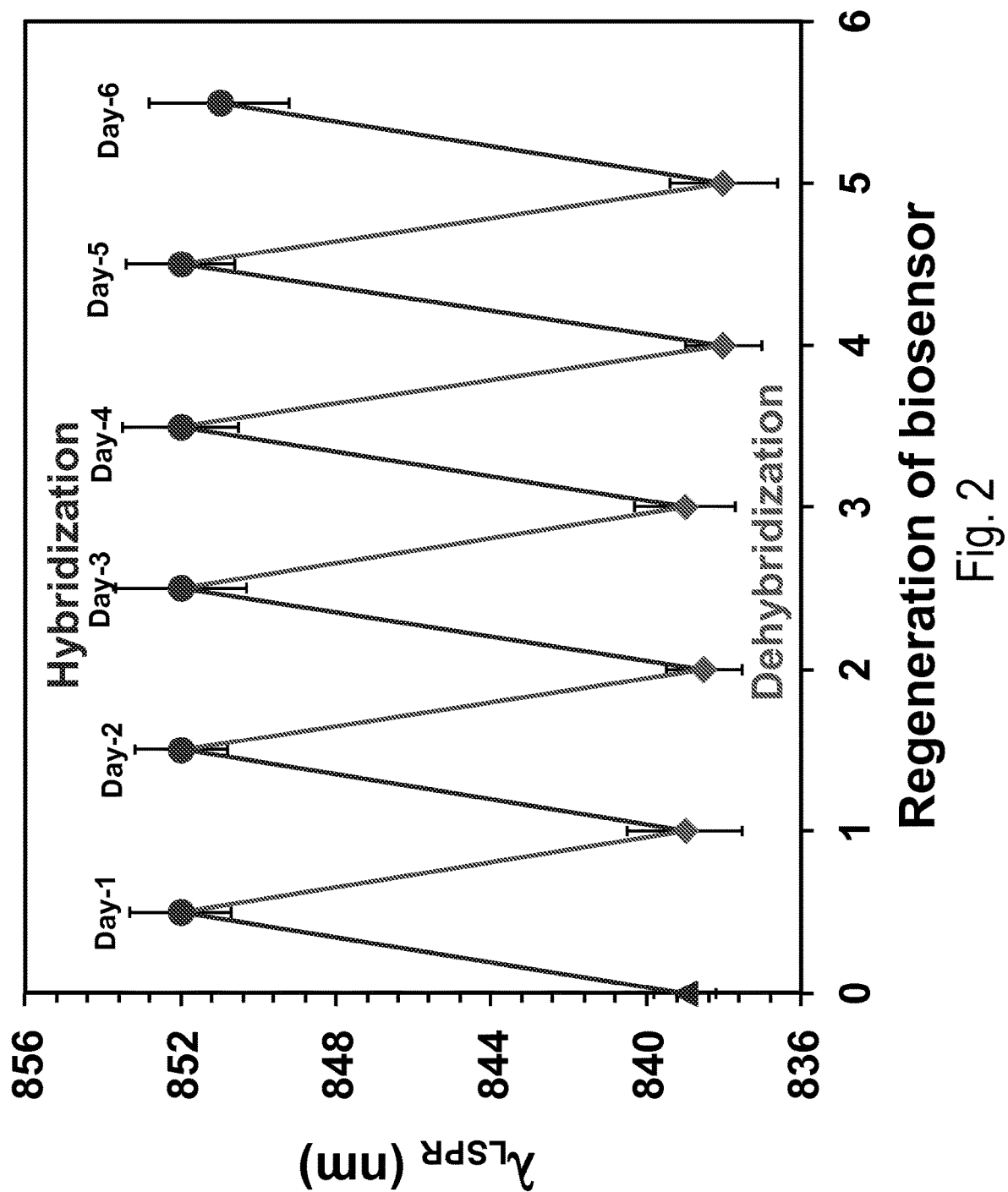
FIG. 2 is a plot showing changes in LSPR dipole peak position of gold nanoprisms functionalized with 1 µM:1 µM ratio of -C6-ssDNA-10b/-S-PEG6 upon hybridization and dehybridization for several cycles, as described in Example 2.

The regeneration ability of the LSPR-based sensor was tested by hybridization and dehybridization of miR-10b for at least 5 times over a 5-day period, using the same LSPR-based sensor while monitoring the $\lambda_{LSPR}$ shift, which was nearly identical each time before and after hybridization and dehybridization of miR-10b. The results are shown in FIG. 2. Therefore, the sensor is highly regenerative. Furthermore, the inert character of gold nanostructures towards biological constituents present in human plasma as well as the strong gold-sulfur bond which holds tightly the -ssDNA-10b, likely conferring long-term stability to the sensors, which will enhance their potential for development into point of care diagnostic tools. The LSPR-based sensors, which contain the specific antisense -ss-DNA-10b attached to the gold nanoprisms, were extremely specific towards their target miRs. The experimental data concerning regeneration and specificity of our sensors are discussed below. In the specificity study, 1.7 nm $\Delta\lambda_{LSPR}$ was observed when the LSPR-based sensor was incubated in a solution containing four different miRs (10 nM/miR; 40 nM total concentration). This value is very low in comparison to the 12.8 nm $\Delta\lambda_{LSPR}$ value observed upon incubation of our sensor with 10 nM miR-10b. Therefore, it is hypothesized that a $\Delta\lambda_{LSPR}$ of 1.7 nm could be due to a combination of instrumental noise and/or negligible nonspecific adsorption of miRs onto silanized glass substrate within the sensing volume of the gold nanoprisms, which was determined by us to be ~25 nm for 42 nm gold nanoprisms. Importantly, at the lower concentration range (100 fM and 100 aM), the $\Delta\lambda_{LSPR}$ values were same as blank samples (data not shown).

miR-10b has an identical seed sequence with miR-10a, but their mature forms differ at a single nucleotide. Thus, miR-10b and miR-10a contain nucleic acid A and U at the 12th position from 5' end, respectively. Moreover, the genes encoding miR-10b and 10a are located on chromosomes 2 and 17, respectively, and The Cancer Genome Atlas (TCGA) data indicate that 4% of PDACs exhibit miR-10b amplification and 4% exhibit miR-10a amplification, but these cases are not overlapping. Therefore, we next investigated the ability of our LSPR-based sensor to distinguish between miR-10b and miR-10a using the sensor, which was constructed with mixed -SC6-ssDNA-10b:-S-PEG6 in human plasma. The LSPR-based sensor displayed $\Delta\lambda_{LSPR}$ of 2.9 nm in 10 nM of miR-10a solution. This value is nearly 4.4 fold lower than $\Delta\lambda_{LSPR}$ observed for LSPR-based sensor upon incubation in 10 nM of miR-10b solution. No detectable $\lambda_{LSPR}$ shift was observed when miR-10a concentration was 1.0 pM.

This result is remarkable considering there is only one nucleotide difference between miR-10b and miR-10a, and that the sensor is proposed to rely on the -ssDNA:RNA duplex formation where attachment of miR-10b/10a to nanoprism-bound -ssDNA-10b increases the local dielectric environment and modulates $\Delta\lambda_{LSPR}$. It is believed that the 2.9 nm shift of $\Delta\lambda_{LSPR}$ for 10 nM of miR-10a was not controlled by the duplex formation between nanoprism-bound -ssDNA-10b and miR-10a since there is only a single nucleotide difference between them. This value is in agreement with the low molecular weight of miR-10a of ~6.9 kDa that will only influence local dielectric environment minimally, and it is expected that at higher concentrations miR-10a would attach to the sensors and influence the LSPR properties.

It is hypothesized that due to -ssDNA-10b and miR-10b duplex formation, a long distance charge transport takes place that alters the electron density and electromagnetic field around the nanoprisms, resulting in alteration of their LSPR properties. A long distance charge transport through a duplex DNA backbone is known to occur where a single base pair mismatch influences the conductivity significantly. Therefore, it is believed in the case of duplex formation between nanoprisms bound -ssDNA-10b and miR-10a the delocalization of free electrons of gold nanoprisms throughout the entire DNA helix did not take place. In order to test this hypothesis, LSPR-based sensors were designed by functionalizing gold nanoprisms by -SC6-ssDNA-10a:-S-PEG6 and the sensitivity was determined using miR-10a in human plasma where LOD was found to be an ~75 aM (data not shown). This result is expected because -ssDNA-10a and miR-10a form a duplex structure without any nucleotide mismatch, which would result in free electrons delocalization.

It is believed that one nucleotide difference would not alter duplex formation between -ssDNA-10b and miR-10a, and that most of the miR-10a would therefore be attached onto the sensor's surface, akin to the -ssDNA-10b/miR-10b duplex. To test this hypothesis, the level of unbound miR-10a in 1.0 nM solution was quantified after incubating with human plasma the LSPR-based sensor that was constructed with mixed -SC6-ssDNA-10b:-S-PEG6. The LSPR-based sensor displayed an average 2.5 nm shift of $\Delta\lambda_{LSPR}$, as expected. The miR-10a remaining in solution was then assayed using a sensor constructed with mixed -SC6-ss-DNA-10a:-S-PEG6, which revealed an average 6.1 nm shift in the $\Delta\lambda_{LSPR}$. Based on the miR-10a calibration curve, this $\Delta\lambda_{LSPR}$ value corresponds to a concentration of $1.4\times10^{-4}$ nM, which is ~$7\times10^3$ fold lower than the original 1.0 nM miR-10a concentration. In parallel, the level of unbound miR-10b in 1.0 nM solution was quantified after incubating with human plasma the LSPR-based sensor that was constructed with mixed -SC6-ssDNA-10b:-S-PEG6. A 5.4 nm shift of $\Delta\lambda_{LSPR}$ was observed, which corresponds to a concentration of $4.3\times10^{-5}$ nM using the equation for the calibration curve reported in Table 22. This value is only 3 fold lower than the value determined for miR-10a that was free in solution after incubation into miR-10b sensors. Thus, the vast majority of miR-10a and miR-10b formed a duplex with the -ssDNA-10b-based LSPR sensor, and a single nucleotide mismatch at the 12th position did not impede miR-10a duplex formation. Together, these results support the hypothesis of electron delocalization processes as a predominant factor of controlling the dramatic shift of $\Delta\lambda_{LSPR}$.

It is believe that this is the first LSPR-based sensing approach that is able to distinguish between nucleotides having a single base pair mismatch at concentrations <10 pM, which is at least a magnitude better than other label-free sensors. These experimental data are important in the context of precise quantification of miR-10b that is released by PCCs into the medium or circulation with a very low concentration as discussed below.

Quantitative Analysis of miR-10b Levels in Cultured Pancreatic Cancer Cells and their Released Products.

Chemotherapy resistance occurring in conjunction with a propensity to metastasize and a lack of early stage screening procedures contributes to the high PDAC-related mortality. It has therefore been proposed that a noninvasive test for the early detection of PDAC could significantly improve screening strategies and ultimately lead to a vastly improved prognosis in this treatment-recalcitrant cancer. It has been suggested that miR-10b may be an ideal plasma biomarker for PDAC, and that glypican-1 carried by exosomes could serve as an early diagnostic marker for PDAC. To further explore the possibility that circulating miR-10b could serve as a sensitive diagnostic marker for PDAC, it was sought to establish a highly sensitive and quantitative assay for miR-10b concentrations in various biological compartments that include PCC-derived conditioned media, exosomes, and plasma. Here, for the first time, a sensing approach was demonstrated which is able to precisely quantify the concentration of (i) extracted miR-10b from human PCCs, (ii) miR-10b in Roswell Park Memorial Institute (RPMI) medium and Dulbecco's modified Eagle's medium (DMEM) from these cells, (iii) extracted miR-10b from exosomes from these PCCs, and (iv) miR-10b in exosome-free supernatants (Sup) generated following two sequential ultracentrifugations (Sup-1 and Sup-2) as described below. The detection method described herein overcomes the limitation of the most widely used technique, qRT-PCR, which can only provide relative miR values rather than actual miR concentrations and which require RNA extraction procedures. Because the pancreatic tumor microenvironment (TME) is hypoxic and hypoxia up-regulates miR-10b expression, AsPC-1, BxPC-3, and PANC-1 cells engineered to overexpress miR-10b were grown under normoxia and hypoxia (1% $O_2$) conditions. By analyzing the concentration of miRs directly in media from the above PCCs as well as in exosomes released by these PCCs, it was possible to investigate the proportion of miR-10b released by PCCs directly into the culture medium by comparison to its release via exosomes.

Media from AsPC-1, BxPC-3, and PANC-1 cells, which were grown under normoxia and hypoxia conditions were collected and miR-10b was quantified using the LSPR-based technique and by qRT-PCT. Aliquots of media were subjected to two sequential ultracentrifugations with an intervening PBS was, and exosomes and supernatant-1 (Sup-1) were collected separately. Sup-1 was again ultracentrifuged at 100,000×g and Sup-2 was collected. The LSPR-based technique was used to quantify miR-10b directly in Sup-1 and Sup-2, while qRT-PCT was used to determine the relative miR-10b levels after RNA extraction. No visible residue was detected after the second ultracentrifugation.

Figure 3:
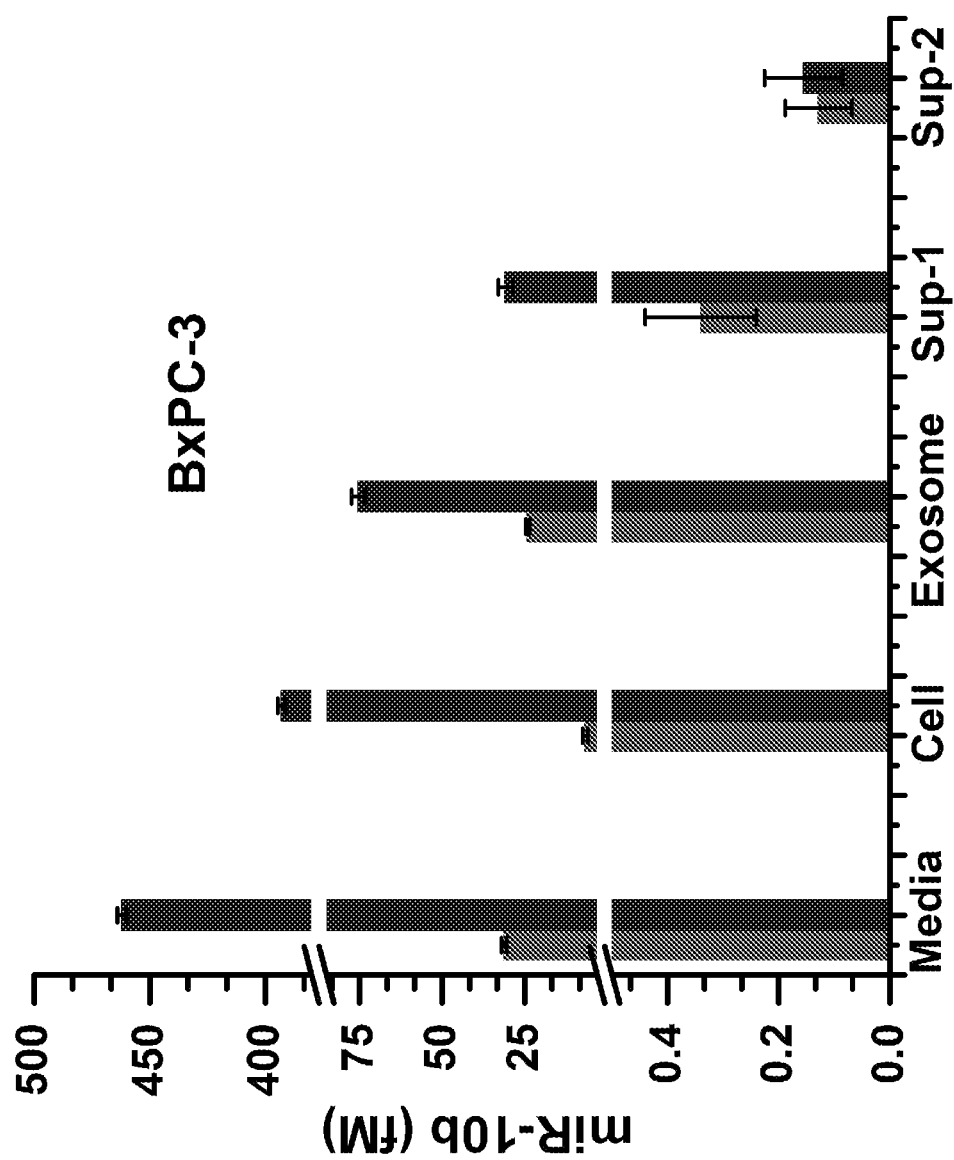
FIG. 3 is a plot of miR-10b concentration in various biological compartments of a BxPC-3 cell line, as determined by LSPR-based sensors, as described in Example 2.
Figure 4:
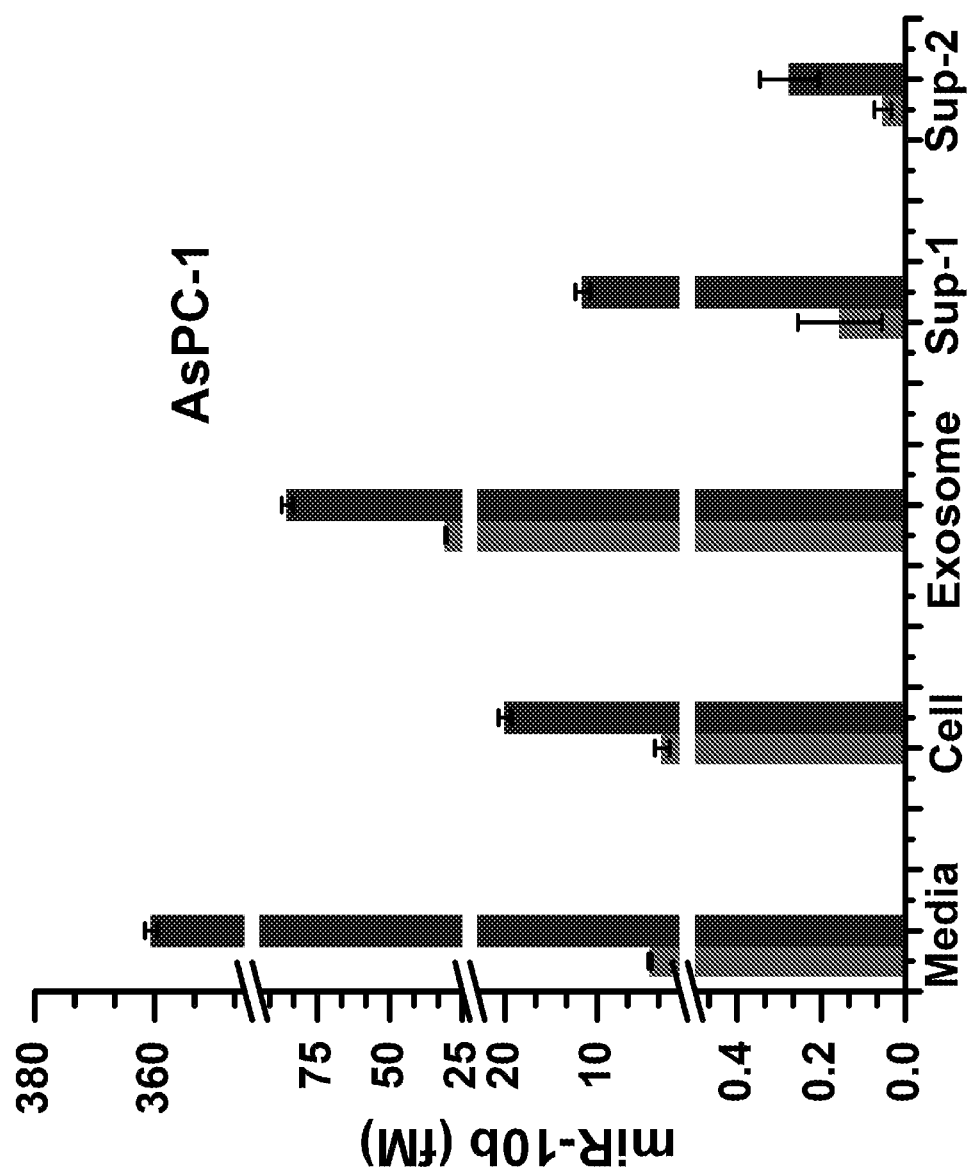
FIG. 4 is a plot of miR-10b concentration in various biological compartments of a AsPC-1 cell line, as determined by LSPR-based sensors, as described in Example 2.
Figure 5:
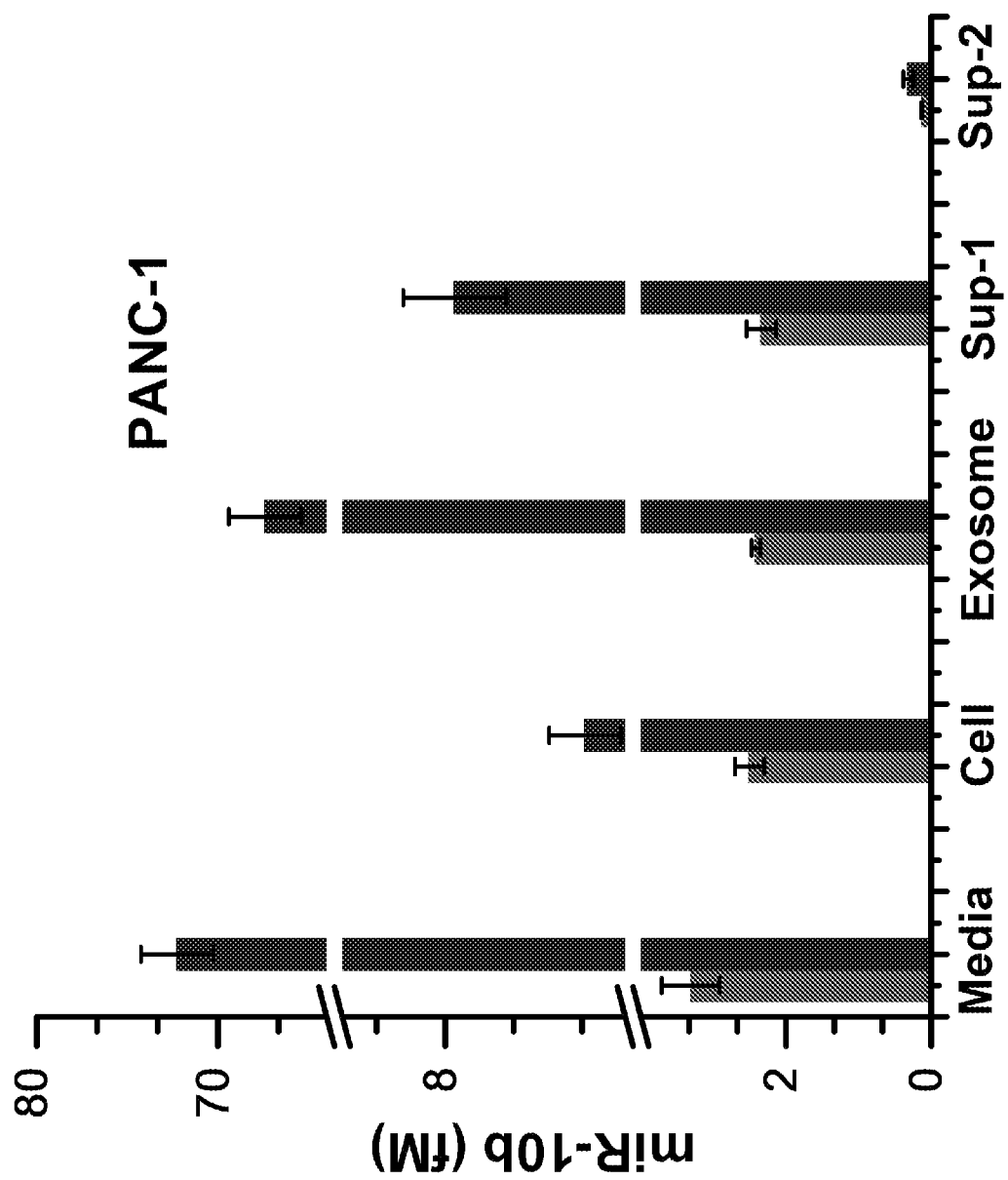
FIG. 5 is a plot of miR-10b concentration in various biological compartments of a PANC-1 cell line, as determined by LSPR-based sensors, as described in Example 2.

To quantify miR-10b levels in the above PCCs cells ($4\times10^5$) were lysed and total RNA (including miRs) was extracted using a TRIzol kit followed by a single-step purification with the Direct-zol RNA MiniPrep kit which yielded a final elution volume of 30 μL/sample. Next, 14 μL from each sample were used for LSPR-based detection, whereas the remaining 14 μL were used for qRT-PCR. miR-10b was quantified in crude media from each cell line by incubating over the LSPR-based sensor for 12 h, as described below. Subsequently, the sensors were washed with PBS buffer, and the $\lambda_{LSPR}$ was measured. FIGS. 3, 4, and 5 illustrate the LSPR-based determination of miR-10b concentrations in two types of media from three different PCCs. RPMI medium that was collected from BxPC-3 and AsPC-1 cells that were grown under hypoxia contained ~462, and 360 fM of miR-10b, respectively. DMEM collected from PANC-1 cells grown under hypoxia, contained ~70 fM of miR-10b. We observed a similar pattern for miR-10b concentrations that were determined following extraction of total RNA from BxPC-3, AsPC-1, and PANC-1 cells of ~390, ~20, and ~5 fM, respectively. The LSPR-based values were also compared with qRT-PCR data from the same samples and they showed the same general trend (FIGS. 6, 7, and 8).

FIGS. 3, 4, and 5 show the determination of miR-10b concentration in three different pancreatic cancer cell lines under two different culture conditions, normoxia (left bar in the pairs of bars) and hypoxia (right bar in the pairs of bars) in various biological compartments using the LSPR-based sensors. Determination of miR-10b concentrations in media, Sup-1, and Sup-2 was performed without RNA extraction, whereas total RNA was extracted from cells and exosomes. All three cell lines were engineered to overexpress miR-10b.

Figure 6:
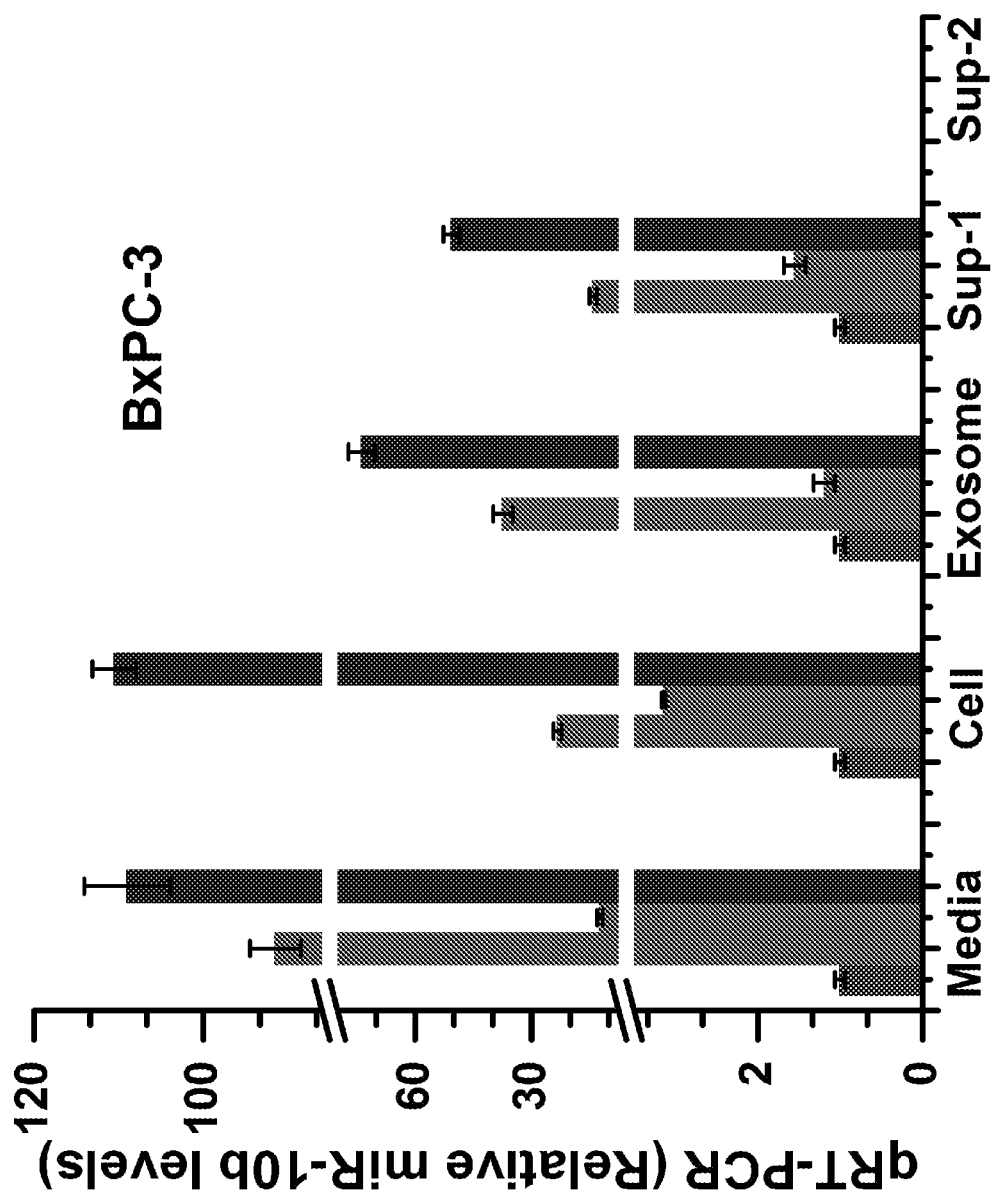
FIG. 6 is a plot of relative miR-10b levels in various biological compartments of a BxPC-3 cell line, as determined by qRT-PCT, as described in Example 2.
Figure 7:
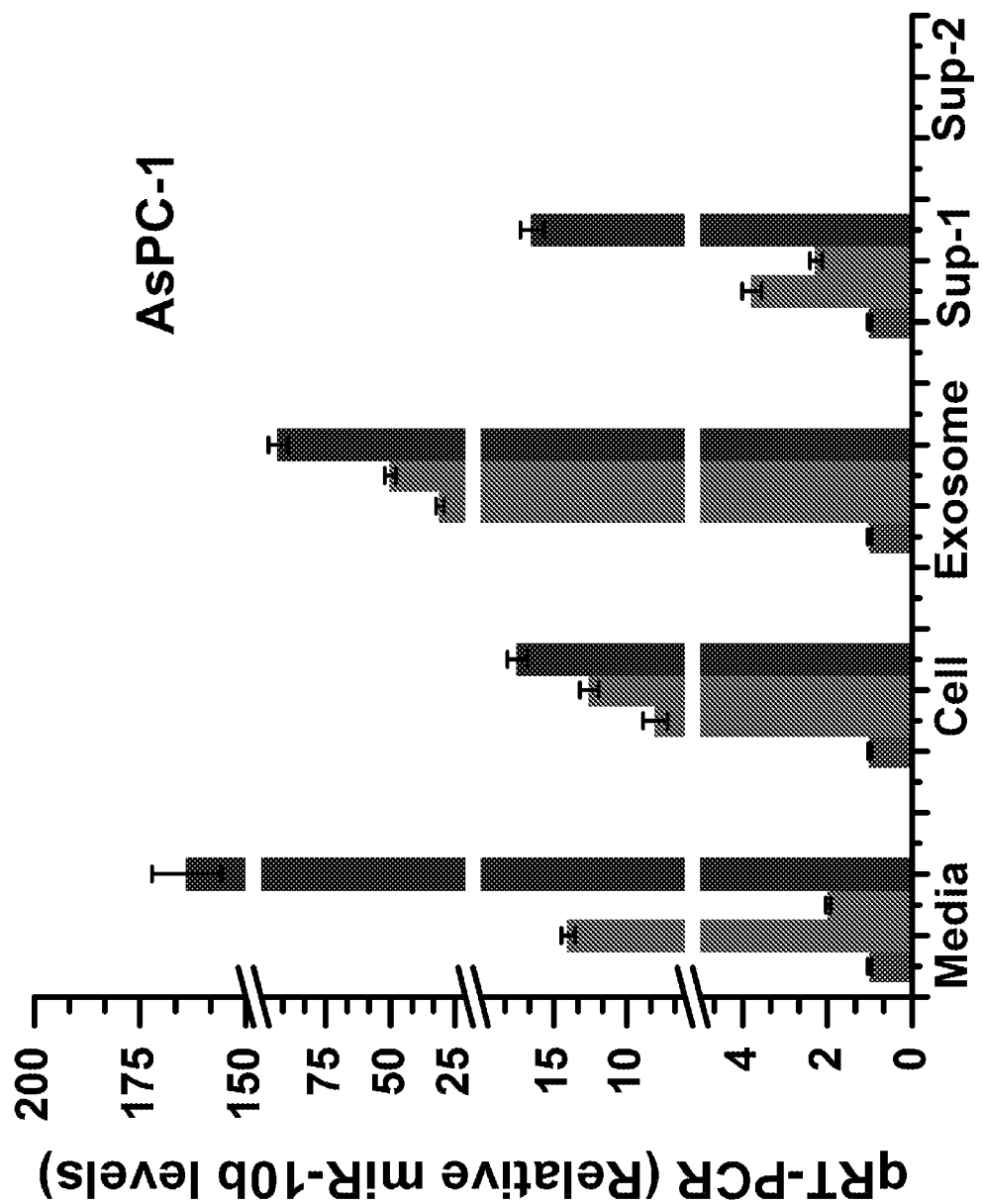
FIG. 7 is a plot of relative miR-10b levels in various biological compartments of a AsPC-1 cell line, as determined by qRT-PCT, as described in Example 2.
Figure 8:
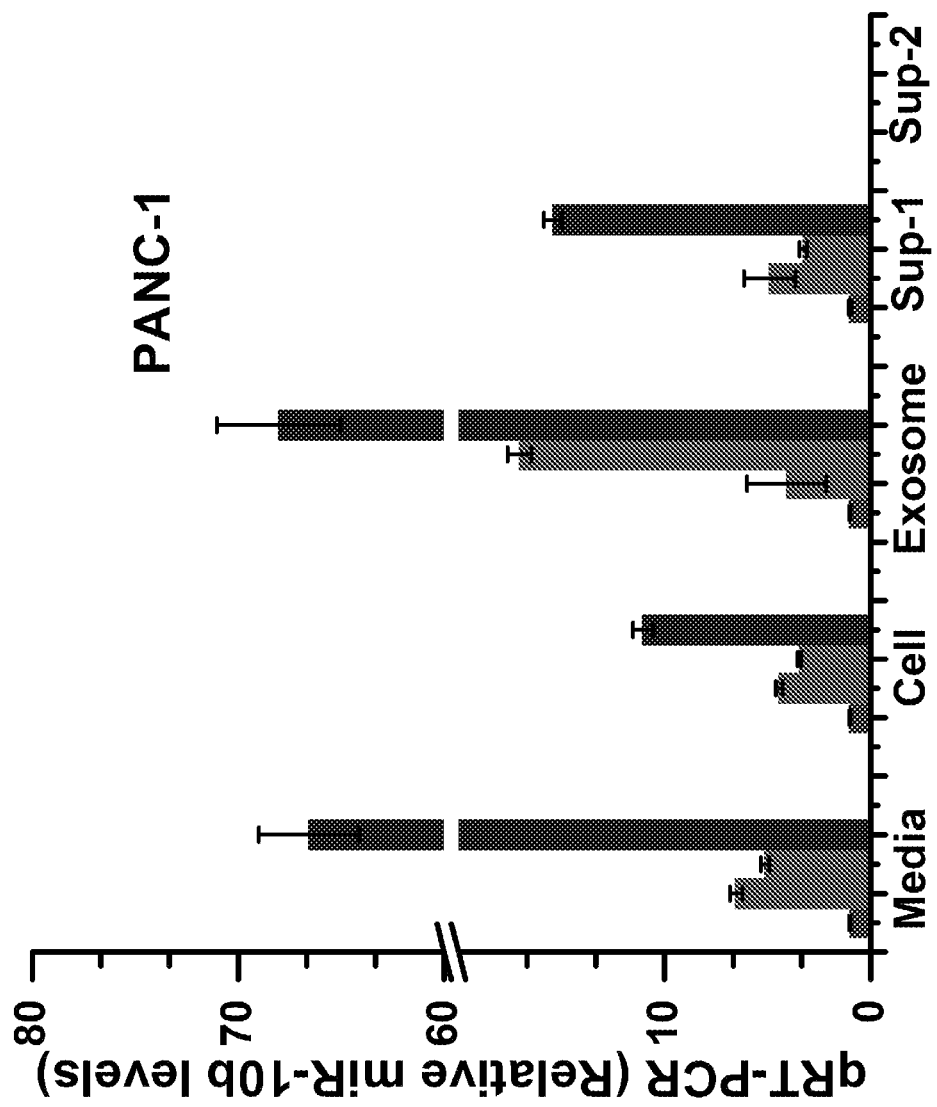
FIG. 8 is a plot of relative miR-10b levels in various biological compartments of a PANC-1 cell line, as determined by qRT-PCT, as described in Example 2.

FIGS. 6, 7, and 8 show qRT-PCT values for normoxia (left-most bar in the groups of four bars) and hypoxia (right-center bar in the group of four bars) using sham-transfected pancreatic cancer cells and cells engineered to overexpress miR-10b. miR-10b was assayed in total RNA extracted from media, cell, exosomes, and Sup-1 under normoxia (left-center bar in the group of four bars) and hypoxia (right-most bar in the group of four bars) conditions.

The LSPR-based concentration and qRT-PCT fold change in miR-10b levels in cells and exosomes were determined from aliquots derived from the corresponding total RNA samples. However, by qRT-PCR miR-10b was not detectable in Sup-2. The detailed procedure for exosomes isolation and RNAs extraction procedure are provided below.

To better understand the potential pathways for miR-10b release by PCCs, it was then sought to determine the concentrations of miR-10b in exosomes, and Sup-1 and Sup-2 generated following two sequential ultracentrifugations of media collected from PCCs that were cultured under hypoxia or normoxia conditions. Under hypoxia, miR-10b concentrations were ~76 fM, ~85 fM, and ~67 fM in exosomes collected from BxPC-3, AsPC-1, and PANC-1 cell-derived media, respectively. The concentrations of miR-10b were ~31 fM, ~12 fM and ~8 fM in Sup-1 from BxPC-3, AsPC-1, and PANC-1 cells, respectively, and in the ~150-300 aM range in Sup-2 (FIGS. 3-5). A similar trend was observed in the qRT-PCR analysis (FIGS. 6-8). This is the lowest concentration determined by any label-free miR sensors without RNA extraction. By contrast, miR-10b levels were unable to be quantified in Sup-2. Therefore, the LSPR-based sensing technique described herein allows for the quantitative assay of miR-10b in diverse physiological media without requiring miR extraction, and is more sensitive than the widely used qRT-PCR technique.

Using this LSPR-based technique it was also determined that miR-10b levels under hypoxic conditions in exosomes were at least three-fold (AsPC-1 and BxPC-3 cells) and as high as twenty eight-fold (PANC-1 cells) higher than under normoxic conditions (FIGS. 3-5). The LSPR-based concentration values were also compared with the qRT-PCR results (from the same sample with total RNAs extraction) and miR-10b levels exhibited the same trend by qRT-PCR as by LSPR (FIGS. 6-8). To confirm that the assays measured miR-10b in exosomes, transmission electron microscopy (TEM) images of the exosomes, which were isolated from PANC-1 cell-derived medium, were obtained. The diameters of the exosomes were determined (~60-140 nm), even though some appeared to be aggregated, which could be due to the drying process during the TEM grid preparation. The detailed procedures for exosomes collection and RNAs extraction are provided below. These findings thus demonstrate that miR-10b concentrations are elevated under hypoxic conditions in exosomes, raising the possibility that miR-10b acts within the hypoxic TME to promote PDAC biological aggressiveness.

The data presented above on accurate quantification of miR-10b in various biological compartments using the ultra-sensitive LSPR-based sensor provide insight into several important cellular processes that contribute to the release of miRs by PCCs in circulation. First, under hypoxia, miR-10b concentrations determined in exosomes collected from different cell lines were found to be comparable, and as high as 85 fM in ASPC-1 cells. Thus, PCCs release miR-10b rich exosomes into conditioned media, raising the possibility that it will be feasible to assay exosomal miRs as potential biomarkers of PDAC. Second, the concentrations of miR-10b in Sup-1 and Sup-2 were in the femtomolar and atto-molar range in all three-cell lines. Therefore, some residual miRs were still present in the supernatant collected from media even after two sequential ultracentrifugations with intervening washing with PBS. The presence of miR-10b in Sup-1 and Sup-2 suggests that in addition to being released via exosomes, miRs are released directly by PCCs into their environment. Although the specific cellular pathways for miR-10b release remain to be delineated, it is conceivable that miR-10b could detach from Ago2 protein-miR complexes as byproducts of dead cells, or be released due to the rupturing of exosomes or microvesicles because of high mechanical force applied during ultracentrifugation. The miR-10 concentrations in exosomes were at least 15% (BxPC-3 cells) and as high as 84% (PANC-1 cells) of total extracellular miR-10b levels (media, Sup-1 and Sup-2). Overall, this disclosure describes the first comprehensive determination of miR concentrations at the attomolar range in various PCCs, under various growth conditions, and in different biological compartments. This investigation has significant implications for the development of biomarkers for the early diagnosis of PDAC through isolation and quantification of circulating miR-10b, as discussed in the next section, as well as for the diagnosis of other cancers in which circulating miRs are elevated.

Exosome miR-10b Levels in Patients with Pancreatic Cancer and Chronic Pancreatitis.

Although hundreds of human miRs are known, their exact role in various aspects of cancer progression and modulation of cell proliferation, apoptosis, and metastasis is yet to be delineated. Importantly, these small, non-coding RNAs have the potential to serve as diagnostic markers for different diseases including PDAC. Plasma miR-10b levels, as determined by qRT-PCR, are elevated in PDAC patients by comparison with CP patients and normal control subjects or patients with gall-bladder disease. However, PCR-based assays require RNA extraction and purification, are only semi-quantitative, and are not sufficiently sensitive to differentiate miR-10b levels in patients with CP from levels in normal controls. As demonstrated above, the label-free, LSPR-based detection technique is not only able to assay attomolar concentrations of miR-10b directly in conditioned media, but also in PCC-derived exosomes. Therefore, it would be a breakthrough to establish an analytical technique that could be used to detect and quantify miR-10b directly in crude plasma samples.

Here, the first label-free assay to quantify and compare the miR levels between patients with PDAC (n=3), CP (n=3), and normal controls (n=3) is report. Moreover, the concentration of miR-10b in crude plasma, exosomes, and Sup-1 and Sup-2 is reported. The exosomes were collected from plasma through ultracentrifugation as described below. A brief TRIzol extraction, followed by a single-step purification using the direct-zol RNA MiniPrep kit makes this assay simple and innovative.

Exosomes are of endosomal origin and therefore express endosomal proteins such as tumor susceptibility gene 101 (Tsg101) and Alix. Exosomes that are of PDAC origin are also expected to express carbohydrate-associated 19-9 (CA19-9), which is a well-known pancreatic tumor marker in the circulation. To confirm that our plasma ultracentrifugation procedures yielded PDAC-derived exosomes, lysates of freshly isolated exosomes (20 µg/sample) and 50 µl of plasma supernatants were subjected to immunoblotting for TSG1, Alix, and CA19-9. The results show that plasma exosomes from PDAC patients express Alix, Tsg101, and CA19-9, and that the neither Alix nor Tsg101 are present in the plasma following the initial ultracentrifugation. By contrast, CA19-9, as expected, is present in exosome-depleted plasma.

Figure 9:
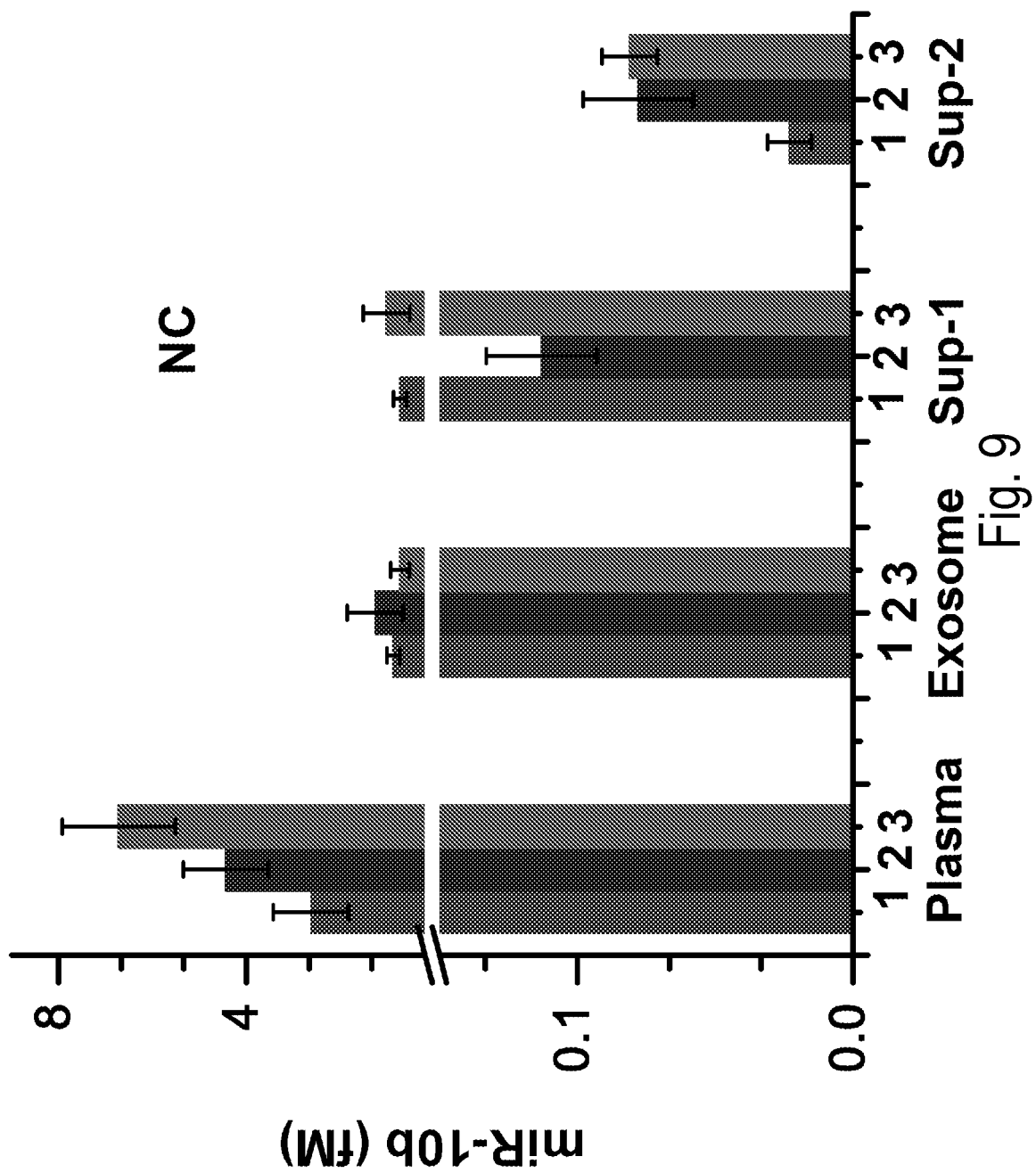
FIG. 9 is a plot of miR-10b concentration in various biological compartments from plasma samples of three normal controls, as determined by LSPR-based sensors, as described in Example 2.
Figure 10:
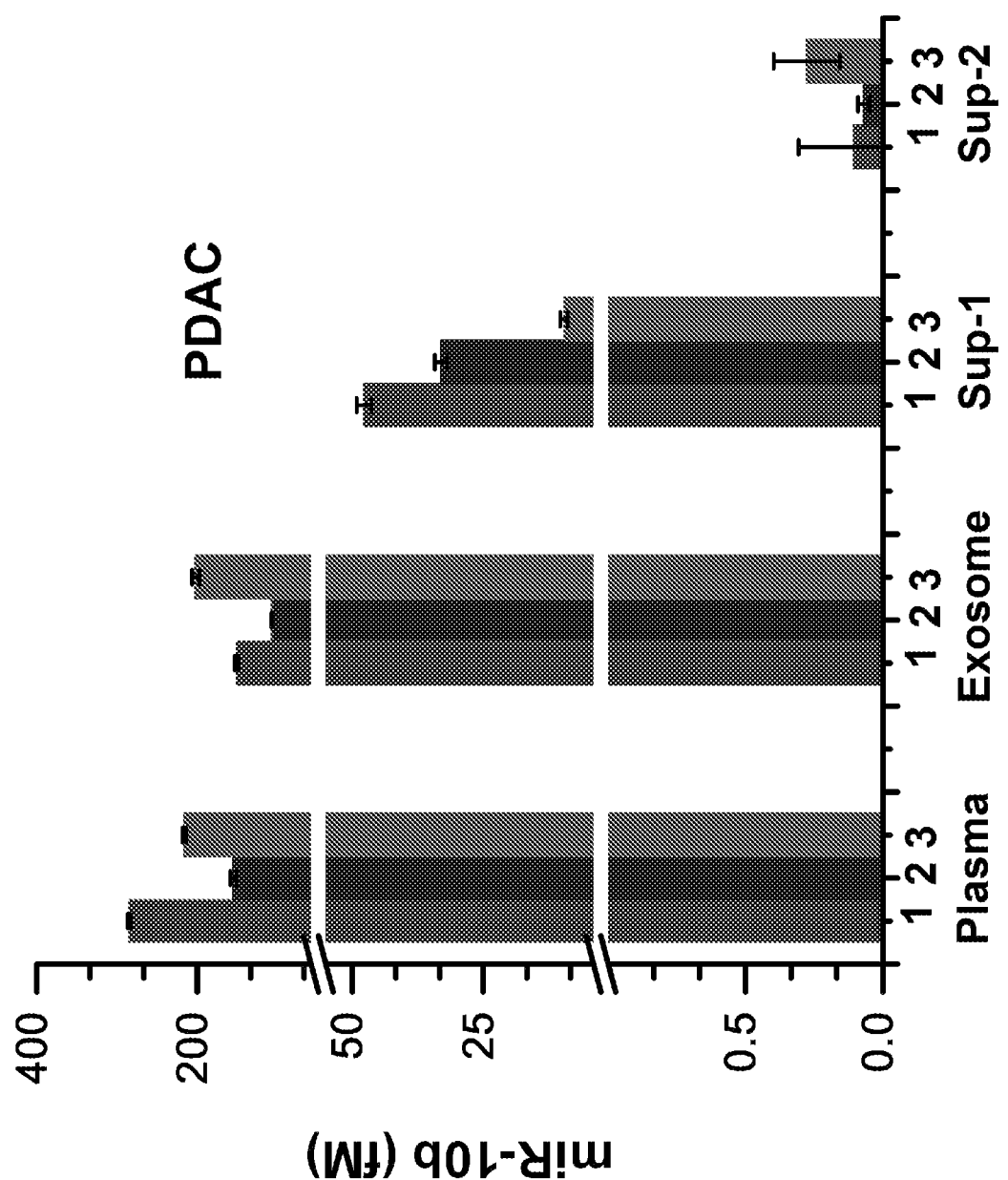
FIG. 10 is a plot of miR-10b concentration in various biological compartments from plasma samples of three patients with PDAC, as determined by LSPR-based sensors, as described in Example 2.
Figure 11:
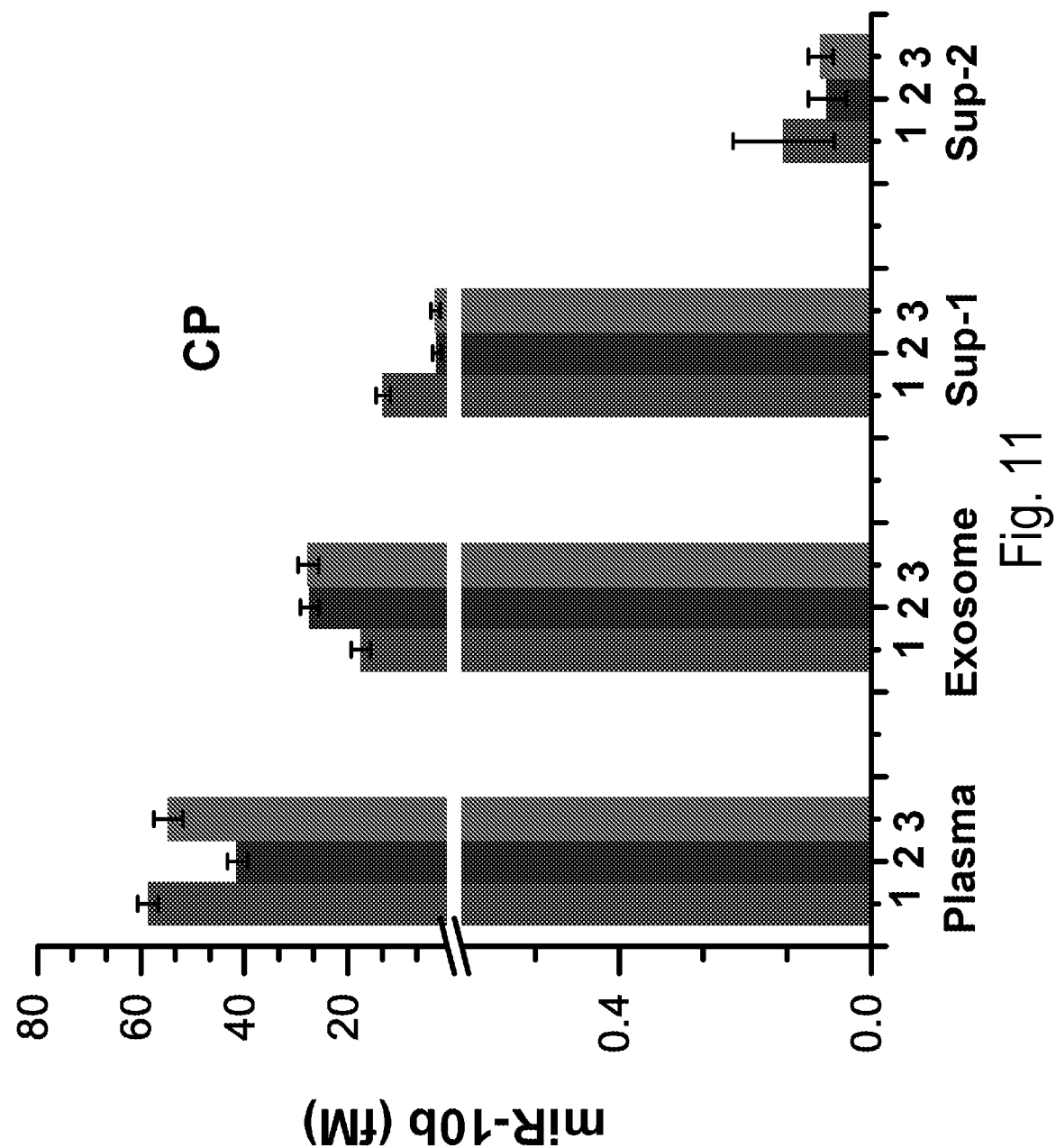
FIG. 11 is a plot of miR-10b concentration in various biological compartments from plasma samples of three patients with CP, as determined by LSPR-based sensors, as described in Example 2.
Figure 12:
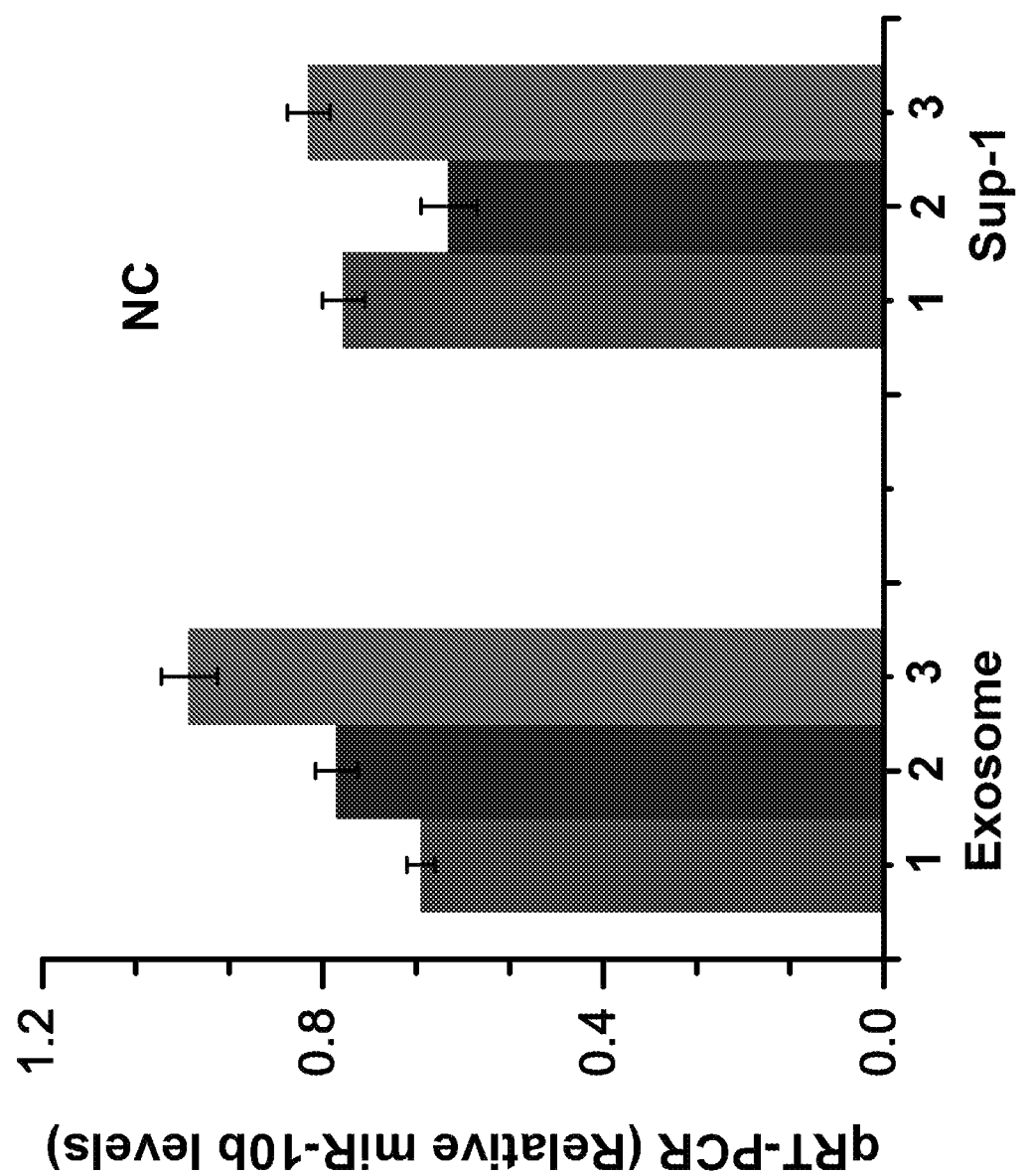
FIG. 12 is a plot of relative miR-10b levels in various biological compartments from plasma samples of three normal controls, as determined by qRT-PCR, as described in Example 2.
Figure 13:
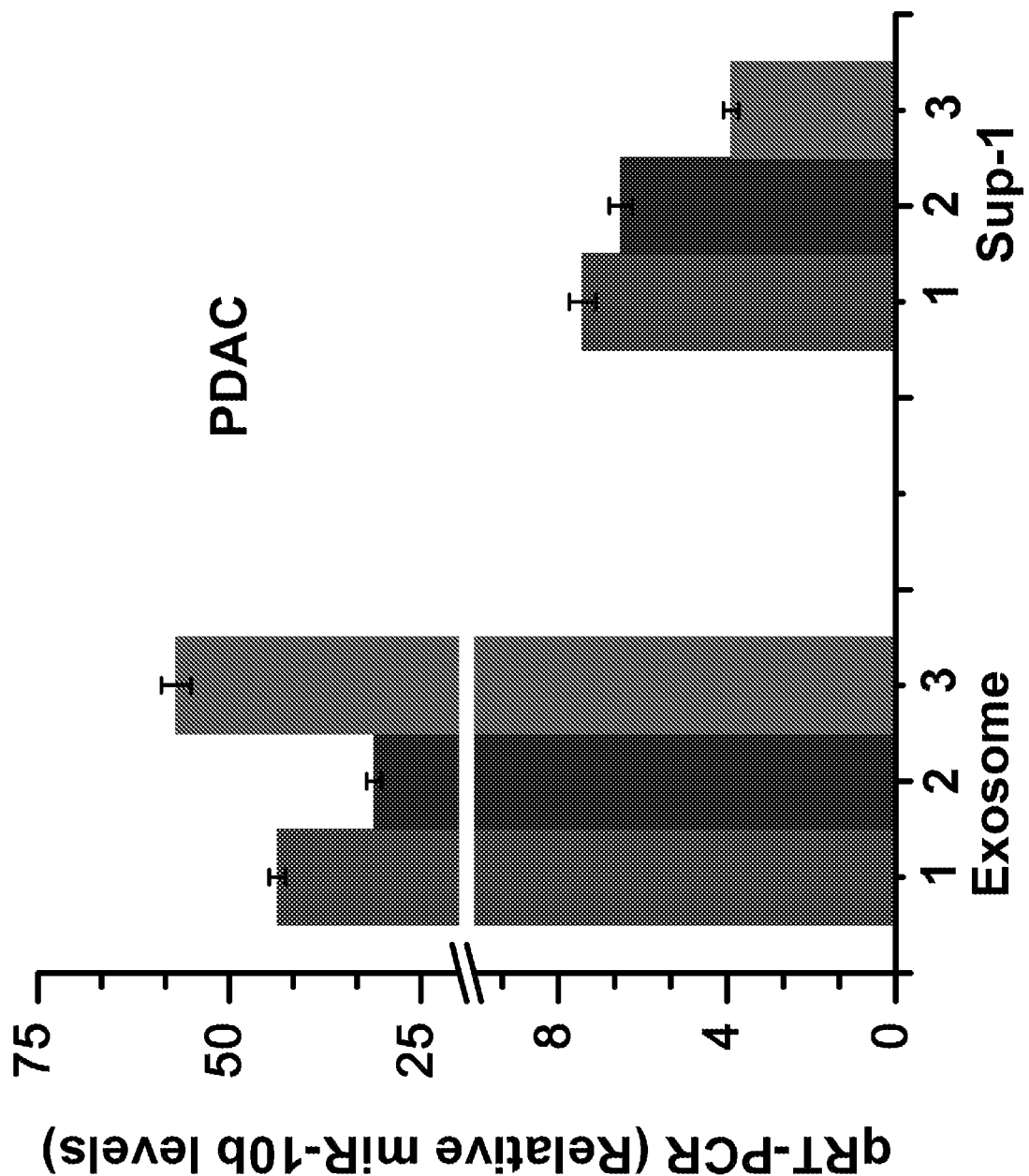
FIG. 13 is a plot of relative miR-10b levels in various biological compartments from plasma samples of three patients with PDAC, as determined by qRT-PCR, as described in Example 2.
Figure 14:
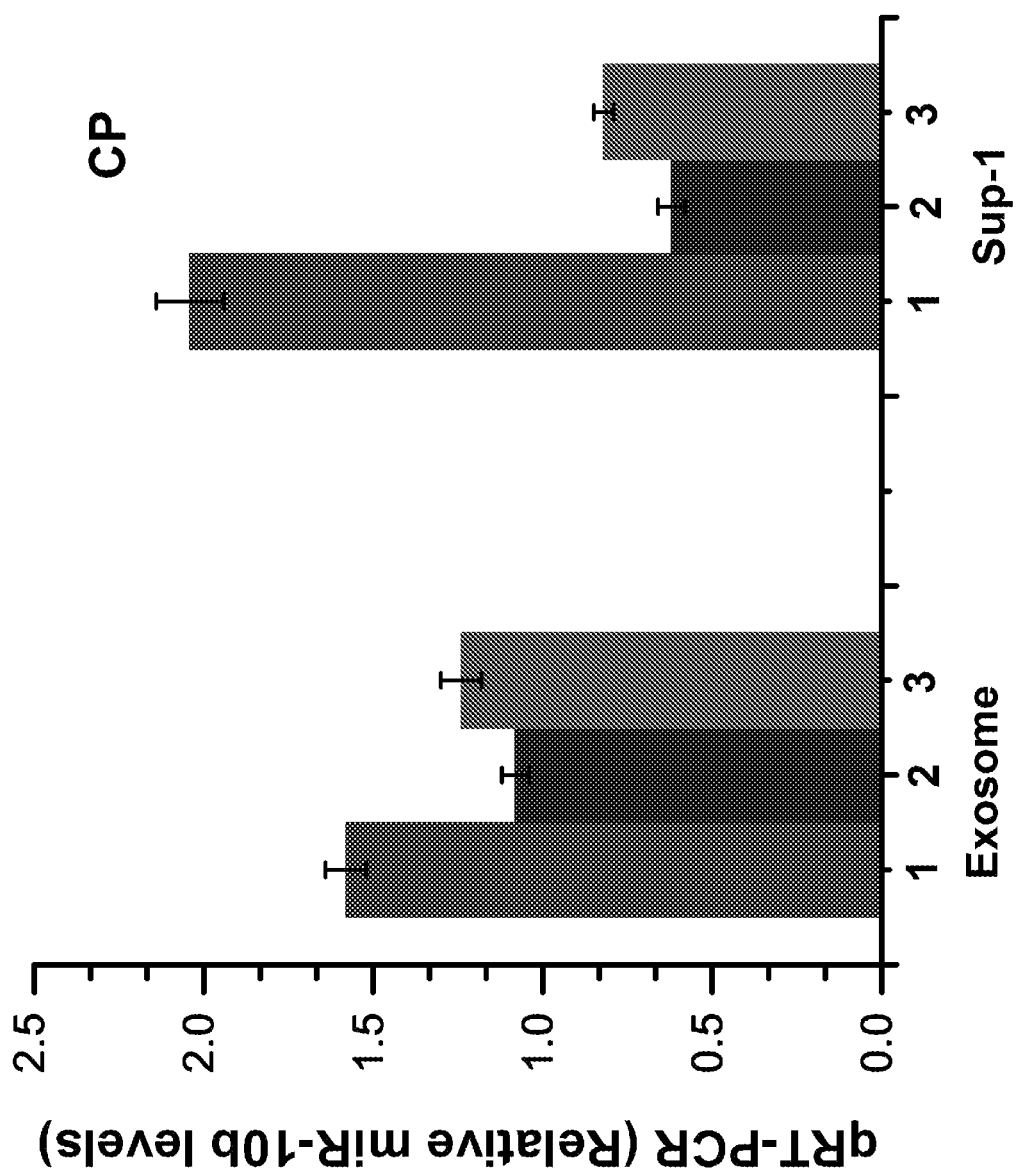
FIG. 14 is a plot of relative miR-10b levels in various biological compartments from plasma samples of three patients with CP, as determined by qRT-PCR, as described in Example 2.

FIGS. 9, 10, and 11 show a determination of miR-10b concentration in plasma samples from three normal control (NC), three patients with PDAC, and three patients with CP using the LSPR-based sensors described herein. Determination of miR-10b levels in plasma, Sup1, and Sup-2 were performed without RNA extraction, whereas total RNA was extracted from exosomes. FIGS. 12, 13, and 14 show qRT-PCR values for miR-10b from total RNA extracted from exosomes and Sup-1 in three NC, three patients with PDAC, and three patients with CP. The LSPR-based concentration and qRT-PCR values for miR-10b exosomes were determined from the same RNA samples from each subject, all performed in a blinded manner. Each individual bar represents a different subject. miR-10b levels in Sup-2 were below the level of detection by qRT-PCT and hence are not shown.

The concentrations of miR-10b in different biological compartments were determined using our LSPR-based assay, as shown in FIGS. 9, 10, and 11. All three samples from PDAC patients exhibited high levels of miR-10b in both plasma and circulating exosomes (FIG. 10). By contrast, the same LSPR-based assay revealed that miR-10b levels in plasma and exosomes from normal controls (FIG. 9) and CP patients (FIG. 11) were 50 to 60-fold lower and 4 to 10-fold lower, respectively, than the corresponding PDAC samples. Importantly, miR-10b levels in the CP samples (FIG. 11) were significantly higher than in normal controls (FIG. 9). FIGS. 12, 13, and 14 show the relative miR-10b levels determined by qRT-PCR. Supporting Information Table 7 provides the p values for the statistical analysis that was performed to compare PDAC, CP, and normal controls. Thus, the LSPR-based assay indicates that there are very high levels of miR-10b in the exosomes isolated from the plasma of PDAC patients, which is in contrast to observations in plasma from breast cancer patients where only 5% of miR-16, miR-21, and miR-24 were in the exosome compartment. Taken together, this data validate the hypothesis that PCCs are prone to release miR-10b as cargo within exosomes.

Comparing the LSPR- and qRT-PCR-based data, several conclusions can be drawn regarding the unique label-free technique. First, the trend of LSPR-based miR-10b concentration in exosomes and Sup-1 of three PDAC, three CP, and three normal control samples were identical to the well-established and most widely-used, qRT-PCR technique, underscoring the reliability of the nanoprism-based detection technique. Second, miR-10b levels in PDAC and CP samples were quantified directly in patient plasma, which cannot be accomplished by qRT-PCR. Third, the LSPR-based assay was able to quantify miR-10b level in Sup-2 but we were unable to extract sufficient RNAs from Sup-2 for quantification by qRT-PCR. This is due to the fact that the LSPR-based technique did not require any RNA extraction method, and is able to detect miR-10b in the sub-aM concentration range. Fourth, while qRT-PCR fails to differentiate between miR-10b levels in patients with CP by comparison with normal controls, the ultrasensitive LSPR-based sensor shows that plasma miR-10b levels are significantly higher in CP patients when compared to levels in normal controls. Moreover, there was at least a 5-fold increase in miR-10b levels in either plasma or exosomes in patients with CP when compared with normal controls. Thus, the LSPR-based detection technique displays unique aspects of modern analytical methodology that allows precise quantification of miRs at very low concentrations which is not feasible with any other known techniques.

CP is a chronic inflammatory condition of the pancreas associated with variable degrees of fibrosis which can lead to significant pancreatic exocrine and endocrine dysfunction, glucose intolerance, and diabetes. Although most patients with CP don't develop PDAC, it is well established that CP is associated with a higher risk for developing PDAC. However, there are no markers that will help stratify CP patients with respect to their risk for developing PDAC. Our observations that CP patients exhibit slight but significant increases in miR-10b levels in both the plasma and circulating exosomes by comparison with normal controls raise the possibility that monitoring for rising miR-10b levels in CP patients by using the ultrasensitive LSPR-based sensor could identify those patients that are at a high risk for developing PDAC and that need further evaluation by procedures such as endoscopic ultrasonography, thereby allowing for the early detection of CP progression to PDAC.

The LSPR-based quantification showed that miR-10b is present at high concentrations (~210 fM) in exosomes isolated from the plasma of PDAC patients, whereas the supernatants post-centrifugation (Sup-1: ~10-50 fM, and Sup-2: 70-300 aM) had exceedingly low miR-10b levels. Therefore, the vast majority of miR-10b that is released by PCCs is present in the exosomes. Importantly, analysis of the TCGA data for PDAC revealed that many of the PDAC tissue samples in TCGA exhibit increased miR-10b expression, ranging as high as ~180,000 reads per million (RPM). Moreover, there are five Stage IA and eight stage IB PDAC cases in the TCGA data, with mean miR-10b values of 13,400 RPM and 15,225 RPM, respectively, indicating that miR-10b is already elevated at the earliest stages of clinical presentation for PDAC. The simple, label-free, highly specific, and regenerative LSPR-based sensors would thus allow for quantitative measurements of miR-10b circulating in exosomes, which could serve as a biomarker for early PDAC diagnosis. Importantly, the working principle of the LSPR-based sensor is that the attachment of miR-10b to nanoprism-bound -ssDNA-10b increases the local dielectric environment and modulates $\Delta\lambda_{LSPR}$. Therefore, modifying the surface of the nanoprisms by any type of -ssDNA would allow for the quantitative detection of any complementary miR-X (for example, X=30c, 106b, 155, and 212) that is overexpressed in PDAC. This ultrasensitive assay will allow for the detection in plasma of miRs that are under-expressed in PDAC and other pathological conditions, and we have initiated the development of additional LSPR-based sensors that could quantify miR-X level, including those with single nucleotide specificity, in biological fluids and exosomes.

Chemicals. Chloro(triethylphosphine) gold (I) ($Et_3PAuCl$, 97%), poly(methylhydrosiloxane) (PMHS, Mn=1700-3300), trioctylamine (TOA, 98%), ACS grade acetonitrile ($CH_3CN$, 99.9%), methanol (99.8%), human plasma (contains 4% trisodium citrate and tested for HIV, hepatitis C and hepatitis B), thiol modified ssDNAs, microRNAs (miRs), Tris-base, magnesium chloride ($MgCl_2$), and potassium chloride (KCl) were purchased from Sigma Aldrich and were used as received. (3-mercaptopropyl)-triethoxysilane (MPTES, 94%) was purchased from Alfa Aesar, and ethanol (alcohol 200 proof) was purchased from Decon labs. RNase H enzyme and RNase H reaction buffer were purchased from New England bio labs inc. RNase free sterile water was obtained from Baxter Healthcare Corporation. 1,4-Dithiothreitol (DTT) was purchased from Roche Diagnostics. Anti-Alix (1:1000 dilution) from Sigma, anti-Tsg101 (1:200 dilution) from Santa Cruz, and anti-CA19-9 (1:200 dilution) from Abcam. Hydrochloric acid (HCl), sodium chloride (NaCl, ≥99.5%), sodium phosphate monobasic monohydrate ($NaH_2PO_4 \cdot H_2O$, >98%), sodium phosphate dibasic anhydrous ($Na_2HPO_4$), and the glass coverslips were purchased from Fisher Scientific. RBS 35 Detergent was obtained from Thermo Scientific and used as received. The super Sharpe silicon scanning probes (SSS-NCHR) for atomic force microscopy measurements were purchased from nanosensors. All water was purified using a Thermo Scientific Barnstead Nanopure system. Thiol modified oligonucleotides and all miRs were stored at −20° C. RNase free sterile water was used to prepare the PBS buffer solution. Polyethylene glycol thiol (PEG6-SH) was synthesized in our laboratory using published procedures (Lawrence, K. N.; Johnson, M. A.; Dolai, S.; Kumbhar, A.; Sardar, R. Solvent-like ligand-coated ultrasmall cadmium selenide nanocrystals: strong electronic coupling in a self-organized assembly. *Nanoscale* 2015, 7, 11667-11677). TRIzol and TRIzol LS were purchased from Life Technologies. Direct-zol RNA MiniPrep kit was purchased from Zymo Research.

Synthesis of Gold Nanoprisms with Various Edge Lengths. Gold nanoprisms were chemically synthesized according to our previously developed procedure with minor modification (Joshi, G. K.; McClory, P. J.; Muhoberac, B. B.; Kumbhar, A.; Smith, K. A.; Sardar, R. Designing Efficient Localized Surface Plasmon Resonance-Based Sensing Platforms: Optimization of Sensor Response by Controlling the Edge Length of Gold Nanoprisms. *J. Phys. Chem. C* 2012, 116, 20990-21000; and Joshi, G. K.; Smith, K. A.; Johnson, M. A.; Sardar, R. Temperature-Controlled Reversible Localized Surface Plasmon Resonance Response of Polymer-Functionalized Gold Nanoprisms in the Solid State. *J. Phys. Chem. C* 2013, 117, 26228-26237). Specifically, $Et_3PAu(I)Cl$ (8 mg, 0.02 mmol) was dissolved in 5 mL of acetonitrile and allowed to stir for 5 min at room temperature in an Erlenmeyer flask. 0.085 mL of TOA and 0.3 mL of PMHS were mixed with 1 mL of acetonitrile in a vial and injected into the above solution. The reaction mixture was then allowed to heat at 40° C. The solution color started to change from colorless to pink, purple, blue and at this point 14 mL acetonitrile was added to the reaction and the reaction was allowed to run for another 60 min, which resulted in a dark blue solution indicating the formation of nanoprisms with a stable localized surface plasmon resonance dipole peak ($\lambda_{LSPR}$) at 750 nm in acetonitrile (Table 22). At this point, the solution was removed from heat, centrifuged at 7000 rpm for 2 minutes, and used to fabricate LSPR-based sensors. The SEM analysis confirmed an average edge-length of 34 nm. Gold nanoprisms with an average 42 nm ($\lambda_{LSPR}$=800 nm) and 47 nm ($\lambda_{LSPR}$=820 nm) edge-length were synthesized using identical mole ratio of $Et_3PAuCl$ and PMHS, but changing the TOA amount of 0.085 and 0.1 mL, respectively.

Fabrication of LSPR-Based miR-10b Sensors. The gold nanoprisms containing LSPR-based sensors for miR-10b detection were developed using the method described above in Example 1. A tape cleaning procedure was carried out, in order to remove the non-prismatic nanostructures from the coverslips. Adhesive tape was applied to the gold nanoprisms-bound substrate surface, gently pressed down with a finger, and then slowly removed at a 90° angle. The nanoprisms-bound substrates were subjected to overnight incubation in a solution of PBS that contained a 1:1 ratio of 1.0 μM solution of HS-C6-ssDNA-10b and $PEG_6$-SH. Finally, the -S-C6-ssDNA-10b and -S-$PEG_6$ functionalized nanoprisms rinsed with adequate amount of PBS buffer solution to remove nonspecifically bound thiols. These functionalized nanoprisms, which were covalently attached onto supporting substrate and denoted as the LSPR-based sensor, were further utilized for miR-10b detection. We obtained the concentration of miR-10b in each media from the observed $\lambda_{LSPR}$ shift and converted it into the corresponding concentration using the calibration curve derived for miR-10b under various conditions, which include two different physiological media (human plasma and PBS buffer), two different culture media (RPMI and DMEM) and two different growth conditions (normoxia and hypoxia) (see Table 23).

Cell Culture. Stably overexpressing miR-10b and control ASPC-1, BxPC-3, and PANC-1 cells from ATCC (Manassas, Va., USA) were grown in culture at 37° C., 5% $CO_2$ in either RPMI 1640 (AsPC-1 and BxPC-3) or DMEM (PANC-1) with 5% FBS (exosomes depleted) and 1% penicillin/streptomycin as described previously (Ouyang, H.; Gore, J.; Deitz, S.; Korc, M. microRNA-10b enhances pancreatic cancer cell invasion by suppressing TIP30 expression and promoting EGF and TGF-[beta] actions. *Oncogene* 2014, 33, 4664-4674). Cells were plated in 60 mm dishes at a concentration of 4×10⁵ and grown in standard conditions (normoxia) for 72 hours. For hypoxic conditions, plates were removed from normoxia at 24 hours post-plating and transferred to a hypoxia chamber at 37° C., 5% $CO_2$, and 1% $O_2$ for 48 hours.

Engineered miR-10b PCCs and RNA Isolation. Cells were stably transduced to overexpress miR-10b with the MDH1-PGK-GFP microRNA-10b retroviral construct (Addgene plasmid 16070) with packaging plasmids PAX2 and pMD2.G. Sham-transfections to generate control cells were established by transduction with an empty MDH1-PGK-GFP construct (Addgene plasmid 11375) using Phoenix cells for retroviral packaging (Life Technologies). Harvested viruses were used for transduction as previously described (Liu, F.; Korc, M. Cdk4/6 Inhibition Induces Epithelial—Mesenchymal Transition and Enhances Invasiveness in Pancreatic Cancer Cells. *Mol. Cancer Ther.* 2012, 11, 2138-2148) and GFP-positive cells were isolated using flow cytometry 48 hours post-transduction (Flow Cytometry Facility, Indiana University School of Medicine, Indianapolis, Ind., USA). Sorted cells were plated and cultured as described above and allowed to recover for 48 hours prior to use in experiments. Validation of continued miR-10b overexpression was confirmed by monitoring GFP fluorescence and miR-10b levels by qRT-PCR. RNA was isolated from cells using TRIzol, or from media using TRIzol LS according to manufacturer's protocol.

Exosome Isolation from Plasma and RNA Isolation. Plasma samples from PDAC, CP, and normal controls (500 µL/sample) were centrifuged at 10,000×g (4° C.) for 30 minutes. Supernatants were transferred to a new tube and subjected to ultracentrifugation at 100,000×g for 70 minutes (4° C.). The supernatant was removed to a new tube for analysis and the pellet was the washed with 1× PBS and ultracentrifugation was repeated. RNA isolation (100 µL/plasma sample) was performed using the TRIzol kit followed by a single-step purification with the Direct-zol RNA MiniPrep kit (Zymo Research).

LSPR-based Quantification of Plasma and Exosomal miR-10b. Plasma (100 µL) from either PDAC or CP patients was diluted with 2.5 mL of PBS buffer. The LSPR-based sensors were incubated overnight and then rinsed with PBS buffer and extinction spectra were collected in PBS buffer to quantify the miR-10b levels. For exosomal miR-10b quantification, 20 µL of the TRIzol isolate was subjected to a single-step purification procedure with Direct-zol, and the sample was diluted with 2.0 mL of PBS buffer and incubated overnight with LSPR-based sensors. In this case, the extinction spectra were collected in PBS buffer. For accurate quantification of miR-10b in each compartment, each PDAC, CP, and normal control sample was assayed twice using a total of 10 sensors.

Spectroscopy and Microscopy Characterization, and qRT-PCR Assay. Absorption and extinction spectra in the range of 300-1100 nm were collected with a Varian Cary 50 Scan UV-visible spectrophotometer using 1 cm quartz cuvette. All the absorbance spectra were collected using 0.3 mL of reaction solution diluted in 2.0 mL of acetonitrile. Acetonitrile was used as a background for these measurements, and the background was run before collecting the absorbance spectra. All extinction spectra were measured in PBS buffer (pH 7.2) at room temperature unless otherwise specified. Here, the blank silanized glass coverslips immersed in PBS buffer were used as background, which was determined before collecting the extinction spectra. All AFM measurements were conducted in air utilizing tapping mode on a Bruker BioScope Catalyst with SSS-NCHR probes (Nanosensors) (tip radius ~2 nm). Images were collected using a tip velocity of 42 N/m over 1-2 uM scan sizes of three to five regions of each samples. All microscopy files were plain fitted and 2D fitted using Gwyddion. RNA was quantitated using the NanoDrop 2000 Spectrophotometer (Thermo) and samples were diluted to 3.0 ng/µL. Samples were converted to cDNA for miRNA-10b and RNU6B using RT primers (Life Technologies) and the TaqMan MicroRNA Reverse Transcription Kit (Life Technologies) according to manufacturer's protocol. Analysis by qRT-PCR was performed using the ViiA 7 Real-Time PCR System (Life Technologies) and fold changes were obtained by normalizing to control, normoxia conditions for each cell line, using the model presented in Pfaffl, 2001. Scanning electron microscopy (SEM) micrograms were acquired using a JEOL-FESEM at 15 kV. The average edge lengths of the nanoprisms were determined from the SEM images using ImageJ software. Approximately 500 nanoprisms were counted to determine the average values. Transmission electron microscopy (TEM) images of the exosomes were collected using Tecnai G212 Bio Twin TEM microscope at 80 kV operating voltage. The TEM images were captured using AMT CCD camera.

Data Processing and Statistical Analysis. Calibration curves using commercially-obtained miR-10b were performed five times independently and all measurements were reported as mean±standard deviation ($\sigma$). The maxima of UV-visible extinction spectra were used to determine the $\lambda_{LSPR}$ and the $\Delta\lambda_{LSPR}$ has been derived by taking the difference between the LSPR-based sensor's responses before and after hybridization ($\Delta\lambda_{LSPR}$). The LODs were calculated by measuring the $\Delta\lambda_{LSPR}$ for the blank (mixed -S-PEG6:-SC6-ssDNA-10b functionalized gold nanoprisms) and then obtained the Z (mean+3$\sigma$) value. The Z value was converted into the relative concentration using the calibration curve. Briefly, the blank measurement was obtained as the $\Delta\lambda_{LSPR}$ response for LSPR-based sensors after incubation in the respective media without any target miR-10b. Calibration curves constructed using commercially-obtained miR-10b in PBS buffer was used to determine the concentration of miR-10b in total RNA extracted from cell lines and exosomes. Culture media, sup-1, and sup-2 containing miR-10b was obtained using RPMI calibration (AsPC-1 and BxPC-3 cells) curves under hypoxia and normoxia conditions. Similar calibration curves were established using DMEM (PANC-1 cells). For patient plasma samples (PDAC, CP, and NC), and Sup-1 and Sup-2 samples, miR-10b concentration was obtained using the miR-10b calibration curve in human plasma. The miR-10b concentrations in total extracted RNA from exosomes isolated from patient plasma were calculated using the PBS buffer calibration curve.

In this example, the following oligonucleotide and miR strands were used: ssDNA-10b (SEQ ID NO: 2); target miR-10b (SEQ ID NO: 4); miR-16 (SEQ ID NO: 5); miR-126 (SEQ ID NO: 6); miR-141 (SEQ ID NO: 7); miR-122 (SEQ ID NO: 8); and miR-10a (SEQ ID NO: 9).

TABLE 21

Nucleic acid sequences used in this Example.

| strand | name | sequence | MW (kDa) | modification |
|---|---|---|---|---|
| 2 | ssDNA-10b | 5'-CACAAATTCGGTTCTACAGGGTA-3' | 7.1 | 5'thiol-$C_6$ |
| 4 | target miR-10b | 5'-UACCCUGUAGAACCGAAUUUGUG-3' | 7.0 | none |
| 5 | miR-16 | 5'-UAGCAGCACGUAAAUAUUGGCG-3' | 7.1 | none |
| 6 | miR-126 | 5'-CAUUAUUACUUUUGGUACGCG-3' | 6.3 | none |
| 7 | miR-141 | 5'-UAACACUGUCUGGUAAAGAUGG-3' | 6.7 | none |

TABLE 21-continued

Nucleic acid sequences used in this Example.

| strand | name | sequence | MW (kDa) | modification |
|---|---|---|---|---|
| 8 | miR-122 | 5'-UGGAGUGUGACAAUGGUGUUUG-3' | 6.8 | none |
| 9 | miR-10a | 5'-UACCCUGUAGAUCCGAAUUUGUG-3' | 6.9 | none |

TABLE 22

Calibration curve and the limit of detection (LOD) derived for human plasma supplemented with commercially-obtained miR-10b through LSPR-based sensor designed by using various edge lengths of gold nanoprisms.

| $\lambda_{LSPR}$ (nm)[a] | Edge length (S.D.)[b,c] | Equation from calibration curve | $R^2$ value | Z value (nm) | LOD (fM) |
|---|---|---|---|---|---|
| 750 | 34 (2.6) | Y = 0.6271ln(X) + 8.6786 | 0.97 | 2.44 | 47.5 |
| 800 | 42 (3.5) | Y = 0.5442ln(X) + 10.866 | 0.97 | 2.04 | 0.091 |
| 820 | 47 (4.9) | Y = 0.5333ln(X) + 10.494 | 0.94 | 1.80 | 0.083 |

TABLE 23

Calibration curve and the LODs derived with the commercially-obtained miR-10b through LSPR based sensor developed with ~42 nm edge length nanoprisms in different physiological media under various conditions.

| Physical media | Media condition | Equation from calibration curve | $R^2$ value | Z value (nm) | LOD (aM) |
|---|---|---|---|---|---|
| RPMI | Hypoxia | Y = 0.4035ln(X) + 8.9509 | 0.97 | 1.80 | 20.1 |
|  | Normoxia | Y = 0.4509ln(X) + 9.8236 | 0.94 | 1.50 | 9.61 |
| DMEM | Hypoxia | Y = 0.4086ln(X) + 8.9136 | 0.96 | 1.80 | 27.5 |
|  | Normoxia | Y = 0.4169ln(X) + 9.2527 | 0.94 | 1.80 | 17.2 |
| PBS buffer |  | Y = 0.5105ln(X) + 10.599 | 0.96 | 1.80 | 32.6 |

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A biosensor comprising:
a substrate having a substrate surface to which a localized surface plasmon resonance (LSPR) antenna is covalently affixed, the LSPR antenna affixed via an affixation surface of the LSPR antenna, and
the LSPR antenna having a functional surface opposite the affixation surface, wherein the functional surface is atomically smooth, the functional surface functionalized by a plurality of single-stranded DNA (ssDNA), which is complementary to at least a portion of a microRNA of interest,
wherein the LSPR antenna has an unbound absorption peak wavelength when contacted by a medium lacking the microRNA of interest and a bound absorption peak wavelength when contacted by a medium containing the microRNA of interest, wherein the bound absorption peak wavelength is shifted relative to the unbound absorption peak wavelength by an amount proportional to a concentration of the microRNA of interest in the medium without the use of a label,
wherein the LSPR antenna is a gold nanoprism, having an average edge length of between 34 nm to 47 nm, and
wherein the biosensor has a limit of detection of the microRNA of interest of less than 50 fM.

2. The biosensor of claim 1, wherein the functional surface is further functionalized by a plurality of spacer molecules.

3. The biosensor of claim 1, wherein the functional surface is substantially triangular.

4. The biosensor of claim 1, wherein the substrate is substantially transparent to electromagnetic radiation having a wavelength between 350 nm and 1200 nm.

5. The biosensor of claim 1, wherein the substrate comprises glass, quartz, indium tin oxide, optical fiber, flexible plastic, gold-coated glass, sapphire, or a combination thereof.

6. The biosensor of claim 1, wherein the medium is selected from the group consisting of human plasma, bovine plasma, phosphate buffered saline, water, serum, whole blood, pancreatic juice, urine, bile juice, saliva, liquid stool, peritoneal fluid, cerebrospinal fluid, or a combination thereof.

7. The biosensor of claim 1, wherein the biosensor has a limit of detection of the microRNA of interest of less than 1 aM.

8. The biosensor of claim 1, wherein a plurality of LSPR antennae are affixed to the substrate surface.

9. A biosensor array comprising a plurality of the biosensors of claim 1.

10. The biosensor array of claim 9, wherein two or more of the biosensors have sensitivity to different microRNAs of interest.

11. A method of detecting the presence of or quantifying the amount of a microRNA of interest in a medium suspected of containing the microRNA of interest, the method comprising:
a) contacting the biosensor of claim 1 with the medium potentially comprising the microRNA of interest;
b) measuring an absorption spectrum of the LSPR antenna, the absorption spectrum having a peak wavelength; and
c) determining the presence or quantity of the microRNA of interest in the medium based on the peak wavelength.

12. The method of claim 11, the method further comprising determining a concentration of the microRNA of interest in the medium based on the difference between the peak wavelength and an unbound absorption peak wavelength that is measured in the absence of the microRNA of interest.

13. The method of claim 11, the method further comprising contacting the biosensor with a cleaving enzyme to separate the microRNA of interest from the ssDNA thus regenerating the biosensor.

14. The method of claim 11, wherein the method has a limit of detection of the microRNA of interest of less than 1 aM.

15. The biosensor of claim 1, wherein the nanoprism is affixed to the substrate through a thiol bond.

16. The biosensor of claim 15, wherein the substrate surface is silanized.

17. The biosensor of claim 2, wherein the plurality of spacer molecules comprise a poly-ethylene glycol moiety.

18. The biosensor of claim 1, wherein the average edge length is 34 nm, 35 nm, 42 nm, or 47 nm.

19. The biosensor of claim 1, wherein the average edge length is 42 nm.

* * * * *